US012807730B2

(12) United States Patent
Johnston et al.

(10) Patent No.: US 12,807,730 B2
(45) Date of Patent: Nov. 24, 2026

(54) METHOD OF TREATING CANCER AND/OR INHIBITING BINDING OF PSGL-1 TO VISTA BY ADMINISTERING A PSGL-1 ANTIBODY OR A VISTA ANTIBODY

(71) Applicants: Bristol-Myers Squibb Company, Princeton, NJ (US); Five Prime Therapeutics, Inc., Thousand Oaks, CA (US)

(72) Inventors: Robert J. Johnston, San Mateo, CA (US); Andrew Rankin, Redwood City, CA (US); Arathi Krishnakumar, Chesterfield, NJ (US); Paul O. Sheppard, Granite Falls, WA (US); Arvind Rajpal, San Francisco, CA (US)

(73) Assignees: Bristol-Myers Squibb Company, Princeton, NJ (US); Five Prime Therapeutics, Inc., Thousand Oaks, CA (US)

( * ) Notice: Subject to any disclaimer, the term of this patent is extended or adjusted under 35 U.S.C. 154(b) by 97 days.

(21) Appl. No.: 18/543,912

(22) Filed: Dec. 18, 2023

(65) Prior Publication Data

US 2024/0228653 A1 Jul. 11, 2024

Related U.S. Application Data

(60) Continuation of application No. 17/695,081, filed on Mar. 15, 2022, now abandoned, which is a division of application No. 16/476,814, filed as application No. PCT/US2018/013171 on Jan. 10, 2018, now Pat. No. 11,306,150.

(60) Provisional application No. 62/445,071, filed on Jan. 11, 2017.

(51) Int. Cl.
*C07K 16/28* (2006.01)
*A61K 45/06* (2006.01)

(52) U.S. Cl.
CPC .......... *C07K 16/2896* (2013.01); *A61K 45/06* (2013.01); *C07K 2317/24* (2013.01); *C07K 2317/54* (2013.01); *C07K 2317/55* (2013.01); *C07K 2317/56* (2013.01); *C07K 2317/76* (2013.01); *C07K 2319/30* (2013.01); *C07K 2319/32* (2013.01)

(58) Field of Classification Search
CPC ............ C07K 16/2896; C07K 2317/24; C07K 2317/54; C07K 2317/55; C07K 2317/56; C07K 2317/76; C07K 2317/92; C07K 2319/30; C07K 2319/32; A61K 45/06; A61K 2039/505; A61P 35/00; G01N 33/6845; G01N 33/6854; G01N 2333/70596
See application file for complete search history.

(56) References Cited

U.S. PATENT DOCUMENTS 4,997,913 A 3/1991 Hellstrom et al.
5,827,817 A 10/1998 Larsen et al.
7,833,530 B2 11/2010 Alvarez et al.
8,114,968 B2 2/2012 Devy et al.
8,889,628 B2 11/2014 Shaw
10,259,866 B2 4/2019 Nitsch et al.
11,014,987 B2 5/2021 Snyder et al.
2005/0260711 A1 11/2005 Datta et al.
2010/0260765 A1 10/2010 Barry et al.
2010/0330078 A1 12/2010 Bender et al.
2011/0027278 A1 2/2011 Noelle et al.
2011/0081666 A1 4/2011 Alvarez et al.
2011/0172397 A1* 7/2011 Lin ......................... A61P 35/02 530/387.9
2012/0100140 A1 4/2012 Reyes et al.
2012/0108455 A1 5/2012 Kodandapani et al.
2012/0148571 A1 6/2012 Lasters et al.
2014/0056892 A1 2/2014 Noelle et al.
2014/0105912 A1 4/2014 Noelle
2014/0341920 A1 11/2014 Noelle et al.
2014/0378660 A1 12/2014 Short et al.
2015/0265703 A1 9/2015 Herting et al.
2015/0337053 A1 11/2015 McCarthy et al.
2016/0096891 A1 4/2016 Chen et al.
2016/0159927 A1 6/2016 Molloy et al.
2016/0176963 A1 6/2016 Maurer et al.
2016/0347814 A1 12/2016 Levine et al.
2016/0347849 A1 12/2016 Cai et al.
(Continued)

FOREIGN PATENT DOCUMENTS

CN 104968364 A 10/2015
CN 105246507 A 1/2016
(Continued)

OTHER PUBLICATIONS

Krishnamurthy VR, et al. (Mar. 31, 2015) Nature Communications. 6:6387. 12 pages. (DOI: 10.1038/ncomms7387).*
Muz B, et al. (2015) Biomedical Research International. vol. 2015, Article ID 417586, pp. 1-8.*
Ji et al., "Enhancing the Efficacy of Anti-tumor Immunotherapy by Targeting T cell Metabolism," J Nutr Oncol, 2019, 4 (2): 67-73.
Xuan et al., "Research progress on immune checkpoint molecule immunoglobulin variable domain inhibitor of T Cell activation (VISTA)," Chin J Cell Mol Immunol, 2017, 33(2): 266-269.
Zhou et al, "Important progress in international immunology research in 2019," Immunological Journal, 2020, 36(1): 1-10.
(Continued)

*Primary Examiner* — Robert S Landsman
(74) *Attorney, Agent, or Firm* — McNeill PLLC

(57) ABSTRACT

Methods of identifying and using PSGL-1 antagonists are provided. Such methods include, but are not limited to, methods of treating cancer. PSGL-1 antagonists include, but are not limited to, antibodies that bind PSGL-1 and antibodies that bind VISTA, wherein the antibodies inhibit PSGL-1 binding to VISTA, e.g., at acidic pH (e.g., pH 6.0), as well as PSGL-1 and VISTA extracellular domain polypeptides.

5 Claims, 5 Drawing Sheets

Specification includes a Sequence Listing.

(56) References Cited

U.S. PATENT DOCUMENTS

| | | | |
|---|---|---|---|
| 2017/0051061 | A1 | 2/2017 | Snyder et al. |
| 2017/0119877 | A1 | 5/2017 | Green et al. |
| 2017/0198052 | A1 | 7/2017 | Lin et al. |
| 2018/0306799 | A1 | 10/2018 | Snyder et al. |
| 2019/0330364 | A1 | 10/2019 | Johnston et al. |
| 2020/0055936 | A1 | 2/2020 | Johnston et al. |
| 2021/0017283 | A1 | 1/2021 | Johnston et al. |
| 2022/0073617 | A1 | 3/2022 | Johnston et al. |
| 2023/0192860 | A1 | 6/2023 | Su et al. |
| 2023/0310634 | A1 | 10/2023 | Rothstein et al. |

FOREIGN PATENT DOCUMENTS

| | | | |
|---|---|---|---|
| CN | 106414489 | A | 2/2017 |
| CN | 107922497 | A | 4/2018 |
| CN | 110563843 | A | 12/2019 |
| CN | 110740749 | A | 1/2020 |
| CN | 111971304 | A | 11/2020 |
| CN | 112638948 | A | 4/2021 |
| CN | 114729043 | A | 7/2022 |
| EP | 2291536 | A4 | 2/2013 |
| RU | 2550262 | C1 | 5/2015 |
| TW | 201619195 | A | 6/2016 |
| WO | 9201718 | A2 | 2/1992 |
| WO | 9410309 | A1 | 5/1994 |
| WO | 9411498 | A1 | 5/1994 |
| WO | 9506118 | A1 | 3/1995 |
| WO | 9530001 | A2 | 11/1995 |
| WO | 9706176 | A2 | 2/1997 |
| WO | 1997009068 | A2 | 3/1997 |
| WO | 9808949 | A1 | 3/1998 |
| WO | 9931117 | A1 | 6/1999 |
| WO | 0000610 | A2 | 1/2000 |
| WO | 2000012708 | A2 | 3/2000 |
| WO | 2000078961 | A1 | 12/2000 |
| WO | 0104297 | A2 | 1/2001 |
| WO | 0173028 | A2 | 10/2001 |
| WO | 2003105757 | A2 | 12/2003 |
| WO | 2004022594 | A2 | 3/2004 |
| WO | 2003013603 | | 6/2004 |
| WO | 2005027831 | A2 | 3/2005 |
| WO | 2005110475 | A2 | 11/2005 |
| WO | 2006012232 | A1 | 2/2006 |
| WO | 2006116181 | A2 | 11/2006 |
| WO | 2007033959 | A2 | 3/2007 |
| WO | 2007067984 | A2 | 6/2007 |
| WO | 2007100211 | A1 | 9/2007 |
| WO | 2009140623 | A2 | 11/2009 |
| WO | 2010104821 | A1 | 9/2010 |
| WO | 2011120013 | A2 | 9/2011 |
| WO | 2005110456 | | 2/2012 |
| WO | 2012033953 | A1 | 3/2012 |
| WO | 2012174001 | A1 | 12/2012 |
| WO | 2013082200 | A1 | 6/2013 |
| WO | 2013134743 | A1 | 9/2013 |
| WO | 2013192504 | A1 | 12/2013 |
| WO | 2014039983 | A1 | 3/2014 |
| WO | 2014089113 | A1 | 6/2014 |
| WO | 2014190356 | A2 | 11/2014 |
| WO | 2014197849 | A2 | 12/2014 |
| WO | 2015069770 | A1 | 5/2015 |
| WO | 2015097536 | A2 | 7/2015 |
| WO | 2015109340 | A2 | 7/2015 |
| WO | 2015187359 | A1 | 12/2015 |
| WO | 2015191881 | A2 | 12/2015 |
| WO | 2016007653 | A2 | 1/2016 |
| WO | 2016090347 | A1 | 6/2016 |
| WO | 2016094837 | A2 | 6/2016 |
| WO | 2016207717 | A1 | 12/2016 |
| WO | 2017078839 | A1 | 5/2017 |
| WO | 2017120534 | A1 | 7/2017 |
| WO | 2017137830 | A1 | 8/2017 |
| WO | 2017175058 | A1 | 10/2017 |
| WO | 2017181109 | A1 | 10/2017 |
| WO | 2017181139 | A2 | 10/2017 |
| WO | 2018027042 | A1 | 2/2018 |
| WO | 2018047143 | A1 | 3/2018 |
| WO | 2018132476 | A1 | 7/2018 |
| WO | 2018169993 | A1 | 9/2018 |
| WO | 2018195772 | A1 | 11/2018 |
| WO | 2018237287 | A1 | 12/2018 |
| WO | 2019078699 | A2 | 4/2019 |
| WO | 2019087092 | A1 | 5/2019 |
| WO | 2019165233 | A1 | 8/2019 |
| WO | 2019183040 | A1 | 9/2019 |
| WO | 2019185163 | A1 | 10/2019 |
| WO | 2019185879 | A1 | 10/2019 |
| WO | 2020014327 | A2 | 1/2020 |
| WO | 2021055698 | A1 | 3/2021 |

OTHER PUBLICATIONS

Almagaro et al., "Humanization of Antibodies," Frontiers in Bioscience, 2008, 13:1619-1633.

Bostrom et al., "Improving Antibody Binding Affinity and Specificity for Therapeutic Development," Methods Mol. Biol., 2009, 525:353-376.

Brown et al., "Tolerance to Single, but Not Multiple, Amino Acid Replacements in Antibody Vh CDR2: A Means of Minimizing B Cell Wastage from Somatic Hypermutation?," J Immunol, 1996, 156:3285-3291.

Casset et al., "A peptide mimetic of an anti-CD4 monoclonal antibody by rational design," Biochem. and Biophys. Res. Comm., 2003, 307:198-205.

Chen et al., "Selection and Analysis of an Optimized Anti-VEGF Antibody: Crystal Structure of an Affinity-matured Fab in Complex with Antigen," J. Mol. Biol., 1999, 293:865-881.

De Pascalis et al., "Grafting of "Abbreviated" Complementarity-Determining Regions Containing Specificity-Determining Residues Essential for Ligand Contact to Engineer a Less Immunogenic Humanized Monoclonal Antibody," J Immunol., 2002, 169:3076-3084.

Deng et al., "A New VISTA on combination therapy for negative checkpoint regulator blockade," J Immunotherapy Cancer, 2016, 4(1):1-7.

Extended European Search Report received in European Patent Application No. 18738529.9 dated Jul. 3, 2020, Applicant: Bristol-Myers Squibb Company, 7 pages.

File History of U.S. Appl. No. 16/476,814, filed Jul. 9, 2019, Inventors: Robert J. Johnston et al.

File History of U.S. Appl. No. 16/493,712, filed Sep. 12, 2019, Inventors: Robert J. Johnston et al.

File History of U.S. Appl. No. 16/982,277, filed Sep. 18, 2020, Inventors: Robert J. Johnston et al.

File History of U.S. Appl. No. 17/258,866, filed Jan. 8, 2021, Inventors: Robert J. Johnston et al.

File History of U.S. Appl. No. 17/695,081, filed Mar. 15, 2022, Inventors: Robert J. Johnston et al.

File History of U.S. Appl. No. 17/761,458, filed Mar. 17, 2022, Inventors: Lin Hui Su et al.

File History of U.S. Appl. No. 18/162,991, filed Feb. 1, 2023, Inventors: Robert J. Johnston et al.

GenBank AAA53000.1, immunoglobin heavy chain, partial, Jul. 26, 2016, 4 pages.

GenBank ABF83385.1, circulating B cell antibody heavy chain variable region, partial, Jul. 14, 2016, 4 pages.

Gonzales et al., "Minimizing the Immunogenicity of Antibodies for Clinical Application," Tumour Biol, 2005, 26(1):31-43.

International Search Report and Written Opinion for PCT/US2019/041154, dated Jan. 24, 2020, Applicant: Five Prime Therapeutics, Inc.; 21 pages.

International Search Report and Written Opinion for PCT/US2020/051421, dated Mar. 11, 2021, Applicant: Bristol-Myers Squibb Company, 30 pages.

International Search Report for PCT/US2018/013171, dated May 14, 2018, Applicant: Bristol-Myers Squibb Company, 16 pages.

International Search Report for PCT/US2018/022230, dated May 31, 2018, Applicant: Five Prime Therapeutics, Inc., 21 pages.

(56) References Cited

OTHER PUBLICATIONS

International Search Report for PCT/US2019/022895, dated Jul. 16, 2019, Applicant: Five Prime Therapeutics, Inc.; 14 pages.
Johnston et al., "Acidic pH Selective Binding of VISTA to PSGL-1 and Anti-Tumor Activity of Combined VISTA and PD-1 Blockade," Cancer Research, 2019, 70(13): supplement.
Johnston et al., "VISTA is an Acidic pH-Selective Ligand for PSGL-1," Nature, 2019, 574:565-588.
Krieg et al., "Functional Analysis of B and T Lymphocyte Attenuator engagement on CD4+ and CD8+ T Cells," J Immunology, 2005, 175(10):6420-6427.
Kunik et al, "Structural Consensus among Antibodies Defines the Antigen Binding Site," PLoS Comput Biol, 2012, 8(2):e1002388, 12 pages.
Lamminmaki et al., "Crystal Structure of a Recombinant Anti-estradiol Fab Fragment in Complex with 17β-Estradiol," J. Biol. Chem., 2001, 276(39): 36687-36694.
Le Mercier et al., "VISTA Regulates the Development of Protective Antitumor Immunity," Cancer Res., 2014, 74(7): 1933-1944.
Lenter et al., "Monospecific and Common Glycoprotein Ligands for E- and P-Selectin on Myeloid Cells," J. Cell Biol., 1994, 125(2):471-481.
Lines et al., "VISTA is a Novel Broad-Spectrum Negative Checkpoint Regulator for Cancer Immunotherapy," Cancer Immunol Res., 2014, 2(6):510-517.
Liu, "Pharmacokinetics of monoclonal antibodies and Fc-fusion proteins," Protein Cell, 2018, 9(1):15-32.
Lobo et al., "Antibody Pharmacokinetics and Pharmacodynamics". J Pharm Sci., 2004; 93(11):2645-68.
MacCallum et al., "Antibody-antigen Interactions: Contact Analysis and Binding Site Topography," J. Mol. Biol., 1996, 262:732-745.
Machine translation of RU2550262, May 10, 2015, Pigareva et al., 10 pages.
Mahoney et al., "Acidity Changes Immunology: A New VISTA Pathway," Nature Immunology, 2020, 21:13-16.
Mangsbo et al., "The Human Agonistic CD40 Antibody ADC-1013 Eradicates Bladder Tumors and Generates T-cell-Dependent Tumor Immunity," Clin Cancer Res, 2015, 21(5):1115-26.
Matsumoto et al., "P-Selectin Glycoprotein Ligand-1 Negatively Regulates T-Cell Immune Responses," J Immunol, 2009, 183:7204-7211.
Morris, "Epitope Mapping of Protein Antigens by Competition ELISA", The Protein Protocols Handbook, Totowa, NJ, Humana Press, 1996, pp. 595-600.
Padlan et al., "Structure of an antibody-antigen complex: Crystal Structure of the HyHEL-10 Fab-lysozyme complex," Proc. Natl. Acad. Sci. USA, 1989, 86:5938-5942.
PIR: S23628, Ig kappa chain V region—human (fragment), Jan. 21, 2000, 2 pages.
Rudikoff et al., "Single amino acid substitution altering antigen-binding specificity," Proc. Natl. Acad. Sci. USA, 1982, 79:1979-1983.
Supplementary Extended European Search Report received in European Patent Application No. 18767615.0 dated Apr. 29, 2021, 12 pages.
Tinoco et al., "PSGL-1 Is an Immune Checkpoint Regulator that Promotes T Cell Exhaustion," Immunity, 2016, 44:1190-1203.
Vajdos et al., "Comprehensive Functional Maps of the Antigen-binding Site of an Anti-ErbB2 Antibody Obtained with Shotgun Scanning of Mutagenesis," J. Mol. Biol., 2002, 320:415-428.
Wang et al., "VISTA, a novel mouse Ig superfamily ligand that negatively regulates T cell responses," J. Exp. Med., 2011, 208(3):577-592.
Wark et al., "Latest Technologies for the Enhancement of Antibody Affinity," Adv Drug Delivery Rev, 2006, 58 (5-6):657-670.
Wu et al., "Humanization of a Murine Monoclonal Antibody by Simultaneous Optimization of Framework and CDR Residues," J. Mol. Biol., 1999, 294:151-162.
Zhao et al., "Oncogenic Pathways that Affect Antitumor Immune Response and Immune Checkpoint Blockade Therapy," Pharmacology & Therapeutics, 2018, 181:76-84.
Zhu et al., "B7-H5 costimulates human T cells via CD28H," Nature Comm, 2013, 4:1-12.
English translation of Search Report received in Chinese Patent Application No. 201980020908.X, dated Mar. 11, 2025, 2 pages.
File History of U.S. Appl. No. 18/939,765, filed Nov. 7, 2024, Inventors: Robert J. Johnston et al., available on Patent Center.
Liu et al., "Clinical Diagnosis and Treatment of Infectious Diseases and Disease Control," Jilin Science and Technology Press, Mar. 31, 2018, 10 pages.
Lin et al., "Improved affinity of a chicken single-chain antibody to avian infectious bronchitis virus by site-directed mutagenesis of complementarity-determining region H3," African Journal of Biotechnology, 2011, 10(79):18294-18302.
Mariuzza et al., "The Structural Basis of Antigen-Antibody Recognition," Ann. Rev. Biophys. Chem., 1987, 16:139-59.
McCarthy et al., "Altering the fine specificity of an anti-Legionella single chain antibody by a single amino acid insertion," Journal of Immunological Methods, 2001, 251:137-149.
Machine Translation of CN110563843A, Dec. 13, 2019, 23 pages.
Machine Translation of WO 2019/078699, Apr. 25, 2019, 41 pages.

* cited by examiner

METHOD OF TREATING CANCER AND/OR INHIBITING BINDING OF PSGL-1 TO VISTA BY ADMINISTERING A PSGL-1 ANTIBODY OR A VISTA ANTIBODY

This application is a continuation of U.S. patent application Ser. No. 17/695,081 filed Mar. 15, 2022, which is a divisional of U.S. patent application Ser. No. 16/476,814, filed Jul. 9, 2019, now U.S. Pat. No. 11,306,150, which is a national stage application of International Patent Application No. PCT/US2018/013171, filed Jan. 10, 2018, which claims priority to U.S. Provisional Application No. 62/445,071 filed Jan. 11, 2017, each of which is incorporated in their entirety by reference herein.

TECHNICAL FIELD

Methods of identifying and using PSGL-1 antagonists are provided. Such methods include, but are not limited to, methods of treating cancer. PSGL-1 antagonists include, but are not limited to, antibodies that bind PSGL-1 and antibodies that bind VISTA, wherein the antibodies inhibit PSGL-1 binding to VISTA, e.g., at acidic pH (e.g., pH 6.0).

SEQUENCE LISTING

The present application contains a Sequence Listing which has been submitted electronically in XML format. Said XML copy, created on Dec. 14, 2023, is named "01275-0058-02US.xml" and is 22,616 bytes in size. The information in the electronic format of the sequence listing is incorporated herein by reference in its entirety.

BACKGROUND

V-region Immunoglobulin-containing Suppressor of T cell Activation (VISTA) is a cell surface-expressed protein that negatively regulates the activity of T cells (Wang et al., 2011, JEM 208(3) 577). VISTA is a single pass type-I transmembrane protein with a single extracellular IgV domain. Notably, the extracellular domain of VISTA bears homology to B7 family members such as PDL1, which also plays a role in modulating immune responses (Wang et al., 2011, JEM 208(3) 577). VISTA expression is restricted to hematopoietic cells and is present on monocytes, T cells and a fraction of dendritic cells (Wang et al., 2011, JEM 208(3) 577 & Flies et al., 2011, JI 187:1537). Treatment with VISTA: Ig in vitro suppresses proliferation and cytokine production by CD4+ T cells (Wang et al., 2011, JEM 208(3) 577). A VISTA specific monoclonal antibody can elicit enhanced T cell division in response to antigens presented by VISTA-expressing dendritic cells (Wang et al., 2011, JEM 208(3) 577). In vivo treatment of tumor-bearing animals with an anti-VISTA monoclonal antibody elicited an immune mediated anti-tumor response that inhibited tumor growth (Wang et al., 2011, JEM 208(3) 577). Collectively, these results highlight the importance of VISTA as a regulator of T cell-driven immune responses such as those observed during immune mediated tumor rejection. The cognate binding partner for VISTA is currently unknown.

Identification of binding partners for VISTA would assist in the understanding of VISTA-mediated inhibition of T-cell activation, and provide many advantages to drug development including selection of therapeutically effective and safe therapeutics, biomarkers for patient selection and companion diagnostics, targets for combination therapy, and new targets for developing cancer immunotherapeutic agents.

SUMMARY

In some embodiments, methods of identifying PSGL-1 antagonists are provided. In some embodiments, a method comprises contacting a candidate molecule with a VISTA molecule (e.g., a mature VISTA protein or a fragment thereof) and a PSGL-1 molecule (e.g., a mature PSGL-1 protein or fragment thereof), wherein the VISTA molecule comprises VISTA, a VISTA extracellular domain ("ECD"), or a VISTA ECD fusion molecule (e.g., excluding a signal sequence; i.e., a mature VISTA or fragment thereof), and the PSGL-1 molecule comprises PSGL-1, PSGL-1 ECD, or PSGL-1 ECD fusion molecule (e.g., excluding a signal sequence; i.e., a mature PSGL-1 or fragment thereof), wherein the contacting occurs in acidic pH, e.g., pH<7.0, ≤6.8, ≤6.5 or ≤6.3 or at pH 5.5 to 6.5, 6.0-6.5, 6.5-7.0 or 6.0-7.0, e.g., pH 6.0. In some embodiments, a method comprises forming a composition comprising a candidate molecule, a VISTA molecule, and PSGL-1 molecule, wherein the VISTA molecule comprises VISTA, a VISTA ECD, or a VISTA ECD fusion molecule, and the PSGL-1 molecule comprises PSGL-1, PSGL-1 ECD, or PSGL-1 ECD fusion molecule, e.g., at acidic pH, e.g., pH<7.0, ≤6.8, ≤6.5 or ≤6.3 or at pH 5.5 to 6.5, 6.0-6.5, 6.5-7.0 or 6.0-7.0, e.g., pH 6.0. In some embodiments, a method further comprises detecting binding of the VISTA molecule to the PSGL-1 molecule. In some embodiments, a reduction in the binding of the VISTA molecule to the PSGL-1 molecule in the presence of the candidate molecule as compared to the binding of the VISTA molecule to the PSGL-1 molecule in the absence of the candidate molecule indicates that the candidate molecule is PSGL-1 antagonist. In some embodiments, binding of the VISTA molecule to the PSGL-1 molecule is reduced by at least 30%, at least 40%, at least 50%, at least 60%, at least 70%, or at least 80% in the presence of the candidate molecule. In some embodiments, binding of the VISTA molecule to the PSGL-1 molecule is detected by a method selected from surface plasmon resonance, ELISA, amplified luminescent proximity homogeneous assay (ALPHA), and flow cytometry.

In any of the methods of identifying PSGL-1 antagonists described herein, the PSGL-1 antagonist may be an antibody that binds to VISTA, e.g., at acidic pH, e.g., pH<7.0, ≤6.8, ≤6.5 or ≤6.3 or at pH 5.5 to 6.5, 6.0-6.5, 6.5-7.0 or 6.0-7.0, e.g., pH 6.0. In any of the methods of identifying PSGL-1 antagonists described herein, the PSGL-1 antagonist may be an antibody that binds PSGL-1. In any of the methods of identifying PSGL-1 antagonists described herein, the PSGL-1 antagonist may be a small molecule. In any of the methods of identifying PSGL-1 antagonists described herein, the PSGL-1 antagonist may be a small peptide.

In some embodiments, methods of determining whether a VISTA antibody is PSGL-1 antagonist are provided. In some embodiments, a method comprises contacting the VISTA antibody with a VISTA molecule and PSGL-1 molecule, wherein the VISTA molecule comprises VISTA, a VISTA ECD, or a VISTA ECD fusion molecule, and the PSGL-1 molecule comprises PSGL-1, PSGL-1 ECD, or PSGL-1 ECD fusion molecule, e.g., at acidic pH, e.g., pH<7.0, ≤6.8, ≤6.5 or ≤6.3 or at pH 5.5 to 6.5, 6.0-6.5, 6.5-7.0 or 6.0-7.0, e.g., pH 6.0. In some embodiments, a method comprises forming a composition comprising the VISTA antibody, a VISTA molecule, and PSGL-1 molecule, wherein the VISTA molecule comprises VISTA, a VISTA ECD, or a VISTA ECD fusion molecule, and the PSGL-1 molecule comprises PSGL-1, PSGL-1 ECD, or PSGL-1 ECD fusion molecule, e.g., acidic pH, e.g., pH<7.0, ≤6.8, ≤6.5 or ≤6.3 or or at pH 5.5 to 6.5, 6.0-6.5, 6.5-7.0 or 6.0-7.0, e.g., pH 6.0. In some embodiments, a method further comprises detecting the binding of the VISTA molecule to the PSGL-1 molecule. In some embodiments, a reduction in the binding of the VISTA molecule to the PSGL-1 molecule in the presence of the VISTA antibody as compared to the binding of the VISTA molecule to the PSGL-1 molecule in the absence of the VISTA antibody indicates that the VISTA antibody is PSGL-1 antagonist. In some embodiments, binding of the VISTA molecule to the PSGL-1 molecule is reduced by at least 30%, at least 40%, at least 50%, at least 60%, at least 70%, or at least 80% in the presence of the VISTA antibody. In some embodiments, binding of the VISTA molecule to the PSGL-1 molecule is detected by a method selected from surface plasmon resonance, ELISA, amplified luminescent proximity homogeneous assay, and flow cytometry.

In any of the methods of identifying PSGL-1 antagonists described herein, the VISTA molecule may be VISTA expressed on the surface of a cell and/or the PSGL-1 molecule may be PSGL-1 expressed on the surface of a cell.

In some embodiments, methods of inhibiting binding of PSGL-1 to VISTA in a subject are provided. In some embodiments, a method comprise administering to the subject at least one PSGL-1 antagonist. In some embodiments, methods of inhibiting binding of PSGL-1 to VISTA on a cell are provided. In some embodiments, a method comprises contacting the cell with at least one PSGL-1 antagonist, e.g., at acidic pH, e.g., pH<7.0, ≤6.8, ≤6.5 or ≤6.3 or at pH 5.5 to 6.5, 6.0-6.5, 6.5-7.0 or 6.0-7.0, e.g., pH 6.0. In some embodiments, the cell is in vitro.

In some embodiments, methods of treating cancer are provided. In some embodiments, a method comprises administering to a subject with cancer an effective amount of at least one PSGL-1 antagonist. In some embodiments, the method further comprises administering to the subject an effective amount of a therapeutic agent selected from chemotherapeutic agents, anti-angiogenesis agents, growth inhibitory agents, immune-oncology agents, and anti-neoplastic compositions. In any of the embodiments described herein, PSGL-1 antagonist may block binding of PSGL-1 to VISTA.

In any of the embodiments described herein, a method may comprise administering a PSGL-1 antagonist selected from PSGL-1 antibody and a VISTA antibody, wherein the antibody inhibits binding of PSGL-1 to VISTA, e.g., at acidic pH, e.g., pH<7.0, ≤6.8, ≤6.5 or ≤6.3 or at pH 5.5 to 6.5, 6.0-6.5, 6.5-7.0 or 6.0-7.0, e.g., pH 6.0. In any of the embodiments described herein, a method may comprise administering a PSGL-1 antibody that inhibits binding of PSGL-1 to VISTA, e.g., at acidic pH, e.g., pH<7.0, ≤6.8, ≤6.5 or ≤6.3 or at pH 5.5 to 6.5, 6.0-6.5, 6.5-7.0 or 6.0-7.0, e.g., pH 6.0. In any of the embodiments described herein, an antibody may be selected from a chimeric antibody, a humanized antibody, and a human antibody. In any of the embodiments described herein, an antibody may be an antibody fragment. In some embodiments, the antibody fragment is selected from an IgG (e.g., IgG1, IgG2 or IgG4), Fv, a single-chain Fv (scFv), a Fab, a Fab', and a $(Fab')_2$.

In some embodiments, uses of PSGL-1 antagonists for treating cancer in subjects are provided. In any of the uses described herein, the PSGL-1 antagonist may be a PSGL-1 antibody or a VISTA antibody, wherein the antibody inhibits binding of PSGL-1 to VISTA, e.g., at acidic pH, e.g., pH<7.0, ≤6.8, ≤6.5 or ≤6.3 or at pH 5.5 to 6.5, 6.0-6.5, 6.5-7.0 or 6.0-7.0, e.g., pH 6.0. In some embodiments, the antibody is selected from a chimeric antibody, a humanized antibody, and a human antibody. In some embodiments, the antibody is an antibody fragment. In some embodiments, the antibody fragment is selected from an IgG (e.g., IgG1, IgG2 or IgG4), Fv, a single-chain Fv (scFv), a Fab, a Fab', and a $(Fab')_2$.

Any embodiment described herein or any combination thereof applies to any and all methods of the invention described herein.

BRIEF DESCRIPTION OF THE FIGURES

FIG. 4B shows the binding of PSGL-1-Fc to 293T-hVISTA cells at pH 6.0 (dots/filled circles) and the lack of significant binding at pH 7.2 (filled squares), as well as the lack of binding at pH 6.0 and 7.2 of PSGL-1-Fc to 293T cells that do not express hVISTA (diamonds and triangles, respectively, partially hidden behind the squares). FIG. 4A provides the rough data supporting FIG. 4B, and showing binding of PSGL-1 to 293T-hVISTA cells at pH 6.0.

DETAILED DESCRIPTION

Figure 1:
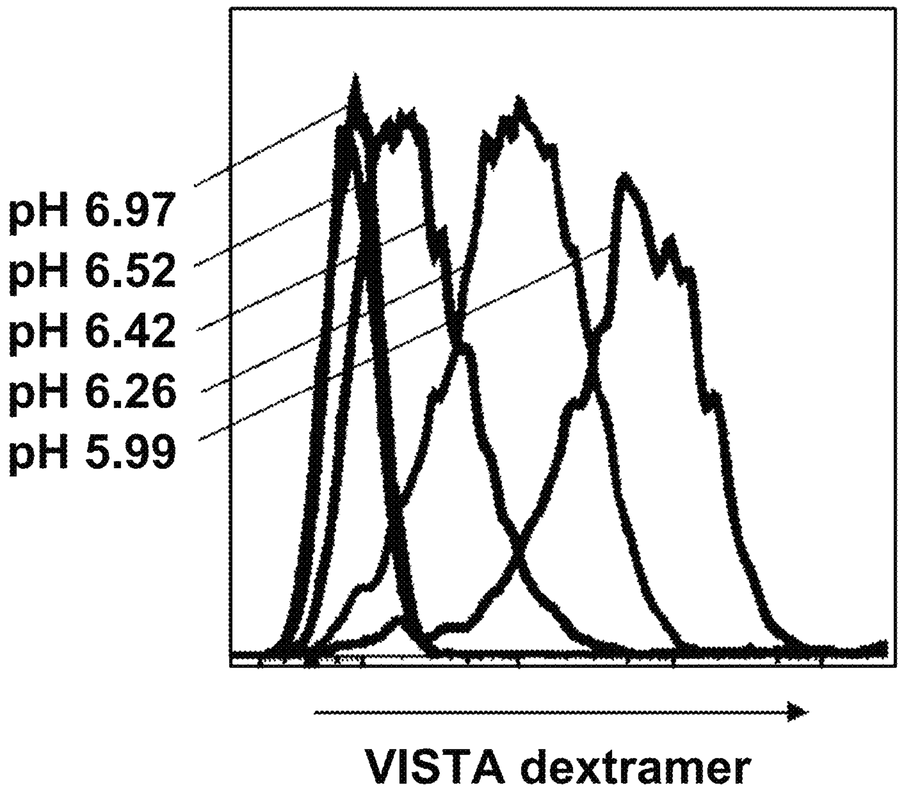
FIG. 1 shows flow cytometry results of VISTA Dextramer binding to T cells at various pH, showing enhanced binding at lower pH.

The present inventors have identified PSGL-1 as a binding partner for VISTA, wherein binding occurs preferentially in acidic pH. Targeting the interaction between VISTA and PSGL-1 may enhance the immune response to cancer cells by inhibiting the immune inhibitory effects of VISTA. Targeting molecules include antibodies that bind PSGL-1 and antibodies that bind VISTA, wherein the antibodies block the binding of VISTA to PSGL-1. Exemplary targeting molecules are molecules that bind to VISTA or PSGL-1 at acidic pH, e.g., at acidic pH, e.g., pH<7.0, ≤6.8, ≤6.5 or ≤6.3 or at pH 5.5 to 6.5, 6.0-6.5, 6.5-7.0 or 6.0-7.0, e.g., pH 6.0. Such targeting molecules are provided as therapeutic agents for treating cancer.

All references cited herein, including patent applications and publications, are incorporated by reference herein in their entirety.

The section headings used herein are for organizational purposes only and are not to be construed as limiting the subject matter described.

Definitions

Unless otherwise defined, scientific and technical terms used in connection with the present invention shall have the meanings that are commonly understood by those of ordinary skill in the art. Further, unless otherwise required by context, singular terms shall include pluralities and plural terms shall include the singular.

Exemplary techniques used in connection with recombinant DNA, oligonucleotide synthesis, tissue culture and transformation (e.g., electroporation, lipofection), enzymatic reactions, and purification techniques are known in the art. Many such techniques and procedures are described, e.g., in Sambrook et al. *Molecular Cloning: A Laboratory Manual* (3rd ed., Cold Spring Harbor Laboratory Press, Cold Spring Harbor, N.Y. (2001)), among other places. In addition, exemplary techniques for chemical syntheses, chemical analyses, pharmaceutical preparation, formulation, and delivery, and treatment of patients are also known in the art.

In this application, the use of "or" means "and/or" unless stated otherwise. In the context of a multiple dependent claim, the use of "or" refers back to more than one preceding independent or dependent claim in the alternative only. Unless otherwise indicated, the term "include" has the same meaning as "include, but are not limited to," the term "includes" has the same meaning as "includes, but is not limited to," and the term "including" has the same meaning as "including, but not limited to." Similarly, the term "such as" has the same meaning as the term "such as, but not limited to." Also, terms such as "element" or "component" encompass both elements and components comprising one unit and elements and components that comprise more than one subunit unless specifically stated otherwise.

As utilized in accordance with the present disclosure, the following terms, unless otherwise indicated, shall be understood to have the following meanings:

The terms "nucleic acid molecule" and "polynucleotide" may be used interchangeably, and refer to a polymer of nucleotides. Such polymers of nucleotides may contain natural and/or non-natural nucleotides, and include, but are not limited to, DNA, RNA, and PNA. "Nucleic acid sequence" refers to the linear sequence of nucleotides that comprise the nucleic acid molecule or polynucleotide.

The terms "polypeptide" refers to a polymer of amino acid residues, and are not limited to a minimum length. Such polymers of amino acid residues may contain natural or non-natural amino acid residues, and include, but are not limited to, peptides, oligopeptides, dimers, trimers, and multimers of amino acid residues. Both full-length proteins and fragments thereof are encompassed by the definition. The terms also include post-expression modifications of the polypeptide, for example, glycosylation, sialylation, acetylation, phosphorylation, and the like. Furthermore, for purposes of the present invention, a "polypeptide" refers to a protein that includes modifications, such as deletions, additions, and substitutions (generally conservative in nature), to the native sequence, as long as the protein maintains the desired activity. These modifications may be deliberate, as through site-directed mutagenesis, or may be accidental, such as through mutations of hosts that produce the proteins or errors due to PCR amplification. A "protein" includes polypeptides and complexes of 2 or more polypeptides, e.g., dimers and polymers. A "small peptide" refers to a peptide having 50 or fewer amino acids. In some embodiments, a small peptide has 40 or fewer, or 35 or fewer, or 30 or fewer, or 25 or fewer amino acids. In some embodiments, a small peptide has 10 to 50 amino acids or 15 to 30 amino acids.

A "native sequence" polypeptide comprises a polypeptide having the same amino acid sequence as a polypeptide found in nature. Thus, a native sequence polypeptide can have the amino acid sequence of naturally occurring polypeptide from any mammal. Such native sequence polypeptide can be isolated from nature or can be produced by recombinant or synthetic means. The term "native sequence" polypeptide specifically encompasses naturally occurring truncated or secreted forms of the polypeptide (e.g., an extracellular domain sequence), naturally occurring variant forms (e.g., alternatively spliced forms) and naturally occurring allelic variants of the polypeptide.

A polypeptide "variant" means a biologically active polypeptide having at least about 80% amino acid sequence identity with the native sequence polypeptide after aligning the sequences and introducing gaps, if necessary, to achieve the maximum percent sequence identity, and not considering any conservative substitutions as part of the sequence identity. Such variants include, for instance, polypeptides wherein one or more amino acid residues are added, or deleted, at the N- or C-terminus of the polypeptide. In some embodiments, a variant will have at least about 80% amino acid sequence identity. In some embodiment, a variant will have at least about 90% amino acid sequence identity. In some embodiment, a variant will have at least about 95% amino acid sequence identity with the native sequence polypeptide. In some embodiment, a variant will have at least about 97% amino acid sequence identity with the native sequence polypeptide.

As used herein, "Percent (%) amino acid sequence identity" and "homology" with respect to a peptide, polypeptide or antibody sequence are defined as the percentage of amino acid residues in a candidate sequence that are identical with the amino acid residues in the specific peptide or polypeptide sequence, after aligning the sequences and introducing gaps, if necessary, to achieve the maximum percent sequence identity, and not considering any conservative substitutions as part of the sequence identity. Alignment for purposes of determining percent amino acid sequence identity can be achieved in various ways that are within the skill in the art, for instance, using publicly available computer software such as BLAST, BLAST-2, ALIGN or MEGALIGN™ (DNASTAR) software. Those skilled in the art can determine appropriate parameters for measuring alignment, including any algorithms needed to achieve maximal alignment over the full length of the sequences being compared.

The terms "P-Selectin Glycoprotein Ligand 1" and "PSGL-1" are used interchangeably to refer to a native, PSGL-1 unless otherwise indicated. Thus, reference to PSGL-1 has the same meaning as reference to human PSGL-1 throughout the text, unless the context clarifies otherwise (e.g. by discussing non-human, or murine or cynomolgus PSGL-1). A non-human PSGL-1 may be from any vertebrate source, including mammals such as primates (e.g. cynomolgus monkeys) and rodents (e.g., mice and rats).

The term PSGL-1 includes full-length, unprocessed PSGL-1 as well as any form of PSGL-1 that results from processing in the cell or any fragment thereof that retains the ability to specifically bind VISTA, e.g., with an affinity (Kd) of less than ≤1 μM, ≤100 nM, or ≤10 nM. The term also encompasses naturally occurring variants of PSGL-1, e.g., splice variants or allelic variants. In some embodiments, PSGL-1 comprises the amino acid sequence of SEQ ID NO: 1 (human isoform 1 precursor, with signal peptide) or SEQ ID NO: 2 (human isoform 1 mature, without signal peptide) or the amino acid sequence of SEQ ID NO: 14 (human isoform 2 precursor, with signal peptide) or SEQ ID NO: 15 (human isoform 2 mature, without signal peptide).

The term "PSGL-1" also includes full-length PSGL-1, PSGL-1 fragments, and PSGL-1 variants, with or without a signal peptide. The term "full-length PSGL-1", as used herein, refers to full-length, unprocessed PSGL-1 as well as any form of PSGL-1 that results from processing in the cell or any fragment thereof that retains the ability to specifically bind VISTA, e.g., with an affinity (Kd) of less than ≤1 μM, ≤100 nM, or ≤10 nM. In some embodiments, a full-length PSGL-1 has the amino acid sequence of SEQ ID NO: 1 (isoform 1 precursor, with signal peptide) or SEQ ID NO: 2 (isoform 1 mature, without signal peptide) or SEQ ID NO: 14 (isoform 2 precursor, with signal peptide) or SEQ ID NO: 15 (isoform 2 mature, without signal peptide). As used herein, the term "PSGL-1 fragment" refers to PSGL-1 having one or more residues deleted from the N- and/or C-terminus of the full-length PSGL-1 and that retains the ability to bind VISTA. The PSGL-1 fragment may or may not include an N-terminal signal peptide. As used herein, the term "PSGL-1 variant" refers to PSGL-1 that contains amino acid additions, deletions, and substitutions and that remain capable of binding to VISTA. Such variants may be at least 80%, 85%, 90%, 92%, 95%, 97%, 98%, or 99% identical to the parent PSGL-1. The % identity of two polypeptides can be measured by a similarity score determined by comparing the amino acid sequences of the two polypeptides using the Bestfit program with the default settings for determining similarity. Bestfit uses the local homology algorithm of Smith and Waterman, Advances in Applied Mathematics 2:482-489 (1981) to find the best segment of similarity between two sequences.

The terms "V-domain Ig Suppressor of T cell Activation," "platelet receptor Gi24 isoform 1 precursor," "B7H5," and "VISTA" refer herein to a native, human VISTA unless specified otherwise. Thus, the expressions "VISTA" and "human VISTA" have the same meaning unless the context clarifies otherwise (e.g. by referring specifically to a non-human VISTA species). If the VISTA is non-human, it may be from any vertebrate source, including mammals such as primates (e.g. cynomolgus monkeys) and rodents (e.g., mice and rats). The term includes full-length, unprocessed VISTA as well as any form of VISTA that results from processing in the cell or any fragment thereof that retains the ability to specifically bind PSGL-1, e.g., with an affinity (Kd) of less than ≤1 μM, ≤100 nM, or ≤10 nM. The term also encompasses naturally occurring variants of VISTA, e.g., splice variants or allelic variants. In some embodiments, VISTA comprises the amino acid sequence of SEQ ID NO: 5 (precursor, with signal peptide) or SEQ ID NO: 6 (mature, without signal peptide). A nonlimiting exemplary non-human VISTA is mouse VISTA, which has the amino acid sequence of SEQ ID NO: 7 (precursor, with signal peptide) or SEQ ID NO: 8 (mature, without signal peptide).

The term "antagonist" is used in the broadest sense, and includes any molecule that partially or fully inhibits or neutralizes a biological activity of a polypeptide, such as PSGL-1 or VISTA, or that partially or fully inhibits the transcription or translation of a nucleic acid encoding the polypeptide. Exemplary antagonist molecules include, but are not limited to, antagonist antibodies, small peptides, oligopeptides, organic molecules (including small molecules), aptamers, and antisense nucleic acids. In some embodiments, an antagonist agent may be referred to as a blocking agent (such as a blocking antibody).

The term "PSGL-1 antagonist" refers to a molecule that interacts with PSGL-1 or VISTA and inhibits PSGL-1 and/or VISTA-mediated signaling. Exemplary PSGL-1 antagonists include antibodies that bind PSGL-1 and antibodies that bind VISTA. In some embodiments, PSGL-1 antagonist is an antibody to PSGL-1. In some embodiments, PSGL-1 antagonist blocks binding of PSGL-1 to VISTA.

A PSGL-1 antagonist is considered to "block binding of PSGL-1 to VISTA" when it reduces the amount of detectable binding of PSGL-1 to VISTA by at least 50%. In some embodiments, a PSGL-1 antagonist reduces the amount of detectable binding of PSGL-1 to VISTA by at least 60%, at least 70%, at least 80%, or at least 90%. In some such embodiments, the antagonist is said to block ligand binding by at least 50%, at least 60%, at least 70%, etc.

The terms "inhibition" or "inhibit" refer to a decrease or cessation of any phenotypic characteristic or to the decrease or cessation in the incidence, degree, or likelihood of that characteristic. In some embodiments, by "reduce" or "inhibit" is meant the ability to cause a decrease of 20% or greater. In another embodiment, by "reduce" or "inhibit" is meant the ability to cause a decrease of 50% or greater. In yet another embodiment, by "reduce" or "inhibit" is meant the ability to cause an overall decrease of 75%, 85%, 90%, 95%, or greater.

The term "PSGL-1 antibody" or "antibody that binds PSGL-1," as used herein, refers to an antibody that binds to PSGL-1, e.g. at acidic pH, e.g., pH<7.0, ≤6.8, ≤6.5 or ≤6.3 or or at pH 5.5 to 6.5, 6.0-6.5, 6.5-7.0 or 6.0-7.0, e.g., pH 6.0. In some embodiments, PSGL-1 antibody inhibits PSGL-1 and/or VISTA-mediated signaling. In some embodiments, PSGL-1 antibody blocks binding of PSGL-1 to VISTA, e.g., at acidic pH, e.g., pH<7.0, ≤6.8, ≤6.5 or ≤6.3 or at pH 5.5 to 6.5, 6.0-6.5, 6.5-7.0 or 6.0-7.0, e.g., pH 6.0. In some embodiments, PSGL-1 antibody refers to an antibody that is capable of binding PSGL-1 with sufficient affinity such that the antibody is useful as a diagnostic and/or therapeutic agent in targeting PSGL-1. In some embodiments, the extent of binding of PSGL-1 antibody to an unrelated, non-PSGL-1 protein is less than about 10% of the binding of the antibody to PSGL-1 as measured, e.g., by a radioimmunoassay (RIA). In some embodiments, PSGL-1 antibody binds to an epitope of PSGL-1 that is conserved among PSGL-1 from different species. In some embodiments, PSGL-1 antibody binds to the same epitope as a human or humanized PSGL-1 antibody that binds PSGL-1.

The term "VISTA antibody" or "antibody that binds VISTA," as used herein, refers to an antibody that binds to VISTA, e.g., at acidic pH, e.g., pH<7.0, ≤6.8, ≤6.5 or ≤6.3 or a pH 6.0-6.5, 6.5-7.0 or 6.0-7.0. In some embodiments, a VISTA antibody inhibits PSGL-1 and/or VISTA-mediated signaling. In some embodiments, a VISTA antibody blocks binding of PSGL-1 to VISTA, as defined above, e.g., at acidic pH, e.g., pH<7.0, ≤6.8, ≤6.5 or ≤6.3 or at pH 5.5 to 6.5, 6.0-6.5, 6.5-7.0 or 6.0-7.0, e.g., pH 6.0. Thus, in some embodiments, a VISTA antibody is PSGL-1 antagonist. In some embodiments, a VISTA antibody refers to an antibody that is capable of binding VISTA with sufficient affinity such that the antibody is useful as a diagnostic and/or therapeutic agent in targeting VISTA. In some embodiments, the extent of binding of a VISTA antibody to an unrelated, non-VISTA protein is less than about 10% of the binding of the antibody to VISTA as measured, e.g., by a radioimmunoassay (RIA). In some embodiments, a VISTA antibody binds to an epitope of VISTA that is conserved among VISTA from different species. In some embodiments, a VISTA antibody binds to the same epitope as a human or humanized VISTA antibody that binds human VISTA.

The term "antibody" herein is used in the broadest sense and encompasses various antibody structures, including but not limited to monoclonal antibodies, polyclonal antibodies, multispecific antibodies (e.g., bispecific antibodies), and antibody fragments so long as they exhibit the desired antigen-binding activity. The term "antibody" as used herein further refers to a molecule comprising complementarity-determining region (CDR) 1, CDR2, and CDR3 of a heavy chain and CDR1, CDR2, and CDR3 of a light chain, wherein the molecule is capable of binding to antigen. The term antibody includes, but is not limited to, fragments that are capable of binding antigen, such as Fv, single-chain Fv (scFv), Fab, Fab', and $(Fab')_2$. The term antibody also includes, but is not limited to, chimeric antibodies, humanized antibodies, and antibodies of various species such as mouse, human, cynomolgus monkey, etc.

In some embodiments, an antibody comprises a heavy chain variable region and a light chain variable region. In some embodiments, an antibody comprises at least one heavy chain comprising a heavy chain variable region and at least a portion of a heavy chain constant region, and at least one light chain comprising a light chain variable region and at least a portion of a light chain constant region. In some embodiments, an antibody comprises two heavy chains, wherein each heavy chain comprises a heavy chain variable region and at least a portion of a heavy chain constant region, and two light chains, wherein each light chain comprises a light chain variable region and at least a portion of a light chain constant region. As used herein, a single-chain Fv (scFv), or any other antibody that comprises, for example, a single polypeptide chain comprising all six CDRs (three heavy chain CDRs and three light chain CDRs) is considered to have a heavy chain and a light chain. In some such embodiments, the heavy chain is the region of the antibody that comprises the three heavy chain CDRs and the light chain in the region of the antibody that comprises the three light chain CDRs.

The term "heavy chain variable region" as used herein refers to a region comprising heavy chain CDR1, framework (FR) 2, CDR2, FR3, and CDR3. In some embodiments, a heavy chain variable region also comprises at least a portion of an FR1, which is N-terminal to CDR1, and/or at least a portion of an FR4, which is C-terminal to CDR3.

The term "heavy chain constant region" as used herein refers to a region comprising at least three heavy chain constant domains, $C_H1$, $C_H2$, and $C_H3$. Nonlimiting exemplary heavy chain constant regions include γ, δ, and α. Nonlimiting exemplary heavy chain constant regions also include ε and μ. Each heavy constant region corresponds to an antibody isotype. For example, an antibody comprising a γ constant region is an IgG antibody, an antibody comprising a δ constant region is an IgD antibody, and an antibody comprising an α constant region is an IgA antibody. Further, an antibody comprising a μ constant region is an IgM antibody, and an antibody comprising an & constant region is an IgE antibody. Certain isotypes can be further subdivided into subclasses. For example, IgG antibodies include, but are not limited to, IgG1 (comprising a $\gamma_1$ constant region), IgG2 (comprising a $\gamma_2$ constant region), IgG3 (comprising a $\gamma_3$ constant region), and IgG4 (comprising a $\gamma_4$ constant region) antibodies; IgA antibodies include, but are not limited to, IgA1 (comprising an $\alpha_1$ constant region) and IgA2 (comprising an $\alpha_2$ constant region) antibodies; and IgM antibodies include, but are not limited to, IgM1 and IgM2.

The term "heavy chain" as used herein refers to a polypeptide comprising at least a heavy chain variable region, with or without a leader sequence. In some embodiments, a heavy chain comprises at least a portion of a heavy chain constant region. The term "full-length heavy chain" as used herein refers to a polypeptide comprising a heavy chain variable region and a heavy chain constant region, with or without a leader sequence, and with or without a C-terminal lysine.

The term "light chain variable region" as used herein refers to a region comprising light chain CDR1, framework (FR) 2, CDR2, FR3, and CDR3. In some embodiments, a light chain variable region also comprises an FR1 and/or an FR4.

The term "light chain constant region" as used herein refers to a region comprising a light chain constant domain, $C_L$. Nonlimiting exemplary light chain constant regions include λ and κ.

The term "light chain" as used herein refers to a polypeptide comprising at least a light chain variable region, with or without a leader sequence. In some embodiments, a light chain comprises at least a portion of a light chain constant region. The term "full-length light chain" as used herein refers to a polypeptide comprising a light chain variable region and a light chain constant region, with or without a leader sequence.

An "antibody that binds to the same epitope" as a reference antibody as determined by an antibody competition assay, refers to an antibody that blocks binding of the reference antibody to its antigen in a competition assay by 50% or more, and conversely, the reference antibody blocks binding of the antibody to its antigen in a competition assay by 50% or more. The term "compete" when used in the context of an antibody that compete for the same epitope means competition between antibodies is determined by an assay in which an antibody being tested prevents or inhibits specific binding of a reference antibody to a common antigen (e.g., PSGL-1 or VISTA). Numerous types of competitive binding assays can be used, for example: solid phase direct or indirect radioimmunoassay (RIA), solid phase direct or indirect enzyme immunoassay (EIA), sandwich competition assay (see, e.g., Stahli et al., 1983, *Methods in Enzymology* 9:242-253); solid phase direct biotin-avidin EIA (see, e.g., Kirkland et al., 1986, *J. Immunol.* 137:3614-3619) solid phase direct labeled assay, solid phase direct labeled sandwich assay (see, e.g., Harlow and Lane, 1988, Antibodies, A Laboratory Manual, Cold Spring Harbor Press); solid phase direct label RIA using 1-125 label (see, e.g., Morel et al., 1988, *Molec. Immunol.* 25:7-15); solid phase direct biotin-avidin EIA (see, e.g., Cheung, et al., 1990, *Virology* 176:546-552); and direct labeled RIA (Moldenhauer et al., 1990, *Scand. J. Immunol.* 32:77-82). Typically, such an assay involves the use of purified antigen bound to a solid surface or cells bearing either of these, an unlabeled test antigen binding protein and a labeled reference antibody. Competitive inhibition is measured by determining the amount of label bound to the solid surface or cells in the presence of the test antibody. Usually the test antibody is present in excess. Antibodies identified by competition assay (competing antibodies) include antibodies binding to the same epitope as the reference antibodies and antibodies binding to an adjacent epitope sufficiently proximal to the epitope bound by the reference antibody for steric hindrance to occur. In some embodiments, when a competing antibody is present in excess, it will inhibit specific binding of a reference antibody to a common antigen by at least 40%, 45%, 50%, 55%, 60%, 65%, 70% or 75%. In some instance, binding is inhibited by at least 80%, 85%, 90%, 95%, or 97% or more.

The term "antigen" refers to a molecule or a portion of a molecule capable of being bound by a selective binding agent, such as an antibody or immunologically functional fragment thereof, and additionally capable of being used in a mammal to produce antibodies capable of binding to that antigen. An antigen may possess one or more epitopes that are capable of interacting with antibodies.

The term "epitope" is the portion of a molecule that is bound by a selective binding agent, such as an antibody or a fragment thereof. The term includes any determinant capable of specifically binding to an antibody. An epitope can be contiguous or non-contiguous (e.g., in a polypeptide, amino acid residues that are not contiguous to one another in the polypeptide sequence but that within in context of the molecule are bound by the antigen binding protein). In some embodiments, epitopes may be mimetic in that they comprise a three dimensional structure that is similar to an epitope used to generate the antibody, yet comprise none or only some of the amino acid residues found in that epitope used to generate the antibody. Epitope determinants may include chemically active surface groupings of molecules such as amino acids, sugar side chains, phosphoryl or sulfonyl groups, and may have specific three dimensional structural characteristics, and/or specific charge characteristics. In some embodiments, an "epitope" is defined by the method used to determine it. For example, in some embodiments, an antibody binds to the same epitope as a reference antibody, if they bind to the same region of the antigen, as determined by hydrogen-deuterium exchange (HDX). In certain embodiments, an antibody binds to the same epitope as a reference antibody if they bind to the same region of the antigen, as determined by X-ray crystallography.

A "chimeric antibody" as used herein refers to an antibody comprising at least one variable region from a first species (such as mouse, rat, cynomolgus monkey, etc.) and at least one constant region from a second species (such as human, cynomolgus monkey, chicken, etc.). In some embodiments, a chimeric antibody comprises at least one mouse variable region and at least one human constant region. In some embodiments, a chimeric antibody comprises at least one cynomolgus variable region and at least one human constant region. In some embodiments, all of the variable regions of a chimeric antibody are from a first species and all of the constant regions of the chimeric antibody are from a second species.

A "humanized antibody" as used herein refers to an antibody in which at least one amino acid in a framework region of a non-human variable region (such as mouse, rat, cynomolgus monkey, chicken, etc.) has been replaced with the corresponding amino acid from a human variable region. In some embodiments, a humanized antibody comprises at least one human constant region or fragment thereof. In some embodiments, a humanized antibody is an Fab, an scFv, a $(Fab')_2$, etc.

A "CDR-grafted antibody" as used herein refers to a humanized antibody in which one or more complementarity determining regions (CDRs) of a first (non-human) species have been grafted onto the framework regions (FRs) of a second (human) species.

A "human antibody" as used herein refers to antibodies produced in humans, antibodies produced in non-human animals that comprise human immunoglobulin genes, such as XenoMouse®, and antibodies selected using in vitro methods, such as phage display, wherein the antibody repertoire is based on a human immunoglobulin sequences.

The term "PSGL-1 extracellular domain" ("PSGL-1 ECD") includes full-length PSGL-1 ECDs, PSGL-1 ECD fragments, and PSGL-1 ECD variants, and refers to PSGL-1 polypeptide that lacks the intracellular and transmembrane domains, with or without a signal peptide. The PSGL-1 ECD polypeptide is a native, human ECD unless specified otherwise. The term "full-length PSGL-1 ECD", as used herein, refers to PSGL-1 ECD that extends to the last amino acid of the extracellular domain, and may or may not include an N-terminal signal peptide, and includes natural splice variants in the extracellular domain. A non-limiting exemplary PSGL-1 ECD comprises amino acids 1 to 241 of SEQ ID NO: 1 (with signal sequence), or amino acids 23 to 241 of SEQ ID NO: 1 (without signal sequence), amino acids 1 to 219 of SEQ ID NO: 2), SEQ ID NO: 3, or SEQ ID NO: 4. Another exemplary PSGL-1 ECD comprises amino acids 1 to 241 of SEQ ID NO: 14 (with signal sequence), or amino acids 23 to 241 of SEQ ID NO: 14 (without signal sequence), or amino acids 1 to 219 of SEQ ID NO: 15, SEQ ID NO: 16, or SEQ ID NO: 17, or SEQ ID NO: 18. As used herein, the term "PSGL-1 ECD fragment" refers to PSGL-1 ECD having one or more residues deleted from the N- and/or C-terminus of the full-length ECD and that retains the ability to bind VISTA. The PSGL-1 ECD fragment may or may not include an N-terminal signal peptide. As used herein, the term "PSGL-1 ECD variants" refers to PSGL-1 ECDs that contain amino acid additions, deletions, and substitutions and that remain capable of binding to VISTA. Such variants may be at least 80%, 85%, 90%, 92%, 95%, 97%, 98%, or 99% identical to the parent PSGL-1 ECD. The % identity of two polypeptides can be measured by a similarity score determined by comparing the amino acid sequences of the two polypeptides using the Bestfit program with the default settings for determining similarity. Bestfit uses the local homology algorithm of Smith and Waterman, Advances in Applied Mathematics 2:482-489 (1981) to find the best segment of similarity between two sequences.

The term "PSGL-1 ECD fusion molecule" refers to a molecule comprising PSGL-1 ECD, and one or more "fusion partners." In some embodiment, the PSGL-1 ECD and the fusion partner are covalently linked ("fused"). If the fusion partner is also a polypeptide ("the fusion partner polypeptide"), the PSGL-1 ECD and the fusion partner polypeptide may be part of a continuous amino acid sequence, and the fusion partner polypeptide may be linked to either the N-terminus or the C-terminus of the PSGL-1 ECD. In such cases, the PSGL-1 ECD and the fusion partner polypeptide may be translated as a single polypeptide from a coding sequence that encodes both the PSGL-1 ECD and the fusion partner polypeptide (the "PSGL-1 ECD fusion protein"). In some embodiments, the PSGL-1 ECD and the fusion partner are covalently linked through other means, such as, for example, a chemical linkage other than a peptide bond. Many known methods of covalently linking polypeptides to other molecules (for example, fusion partners) may be used. In other embodiments, the PSGL-1 ECD and the fusion partner may be fused through a "linker," which is comprised of at least one amino acid or chemical moiety. SEQ ID NO: 19 provides a linker used in a PSGL-1 Fc fusion molecule of the examples herein. A nonlimiting exemplary PSGL-1 ECD fusion molecule comprises a fusion molecule described in T. Pouyani et al., Cel/83: 333-343 (1995). Nonlimiting exemplary PSGL-1 ECD fusion molecules may comprise a PSGL-1 ECD in combination with an Fc such as a combination of (a) amino acids 1 to 241 of SEQ ID NO: 1 (with signal sequence), or amino acids 23 to 241 of SEQ ID NO: 1 (without signal sequence), amino acids 1 to 219 of SEQ ID NO: 2), SEQ ID NO: 3, or SEQ ID NO: 4, or amino acids 1 to 241 of SEQ ID NO: 14 (with signal sequence), or amino acids 23 to 241 of SEQ ID NO: 14 (without signal sequence), or amino acids 1 to 219 of SEQ ID NO: 15, SEQ ID NO: 16, or SEQ ID NO: 17, or SEQ ID NO: 18; with (b) an Fc, such as an Fc of SEQ ID NO: 11, 12, or 13, or an Fc domain from a human IgG1.

In some embodiments, the PSGL-1 polypeptide and the fusion partner are noncovalently linked. In some such embodiments, they may be linked, for example, using binding pairs. Exemplary binding pairs include, but are not limited to, biotin and avidin or streptavidin, an antibody and its antigen, etc.

Exemplary fusion partners include, but are not limited to, an immunoglobulin Fc domain, albumin, and polyethylene glycol. The amino acid sequences of nonlimiting exemplary Fc domains are shown in SEQ ID NOs: 11 to 13.

As noted above, a PSGL-1 ECD is derived from a native, human PSGL-1 sequence unless specified otherwise. In some embodiments, however, PSGL-1 ECD amino acid sequence is derived from that of a non-human mammal. In such embodiments, the non-human PSGL-1 ECD amino acid sequence may be derived from mammals including, but not limited to, rodents (including mice, rats, hamsters), rabbits, simians, felines, canines, equines, bovines, porcines, ovines, caprines, mammalian laboratory animals, mammalian farm animals, mammalian sport animals, and mammalian pets. PSGL-1 ECD fusion molecules incorporating a non-humPSGL-1 ECD are termed "non-humPSGL-1 ECD fusion molecules" or "non-human PSGL-1 ECD fusion molecules." Similar to human PSGL-1 ECD fusion molecules, non-human fusion molecules may comprise a fusion partner, optional linker, and a non-human PSGL-1 ECD. Such non-human fusion molecules may also include a signal peptide.

A "PSGL-1 ECD fragment" refers to a PSGL-1 ECD having one or more residues deleted from the N- and/or C-terminus of a full-length, human ECD and that retains the ability to bind to human VISTA. A "non-humPSGL-1 ECD fragment" refers to a non-humPSGL-1 ECD having one or more residues deleted from the N- and/or C-terminus of the full-length ECD and that retains the ability to bind to VISTA of the non-human animal from which the sequence was derived. This is in contrast to a "PSGL-1 ECD variant," refers to a PSGL-1 ECD that contain amino acid additions, deletions, and substitutions compared to a native, human PSGL-1 ECD and that remain capable of binding to human VISTA.

A "non-humPSGL-1 ECD variant" refers to non-human PSGL-1 ECDs that contain amino acid additions, deletions, and substitutions and that remain capable of binding to VISTA from the animal from which the sequence was derived. This is in contrast to a "PSGL-1 ECD variant," which refers to a human PSGL-1 ECD that contains amino acid additions, deletions, and substitutions and that remains capable of binding to human VISTA.

In any of the embodiments described herein, PSGL-1, including but not limited to, full-length PSGL-1, PSGL-1 fragments, PSGL-1 variants, PSGL-1 ECDs, and PSGL-1 ECD fusion proteins, may further comprise a tag. Nonlimiting exemplary tags include FITC, $His_6$, biotin, and other labels and tags known in the art.

The term "VISTA extracellular domain" ("VISTA ECD") includes full-length VISTA ECDs, VISTA ECD fragments, and VISTA ECD variants, and refers to a VISTA polypeptide that lacks the intracellular and transmembrane domains, with or without a signal peptide. The polypeptide is a native, human ECD unless specified otherwise. The term "full-length VISTA ECD", as used herein, refers to a VISTA ECD that extends to the last amino acid of the extracellular domain, and may or may not include an N-terminal signal peptide, and includes natural splice variants in the extracellular domain.

As used herein, the term "VISTA ECD fragment" refers to a VISTA ECD having one or more residues deleted from the N- and/or C-terminus of the full-length ECD and that retains the ability to bind PSGL-1. The VISTA ECD fragment may or may not include an N-terminal signal peptide. As used herein, the term "VISTA ECD variants" refers to VISTA ECDs that contain amino acid additions, deletions, and substitutions and that remain capable of binding to PSGL-1. Such variants may be at least 80%, 85%, 90%, 92%, 95%, 97%, 98%, or 99% identical to the parent VISTA ECD.

The % identity of two polypeptides can be measured by a similarity score determined by comparing the amino acid sequences of the two polypeptides using the Bestfit program with the default settings for determining similarity. Bestfit uses the local homology algorithm of Smith and Waterman, Advances in Applied Mathematics 2:482-489 (1981) to find the best segment of similarity between two sequences. In some embodiments, a VISTA ECD comprising a His tag has the amino acid sequence of SEQ ID NO: 10. In some embodiments, a VISTA ECD without a His tag has the amino acid sequence of amino acids 1-202 of SEQ ID NO: 10 (corresponding to the full sequence of SEQ ID NO: 10 minus the last six His residues of that sequence).

The term "VISTA ECD fusion molecule" refers to a molecule comprising a VISTA ECD, and one or more "fusion partners." In some embodiment, the VISTA ECD and the fusion partner are covalently linked ("fused"). If the fusion partner is also a polypeptide ("the fusion partner polypeptide"), the VISTA ECD and the fusion partner polypeptide may be part of a continuous amino acid sequence, and the fusion partner polypeptide may be linked to either the N-terminus or the C-terminus of the VISTA ECD. In such cases, the VISTA ECD and the fusion partner polypeptide may be translated as a single polypeptide from a coding sequence that encodes both the VISTA ECD and the fusion partner polypeptide (the "VISTA ECD fusion protein"). In some embodiments, the VISTA ECD and the fusion partner are covalently linked through other means, such as, for example, a chemical linkage other than a peptide bond. Many known methods of covalently linking polypeptides to other molecules (for example, fusion partners) may be used. In other embodiments, the VISTA ECD and the fusion partner may be fused through a "linker," which is comprised of at least one amino acid or chemical moiety. A nonlimiting exemplary VISTA ECD fusion molecule comprises the sequence of SEQ ID NO: 9. Another exemplary VISTA ECD fusion molecule comprises the sequence of amino acids 1-202 of SEQ ID NO: 10 plus an Fc sequence of SEQ ID NOs: 11, 12, or 13.

In some embodiments, the VISTA polypeptide and the fusion partner are noncovalently linked. In some such embodiments, they may be linked, for example, using binding pairs. Exemplary binding pairs include, but are not limited to, biotin and avidin or streptavidin, an antibody and its antigen, etc.

Exemplary fusion partners include, but are not limited to, an immunoglobulin Fc domain, albumin, and polyethylene glycol. The amino acid sequences of nonlimiting exemplary Fc domains are shown in SEQ ID NOs: 11 to 13.

Again, unless specified otherwise, a VISTA ECD amino acid sequence is derived from that of a human. In some embodiments, however, a VISTA ECD amino acid sequence is derived from that of a non-human mammal. In such embodiments, the VISTA ECD amino acid sequence may be derived from mammals including, but not limited to, rodents (including mice, rats, hamsters), rabbits, simians, felines, canines, equines, bovines, porcines, ovines, caprines, mammalian laboratory animals, mammalian farm animals, mammalian sport animals, and mammalian pets. VISTA ECD fusion molecules incorporating a non-human VISTA ECD are termed "non-human VISTA ECD fusion molecules." Similar to the human VISTA ECD fusion molecules, non-human fusion molecules may comprise a fusion partner, optional linker, and a VISTA ECD. Such non-human fusion molecules may also include a signal peptide. A "VISTA ECD fragment" in contrast, refers to a native, VISTA ECD having one or more residues deleted from the N- and/or C-terminus of a full-length human ECD and that retains the ability to bind to human PSGL-1.

A "non-human VISTA ECD fragment" refers to a non-human VISTA ECD having one or more residues deleted from the N- and/or C-terminus of the full-length ECD and that retains the ability to bind to PSGL-1 of the non-human animal from which the sequence was derived. A "VISTA ECD variant" in contrast, refers to VISTA ECDs that contain amino acid additions, deletions, and substitutions compared to native, human VISTA ECD and that remain capable of binding to human PSGL-1. A "non-human VISTA ECD variant" refers to VISTA ECDs that contain amino acid additions, deletions, and substitutions compared to their parent VISTA ECD and that remain capable of binding to PSGL-1 from the animal from which the sequence was derived.

In any of the embodiments described herein, VISTA, including but not limited to, full-length VISTA, VISTA fragments, VISTA variants, VISTA ECDs, and VISTA ECD fusion proteins, may further comprise a tag. Nonlimiting exemplary tags include FITC, $His_6$, biotin, and other labels and tags known in the art.

The term "signal peptide" refers to a sequence of amino acid residues located at the N-terminus of a polypeptide that facilitates secretion of a polypeptide from a mammalian cell. A signal peptide may be cleaved upon export of the polypeptide from the mammalian cell, forming a mature protein. Signal peptides may be natural or synthetic, and they may be heterologous or homologous to the protein to which they are attached. Exemplary signal peptides include, but are not limited to, the signal peptides of PSGL-1 and VISTA. Exemplary signal peptides also include signal peptides from heterologous proteins. A "signal sequence" refers to a polynucleotide sequence that encodes a signal peptide.

The term "vector" is used to describe a polynucleotide that may be engineered to contain a cloned polynucleotide or polynucleotides that may be propagated in a host cell. A vector may include one or more of the following elements: an origin of replication, one or more regulatory sequences (such as, for example, promoters and/or enhancers) that regulate the expression of the polypeptide of interest, and/or one or more selectable marker genes (such as, for example, antibiotic resistance genes and genes that may be used in colorimetric assays, e.g., β-galactosidase). The term "expression vector" refers to a vector that is used to express a polypeptide of interest in a host cell.

A "host cell" refers to a cell that may be or has been a recipient of a vector or isolated polynucleotide. Host cells may be prokaryotic cells or eukaryotic cells. Exemplary eukaryotic cells include mammalian cells, such as primate or non-primate animal cells; fungal cells, such as yeast; plant cells; and insect cells. Nonlimiting exemplary mammalian cells include, but are not limited to, NSO cells, PER.C6 cells (Crucell), and 293 and CHO cells, and their derivatives, such as 293-6E and DG44 cells, respectively.

The term "isolated" as used herein refers to a molecule that has been separated from at least some of the components with which it is typically found in nature or has been separated from at least some of the components with which it is typically produced. For example, a polypeptide is referred to as "isolated" when it is separated from at least some of the components of the cell in which it was produced. Where a polypeptide is secreted by a cell after expression, physically separating the supernatant containing the polypeptide from the cell that produced it is considered to be "isolating" the polypeptide. Similarly, a polynucleotide is referred to as "isolated" when it is not part of the larger polynucleotide (such as, for example, genomic DNA or mitochondrial DNA, in the case of a DNA polynucleotide) in which it is typically found in nature, or is separated from at least some of the components of the cell in which it was produced, e.g., in the case of an RNA polynucleotide. Thus, a DNA polynucleotide that is contained in a vector inside a host cell may be referred to as "isolated" so long as that polynucleotide is not found in that vector in nature.

The terms "subject" and "patient" are used interchangeably herein to refer to a human. In some embodiments, methods of treating other mammals, including, but not limited to, rodents, simians, felines, canines, equines, bovines, porcines, ovines, caprines, mammalian laboratory animals, mammalian farm animals, mammalian sport animals, and mammalian pets, are also provided. In some instances, a "subject" or "patient" refers to a subject or patient in need of treatment for a disease or disorder.

The term "sample" or "patient sample" as used herein, refers to material that is obtained or derived from a subject of interest that contains a cellular and/or other molecular entity that is to be characterized and/or identified, for example based on physical, biochemical, chemical and/or physiological characteristics. For example, the phrase "disease sample" and variations thereof refers to any sample obtained from a subject of interest that would be expected or is known to contain the cellular and/or molecular entity that is to be characterized. By "tissue or cell sample" is meant a collection of similar cells obtained from a tissue of a subject or patient. The source of the tissue or cell sample may be solid tissue as from a fresh, frozen and/or preserved organ or tissue sample or biopsy or aspirate; blood or any blood constituents; bodily fluids such as sputum, cerebral spinal fluid, amniotic fluid, peritoneal fluid, or interstitial fluid; cells from any time in gestation or development of the subject. The tissue sample may also be primary or cultured cells or cell lines. Optionally, the tissue or cell sample is obtained from a disease tissue/organ. The tissue sample may contain compounds which are not naturally intermixed with the tissue in nature such as preservatives, anticoagulants, buffers, fixatives, nutrients, antibiotics, or the like.

A "reference sample", "reference cell", or "reference tissue", as used herein, refers to a sample, cell or tissue obtained from a source known, or believed, not to be afflicted with the disease or condition for which a method or composition of the invention is being used to identify. In one embodiment, a reference sample, reference cell or reference tissue is obtained from a healthy part of the body of the same subject or patient in whom a disease or condition is being identified using a composition or method of the invention. In one embodiment, a reference sample, reference cell or reference tissue is obtained from a healthy part of the body of at least one individual who is not the subject or patient in whom a disease or condition is being identified using a composition or method of the invention. In some embodiments, a reference sample, reference cell or reference tissue was previously obtained from a patient prior to developing a disease or condition or at an earlier stage of the disease or condition.

A condition "has previously been characterized as having [a characteristic]" when such characteristic of the condition has been shown in at least a subset of patients with the condition, or in one or more animal models of the condition. In some embodiments, such characteristic of the condition does not have to be determined in the patient to be treated one or more PSGL-1 antagonists of the present invention. The presence of the characteristic in a specific patient who is to be treated using the present methods and/or compositions need not have been determined in order for the patient to be considered as having a condition that has previously been characterized as having the characteristic.

A "disorder" or "disease" is any condition that would benefit from treatment with one or more PSGL-1 antagonists of the invention. This includes chronic and acute disorders or diseases including those pathological conditions that predispose the mammal to the disorder in question. Non-limiting examples of disorders to be treated herein include cancers.

The term "cancer" is used herein to refer to a group of cells that exhibit abnormally high levels of proliferation and growth. A cancer may be benign (also referred to as a benign tumor), pre-malignant, or malignant. Cancer cells may be solid cancer cells (i.e., forming solid tumors) or leukemic cancer cells. The term "cancer growth" is used herein to refer to proliferation or growth by a cell or cells that comprise a cancer that leads to a corresponding increase in the size or extent of the cancer.

Examples of cancer include but are not limited to, carcinoma, lymphoma, blastoma, sarcoma, and leukemia. More particular nonlimiting examples of such cancers include squamous cell cancer, small-cell lung cancer, pituitary cancer, esophageal cancer, astrocytoma, soft tissue sarcoma, non-small cell lung cancer, adenocarcinoma of the lung, squamous carcinoma of the lung, cancer of the peritoneum, hepatocellular cancer, gastrointestinal cancer, pancreatic cancer, glioblastoma, cervical cancer, ovarian cancer, liver cancer, bladder cancer, hepatoma, breast cancer, colon cancer, colorectal cancer, endometrial or uterine carcinoma, salivary gland carcinoma, kidney cancer, renal cancer, liver cancer, prostate cancer, vulval cancer, thyroid cancer, hepatic carcinoma, brain cancer, endometrial cancer, testis cancer, cholangiocarcinoma, gallbladder carcinoma, gastric cancer, melanoma, and various types of head and neck cancer.

A "chemotherapeutic agent" is a chemical compound useful in the treatment of cancer. Examples of chemotherapeutic agents include, but are not limited to, alkylating agents such as thiotepa and Cytoxan cyclosphosphamide; alkyl sulfonates such as busulfan, improsulfan and piposulfan; aziridines such as benzodopa, carboquone, meturedopa, and uredopa; ethylenimines and methylamelamines including altretamine, triethylenemelamine, trietylenephosphoramide, triethiylenethiophosphoramide and trimethylolomelamine; acetogenins (especially bullatacin and bullatacinone); a camptothecin (including the synthetic analogue topotecan); bryostatin; callystatin; CC-1065 (including its adozelesin, carzelesin and bizelesin synthetic analogues); cryptophycins (particularly cryptophycin 1 and cryptophycin 8); dolastatin; duocarmycin (including the synthetic analogues, KW-2189 and CB1-TM1); eleutherobin; pancratistatin; a sarcodictyin; spongistatin; nitrogen mustards such as chlorambucil, chlornaphazine, cholophosphamide, estramustine, ifosfamide, mechlorethamine, mechlorethamine oxide hydrochloride, melphalan, novembichin, phenesterine, prednimustine, trofosfamide, uracil mustard; nitrosureas such as carmustine, chlorozotocin, fotemustine, lomustine, nimustine, and ranimnustine; antibiotics such as the enediyne antibiotics (e.g., calicheamicin, especially calicheamicin gammaI1 and calicheamicin omegaI1 (see, e.g., Agnew, *Chem Intl. Ed. Engl.,* 33: 183-186 (1994)); dynemicin, including dynemicin A; bisphosphonates, such as clodronate; an esperamicin; as well as neocarzinostatin chromophore and related chromoprotein enediyne antiobiotic chromophores), aclacinomysins, actinomycin, authramycin, azaserine, bleomycins, cactinomycin, carabicin, carminomycin, carzinophilin, chromomycinis, dactinomycin, daunorubicin, detorubicin, 6-diazo-5-oxo-L-norleucine, Adriamycin® doxorubicin (including morpholino-doxorubicin, cyanomorpholino-doxorubicin, 2-pyrrolino-doxorubicin and deoxydoxorubicin), epirubicin, esorubicin, idarubicin, marcellomycin, mitomycins such as mitomycin C, mycophenolic acid, nogalamycin, olivomycins, peplomycin, potfiromycin, puromycin, quelamycin, rodorubicin, streptonigrin, streptozocin, tubercidin, ubenimex, zinostatin, zorubicin; anti-metabolites such as methotrexate and 5-fluorouracil (5-FU); folic acid analogues such as denopterin, methotrexate, pteropterin, trimetrexate; purine analogs such as fludarabine, 6-mercaptopurine, thiamiprine, thioguanine; pyrimidine analogs such as ancitabine, azacitidine, 6-azauridine, carmofur, cytarabine, dideoxyuridine, doxifluridine, enocitabine, floxuridine; androgens such as calusterone, dromostanolone propionate, epitiostanol, mepitiostane, testolactone; anti-adrenals such as aminoglutethimide, mitotane, trilostane; folic acid replenisher such as frolinic acid; aceglatone; aldophosphamide glycoside; aminolevulinic acid; eniluracil; amsacrine; bestrabucil; bisantrene; edatraxate; defofamine; demecolcine; diaziquone; elfornithine; elliptinium acetate; an epothilone; etoglucid; gallium nitrate; hydroxyurea; lentinan; lonidainine; maytansinoids such as maytansine and ansamitocins; mitoguazone; mitoxantrone; mopidanmol; nitraerine; pentostatin; phenamet; pirarubicin; losoxantrone; podophyllinic acid; 2-ethylhydrazide; procarbazine; PSKR polysaccharide complex (JHS Natural Products, Eugene, OR); razoxane; rhizoxin; sizofiran; spirogermanium; tenuazonic acid; triaziquone; 2,2',2"-trichlorotriethylamine; trichothecenes (especially T-2 toxin, verracurin A, roridin A and anguidine); urethan; vindesine; dacarbazine; mannomustine; mitobronitol; mitolactol; pipobroman; gacytosine; arabinoside ("Ara-C"); cyclophosphamide; thiotepa; taxoids, e.g., Taxol® paclitaxel (Bristol-Myers Squibb Oncology, Princeton, N.J.), Abraxane® Cremophor-free, albumin-engineered nanoparticle formulation of paclitaxel (American Pharmaceutical Partners, Schaumberg, Illinois), and Taxotere® doxetaxel (Rhône-Poulenc Rorer, Antony, France); chloranbucil; GemzarR gemcitabine; 6-thioguanine; mercaptopurine; methotrexate; platinum analogs such as cisplatin, oxaliplatin and carboplatin; vinblastine; platinum; etoposide (VP-16); ifosfamide; mitoxantrone; vincristine; Navelbine® vinorelbine; novantrone; teniposide; edatrexate; daunomycin; aminopterin; xeloda; ibandronate; irinotecan (Camptosar, CPT-11) (including the treatment regimen of irinotecan with 5-FU and leucovorin); topoisomerase inhibitor RFS 2000; difluorometlhylornithine (DMFO); retinoids such as retinoic acid; capecitabine; combretastatin; leucovorin (LV); oxaliplatin, including the oxaliplatin treatment regimen (FOLFOX); inhibitors of PKC-alpha, Raf, H-Ras, EGFR (e.g., erlotinib (Tarceva®)) and VEGF-A that reduce cell proliferation and pharmaceutically acceptable salts, acids or derivatives of any of the above.

Further nonlimiting exemplary chemotherapeutic agents include anti-hormonal agents that act to regulate or inhibit hormone action on cancers such as anti-estrogens and selective estrogen receptor modulators (SERMs), including, for example, tamoxifen (including Nolvadex® tamoxifen), raloxifene, droloxifene, 4-hydroxytamoxifen, trioxifene, keoxifene, LY117018, onapristone, and FarestonR toremifene; aromatase inhibitors that inhibit the enzyme aromatase, which regulates estrogen production in the adrenal glands, such as, for example, 4(5)-imidazoles, aminoglutethimide, Megase® megestrol acetate, Aromasin® exemestane, formestanie, fadrozole, Rivisor® vorozole, Femara® letrozole, and Arimidex® anastrozole; and anti-androgens such as flutamide, nilutamide, bicalutamide, leuprolide, and goserelin; as well as troxacitabine (a 1,3-dioxolane nucleoside cytosine analog); antisense oligonucleotides, particularly those which inhibit expression of genes in signaling pathways implicated in abherant cell proliferation, such as, for example, PKC-alpha, Ralf and H-Ras; ribozymes such as a VEGF expression inhibitor (e.g., Angiozyme® ribozyme) and a HER2 expression inhibitor; vaccines such as gene therapy vaccines, for example, Allovectin® vaccine, Leuvectin® vaccine, and Vaxid® vaccine; Proleukin® rIL-2; Lurtotecan® topoisomerase 1 inhibitor; Abarelix® rmRH; and pharmaceutically acceptable salts, acids or derivatives of any of the above.

An “anti-angiogenesis agent” or “angiogenesis inhibitor” refers to a small molecular weight substance, a polynucleotide (including, e.g., an inhibitory RNA (RNAi or siRNA)), a polypeptide, an isolated protein, a recombinant protein, an antibody, or conjugates or fusion proteins thereof, that inhibits angiogenesis, vasculogenesis, or undesirable vascular permeability, either directly or indirectly. It should be understood that the anti-angiogenesis agent includes those agents that bind and block the angiogenic activity of the angiogenic factor or its receptor. For example, an anti-angiogenesis agent is an antibody or other antagonist to an angiogenic agent, e.g., antibodies to VEGF-A (e.g., bevacizumab (Avastin®)) or to the VEGF-A receptor (e.g., KDR receptor or Flt-1 receptor), anti-PDGFR inhibitors such as Gleevec® (Imatinib Mesylate), small molecules that block VEGF receptor signaling (e.g., PTK787/ZK2284, SU6668, Sutent®/SU11248 (sunitinib malate), AMG706, or those described in, e.g., international patent application WO 2004/113304). Anti-angiogensis agents also include native angiogenesis inhibitors, e.g., angiostatin, endostatin, etc. See, e.g., Klagsbrun and D’Amore (1991) *Annu. Rev. Physiol.* 53:217-39; Streit and Detmar (2003) *Oncogene* 22:3172-3179 (e.g., Table 3 listing anti-angiogenic therapy in malignant melanoma); Ferrara & Alitalo (1999) *Nature Medicine* 5(12): 1359-1364; Tonini et al. (2003) *Oncogene* 22:6549-6556 (e.g., Table 2 listing known anti-angiogenic factors); and, Sato (2003) *Int. J. Clin. Oncol.* 8:200-206 (e.g., Table 1 listing anti-angiogenic agents used in clinical trials).

A “growth inhibitory agent” as used herein refers to a compound or composition that inhibits growth of a cell (such as a cell expressing VEGF) either in vitro or in vivo. Thus, the growth inhibitory agent may be one that significantly reduces the percentage of cells (such as a cell expressing VEGF) in S phase. Examples of growth inhibitory agents include, but are not limited to, agents that block cell cycle progression (at a place other than S phase), such as agents that induce G1 arrest and M-phase arrest. Classical M-phase blockers include the vincas (vincristine and vinblastine), taxanes, and topoisomerase II inhibitors such as doxorubicin, epirubicin, daunorubicin, etoposide, and bleomycin. Those agents that arrest G1 also spill over into S-phase arrest, for example, DNA alkylating agents such as tamoxifen, prednisone, dacarbazine, mechlorethamine, cisplatin, methotrexate, 5-fluorouracil, and ara-C. Further information can be found in Mendelsohn and Israel, eds., *The Molecular Basis of Cancer*, Chapter 1, entitled “Cell cycle regulation, oncogenes, and antineoplastic drugs” by Murakami et al. (W. B. Saunders, Philadelphia, 1995), e.g., p. 13. The taxanes (paclitaxel and docetaxel) are anticancer drugs both derived from the yew tree. Docetaxel (Taxotere®, Rhone-Poulenc Rorer), derived from the European yew, is a semisynthetic analogue of paclitaxel (Taxol®, Bristol-Myers Squibb). Paclitaxel and docetaxel promote the assembly of microtubules from tubulin dimers and stabilize microtubules by preventing depolymerization, which results in the inhibition of mitosis in cells.

The term “anti-neoplastic composition” refers to a composition useful in treating cancer comprising at least one active therapeutic agent. Examples of therapeutic agents include, but are not limited to, e.g., chemotherapeutic agents, growth inhibitory agents, cytotoxic agents, agents used in radiation therapy, anti-angiogenesis agents, cancer immunotherapeutic agents (also referred to as immuno-oncology agents), apoptotic agents, anti-tubulin agents, and other-agents to treat cancer, such as anti-HER-2 antibodies, anti-CD20 antibodies, an epidermal growth factor receptor (EGFR) antagonist (e.g., a tyrosine kinase inhibitor), HER1/EGFR inhibitor (e.g., erlotinib (Tarceva®), platelet derived growth factor inhibitors (e.g., Gleevec® (Imatinib Mesylate)), a COX-2 inhibitor (e.g., celecoxib), interferons, CTLA4 inhibitors (e.g., anti-CTLA antibody ipilimumab (YERVOY®)), PD-1 inhibitors (e.g., anti-PD1 antibodies, BMS-936558), PDL1 inhibitors (e.g., anti-PDL1 antibodies, MPDL3280A), PDL2 inhibitors (e.g., anti-PDL2 antibodies), VISTA inhibitors (e.g., anti-VISTA antibodies), cytokines, antagonists (e.g., neutralizing antibodies) that bind to one or more of the following targets ErbB2, ErbB3, ErbB4, PDGFR-beta, BlyS, APRIL, BCMA, PD-1, PDL1, PDL2, CTLA4, VISTA, or VEGF receptor(s), TRAIL/Apo2, and other bioactive and organic chemical agents, etc. Combinations thereof are also included in the invention.

“Treatment,” as used herein, refers to therapeutic treatment, for example, wherein the object is to slow down (lessen) the targeted pathologic condition or disorder as well as, for example, wherein the object is to inhibit recurrence of the condition or disorder. “Treatment,” as used herein, covers any administration or application of a therapeutic for a disease (also referred to herein as a “disorder” or a “condition”) in a mammal, including a human, and includes inhibiting the disease or progression of the disease, inhibiting or slowing the disease or its progression, arresting its development, partially or fully relieving the disease, partially or fully relieving one or more symptoms of a disease, or restoring or repairing a lost, missing, or defective function; or stimulating an inefficient process. The term “treatment” also includes reducing the severity of any phenotypic characteristic and/or reducing the incidence, degree, or likelihood of that characteristic. Those in need of treatment include those already with the disorder as well as those at risk of recurrence of the disorder or those in whom a recurrence of the disorder is to be prevented or slowed down.

The term “effective amount” or “therapeutically effective amount” refers to an amount of a drug effective to treat a disease or disorder in a subject. In some embodiments, an effective amount refers to an amount effective, at dosages and for periods of time necessary, to achieve the desired therapeutic or prophylactic result. A therapeutically effective amount of PSGL-1 antagonist of the invention may vary according to factors such as the disease state, age, sex, and weight of the individual, and the ability of the antagonist to elicit a desired response in the individual. A therapeutically effective amount encompasses an amount in which any toxic or detrimental effects of PSGL-1 antagonist are outweighed by the therapeutically beneficial effects.

A "prophylactically effective amount" refers to an amount effective, at dosages and for periods of time necessary, to achieve the desired prophylactic result. Typically, but not necessarily, since a prophylactic dose is used in subjects prior to or at an earlier stage of disease, the prophylactically effective amount would be less than the therapeutically effective amount.

A "pharmaceutically acceptable carrier" refers to a non-toxic solid, semisolid, or liquid filler, diluent, encapsulating material, formulation auxiliary, or carrier conventional in the art for use with a therapeutic agent that together comprise a "pharmaceutical composition" for administration to a subject. A pharmaceutically acceptable carrier is non-toxic to recipients at the dosages and concentrations employed and is compatible with other ingredients of the formulation. The pharmaceutically acceptable carrier is appropriate for the formulation employed. For example, if the therapeutic agent is to be administered orally, the carrier may be a gel capsule. If the therapeutic agent is to be administered subcutaneously, the carrier ideally is not irritable to the skin and does not cause injection site reaction.

An "article of manufacture" is any manufacture (e.g., a package or container) or kit comprising at least one reagent, e.g., a medicament for treatment of a disease or disorder, or a probe for specifically detecting a biomarker described herein. In some embodiments, the manufacture or kit is promoted, distributed, or sold as a unit for performing the methods described herein.

Therapeutic Compositions and Methods

Methods of Treating Diseases

PSGL-1 antagonists are provided for use in methods of treating humans and other mammals. Methods of treating a disease comprising administering PSGL-1 antagonists to humans and other mammals are provided.

Methods of Treating Cancer

In some embodiments, methods for treating or preventing a cancer are provided, comprising administering an effective amount of PSGL-1 antagonist to a subject in need of such treatment.

The present inventors have identified PSGL-1 as a binding partner for VISTA. VISTA is a receptor on the surface of various immune cells (such as T cells, dendritic cells, natural killer cells, monocytes, and macrophages) that serves as an inhibitor of active immune responses. Expression of PSGL-1 and/or VISTA on the surface of cancer and/or immune cells (e.g., T cells and NK cells) cells may inhibit immune responses by engaging PSGL-1 and/or VISTA on immune cells. Inhibition of the VISTA-PSGL-1 interaction may enhance immune-mediated killing of cancer cells.

In some embodiments, methods of treating cancer are provided, wherein the methods comprise administering PSGL-1 antagonist to a subject with cancer. In some embodiments, use of PSGL-1 antagonist for treating cancer is provided. Nonlimiting exemplary cancers that may be treated with PSGL-1 antagonists are provided herein, including carcinoma, lymphoma, blastoma, sarcoma, and leukemia. More particular non-limiting examples of such cancers include squamous cell cancer, small-cell lung cancer, pituitary cancer, esophageal cancer, astrocytoma, soft tissue sarcoma, non-small cell lung cancer, adenocarcinoma of the lung, squamous carcinoma of the lung, cancer of the peritoneum, hepatocellular cancer, gastrointestinal cancer, pancreatic cancer, glioblastoma, cervical cancer, ovarian cancer, liver cancer, bladder cancer, hepatoma, breast cancer, colon cancer, colorectal cancer, endometrial or uterine carcinoma, salivary gland carcinoma, kidney cancer, renal cancer, liver cancer, prostate cancer, vulval cancer, thyroid cancer, hepatic carcinoma, brain cancer, endometrial cancer, testis cancer, cholangiocarcinoma, gallbladder carcinoma, gastric cancer, melanoma, and various types of head and neck cancer. In some embodiments, lung cancer is non-small cell lung cancer or lung squamous cell carcinoma. In some embodiments, leukemia is acute myeloid leukemia or chronic lymphocytic leukemia. In some embodiments, breast cancer is breast invasive carcinoma. In some embodiments, ovarian cancer is ovarian serous cystadenocarcinoma. In some embodiments, kidney cancer is kidney renal clear cell carcinoma. In some embodiments, colon cancer is colon adenocarcinoma. In some embodiments, bladder cancer is bladder urothelial carcinoma.

In some embodiments, the PSGL-1 antagonist is selected from a PSGL-1 antibody and a VISTA antibody. In some embodiments, the PSGL-1 antagonist is a PSGL-1 antibody. A PSGL-1 antagonist for treating cancer may also be a non-antibody protein, such as PSGL-1 or VISTA or a portion thereof (e.g., the ECD) that inhibits the interaction between PSGL-1 and VISTA, optionally further comprising a fusion partner and in the form of a fusion molecule. Various exemplary PSGL-1 antagonists are described in more detail in the sections that follow.

Routes of Administration and Carriers

In various embodiments, PSGL-1 antagonists may be administered subcutaneously or intravenously. In some embodiments, PSGL-1 antagonist may be administered in vivo by various routes, including, but not limited to, oral, intra-arterial, parenteral, intranasal, intramuscular, intracardiac, intraventricular, intratracheal, buccal, rectal, intraperitoneal, by inhalation, intradermal, topical, transdermal, and intrathecal, or otherwise, e.g., by implantation. The subject compositions may be formulated into preparations in solid, semi-solid, liquid, or gaseous forms; including, but not limited to, tablets, capsules, powders, granules, ointments, solutions, suppositories, enemas, injections, inhalants, and aerosols. In some embodiments, PSGL-1 antagonist is delivered using gene therapy. As a nonlimiting example, a nucleic acid molecule encoding PSGL-1 antagonist may be coated onto gold microparticles and delivered intradermally by a particle bombardment device, or "gene gun," e.g., as described in the literature (see, e.g., Tang et al., *Nature* 356:152-154 (1992)).

In various embodiments, compositions comprising PSGL-1 antagonist are provided in formulations with a wide variety of pharmaceutically acceptable carriers (see, e.g., Gennaro, *Remington: The Science and Practice of Pharmacy with Facts and Comparisons: Drugfacts Plus,* 20th ed. (2003); Ansel et al., *Pharmaceutical Dosage Forms and Drug Delivery Systems,* 7th ed., Lippencott Williams and Wilkins (2004); Kibbe et al., *Handbook of Pharmaceutical Excipients,* 3rd ed., Pharmaceutical Press (2000)). Various pharmaceutically acceptable carriers, which include vehicles, adjuvants, and diluents, are available. Moreover, various pharmaceutically acceptable auxiliary substances, such as pH adjusting and buffering agents, tonicity adjusting agents, stabilizers, wetting agents and the like, are also available. Nonlimiting exemplary carriers include saline, buffered saline, dextrose, water, glycerol, ethanol, and combinations thereof.

In various embodiments, compositions comprising PSGL-1 antagonist may be formulated for injection, including subcutaneous administration, by dissolving, suspending, or emulsifying them in an aqueous or nonaqueous solvent, such as vegetable or other oils, synthetic aliphatic acid glycerides, esters of higher aliphatic acids, or propylene glycol; and if desired, with conventional additives such as solubilizers, isotonic agents, suspending agents, emulsifying agents, stabilizers and preservatives. In various embodiments, the compositions may be formulated for inhalation, for example, using pressurized acceptable propellants such as dichlorodifluoromethane, propane, nitrogen, and the like. The compositions may also be formulated, in various embodiments, into sustained release microcapsules, such as with biodegradable or non-biodegradable polymers. A nonlimiting exemplary biodegradable formulation includes poly lactic acid-glycolic acid polymer. A nonlimiting exemplary non-biodegradable formulation includes a polyglycerin fatty acid ester. Certain methods of making such formulations are described, for example, in EP 1 125 584 A1.

Pharmaceutical dosage packs comprising one or more containers, each containing one or more doses of PSGL-1 antagonist, are also provided. In some embodiments, a unit dosage is provided wherein the unit dosage contains a predetermined amount of a composition comprising PSGL-1 antagonist, with or without one or more additional agents. In some embodiments, such a unit dosage is supplied in single-use prefilled syringe for injection. In various embodiments, the composition contained in the unit dosage may comprise saline, sucrose, or the like; a buffer, such as phosphate, or the like; and/or be formulated within a stable and effective pH range. Alternatively, in some embodiments, the composition may be provided as a lyophilized powder that may be reconstituted upon addition of an appropriate liquid, for example, sterile water. In some embodiments, the composition comprises one or more substances that inhibit protein aggregation, including, but not limited to, sucrose and arginine. In some embodiments, a composition of the invention comprises heparin and/or a proteoglycan.

Pharmaceutical compositions are administered in an amount effective for treatment or prophylaxis of the specific indication. The therapeutically effective amount is typically dependent on the weight of the subject being treated, his or her physical or health condition, the extensiveness of the condition to be treated, or the age of the subject being treated. In some embodiments, PSGL-1 antagonist may be administered in an amount in the range of about 50 μg/kg body weight to about 50 mg/kg body weight per dose. In some embodiments, PSGL-1 antagonist may be administered in an amount in the range of about 100 μg/kg body weight to about 50 mg/kg body weight per dose. In some embodiments, PSGL-1 antagonist may be administered in an amount in the range of about 100 μg/kg body weight to about 20 mg/kg body weight per dose. In some embodiments, PSGL-1 antagonist may be administered in an amount in the range of about 0.5 mg/kg body weight to about 20 mg/kg body weight per dose.

In some embodiments, PSGL-1 antagonist may be administered in an amount in the range of about 10 mg to about 1,000 mg per dose. In some embodiments, PSGL-1 may be administered in an amount in the range of about 20 mg to about 500 mg per dose. In some embodiments, PSGL-1 antagonist may be administered in an amount in the range of about 20 mg to about 300 mg per dose. In some embodiments, PSGL-1 antagonist may be administered in an amount in the range of about 20 mg to about 200 mg per dose.

The PSGL-1 antagonist compositions may be administered as needed to subjects. In some embodiments, an effective dose of PSGL-1 antagonist is administered to a subject one or more times. In various embodiments, an effective dose of PSGL-1 antagonist is administered to the subject once a month, less than once a month, such as, for example, every two months, every three months, or every six months. In other embodiments, an effective dose of PSGL-1 antagonist is administered more than once a month, such as, for example, every two weeks, every week, twice per week, three times per week, daily, or multiple times per day. An effective dose of PSGL-1 antagonist is administered to the subject at least once. In some embodiments, the effective dose of PSGL-1 antagonist may be administered multiple times, including for periods of at least a month, at least six months, or at least a year. In some embodiments, PSGL-1 antagonist is administered to a subject as-needed to alleviate one or more symptoms of a condition.

Combination Therapy

PSGL-1 antagonist according to the invention, including any functional fragments thereof, may be administered to a subject in need thereof in combination with other biologically active substances or other treatment procedures for the treatment of diseases. For example, PSGL-1 antagonists may be administered alone or with other modes of treatment. They may be provided before, substantially contemporaneous with, or after other modes of treatment, such as radiation therapy.

For treatment of cancer, the PSGL-1 antagonist may be administered in conjunction with one or more of anti-cancer agents, such as the chemotherapeutic agent, growth inhibitory agent, anti-angiogenesis agent or anti-neoplastic composition. Nonlimiting examples of chemotherapeutic agent, growth inhibitory agent, anti-angiogenesis agent and anti-neoplastic composition that can be used in combination with one or more PSGL-1 antagonists of the present invention are provided herein under "Definitions."

In certain embodiments, PSGL-1 antagonist that specifically binds to PSGL-1 (an "PSGL-1 binding antagonist"), e.g., PSGL-1 antagonist antibody, is administered with an antagonist that specifically binds to VISTA (a "VISTA binding antagonist"), e.g., a VISTA antagonist antibody, to a subject having a disease in which the stimulation of the immune system would be beneficial, e.g., cancer or infectious diseases. The two antagonists may be administered simultaneously or consecutively, e.g., as described below for the combination of PSGL-1 antagonist with an immuno-oncology agent. One or more additional therapeutics, e.g., checkpoint modulators may be added to a treatment with PSGL-1 binding antagonist and a VISTA binding antagonist, e.g., for cancer or infectious diseases.

In certain embodiments, PSGL-1 antagonist is administered with another treatment, either simultaneously, or consecutively, to a subject, e.g., a subject having cancer. For example, PSGL-1 antagonist may be administered with one of more of: radiotherapy, surgery, or chemotherapy, e.g., targeted chemotherapy or immunotherapy. Immunotherapy, e.g., cancer immuntherapy includes cancer vaccines and immuno-oncology agents. PSGL-1 antagonist may be, e.g., a protein, an antibody, antibody fragment or a small molecule, that binds to PSGL-1. PSGL-1 antagonist may be an antibody or antigen binding fragment thereof that specifically binds to PSGL-1. PSGL-1 antagonist may be, e.g., a protein, an antibody, antibody fragment or a small molecule, that binds to VISTA. PSGL-1 antagonist may be an antibody or antigen binding fragment thereof that specifically binds to VISTA.

In certain embodiments, a method of treatment of a subject having cancer comprises administering to the subject having the cancer PSGL-1 antagonist, e.g., PSGL-1 antibody or a VISTA antibody, and one or more immuno-oncology agents. Immunotherapy, e.g., therapy with an immuno-oncology agent, is effective to enhance, stimulate, and/or upregulate immune responses in a subject. In one aspect, the administration of PSGL-1 antagonist with an immuno-oncology agent has a synergic effect in the treatment of cancer, e.g., in inhibiting tumor growth.

For the description herein of combinations of PSGL-1 antagonist with another agent, e.g., an immuno-oncology agent, if PSGL-1 antagonist is PSGL-1 binding antagonist, then an immuno-oncology agent may be a VISTA binding antagonist, and if PSGL-1 antagonist is a VISTA binding antagonist, then an immuno-oncology agent may be PSGL-1 binding antagonist.

In one aspect, PSGL-1 antagonist is sequentially administered prior to administration of the immuno-oncology agent. In one aspect, PSGL-1 antagonist is administered concurrently with the immunology-oncology agent. In yet one aspect, PSGL-1 antagonist is sequentially administered after administration of the immuno-oncology agent. The administration of the two agents may start at times that are, e.g., 30 minutes, 60 minutes, 90 minutes, 120 minutes, 3 hours, 6 hours, 12 hours, 24 hours, 36 hours, 48 hours, 3 days, 5 days, 7 days, or one or more weeks apart, or administration of the second agent may start, e.g., 30 minutes, 60 minutes, 90 minutes, 120 minutes, 3 hours, 6 hours, 12 hours, 24 hours, 36 hours, 48 hours, 3 days, 5 days, 7 days, or one or more weeks after the first agent has been administered.

In certain aspects, PSGL-1 antagonist and an immuno-oncology agent are administered simultaneously, e.g., are infused simultaneously, e.g., over a period of 30 or 60 minutes, to a patient. PSGL-1 antagonist may be co-formulated with an immuno-oncology agent.

Immuno-oncology agents include, for example, a small molecule drug, antibody or fragment thereof, or other biologic or small molecule. Examples of biologic immuno-oncology agents include, but are not limited to, antibodies, antibody fragments, vaccines and cytokines. In one aspect, the antibody is a monoclonal antibody. In certain aspects, the monoclonal antibody is humanized or human antibody.

In one aspect, the immuno-oncology agent is (i) an agonist of a stimulatory (including a co-stimulatory) molecule (e.g., receptor or ligand) or (ii) an antagonist of an inhibitory (including a co-inhibitory) molecule (e.g., receptor or ligand) on immune cells, e.g., T cells, both of which result in amplifying antigen-specific T cell responses. In certain aspects, an immuno-oncology agent is (i) an agonist of a stimulatory (including a co-stimulatory) molecule (e.g., receptor or ligand) or (ii) an antagonist of an inhibitory (including a co-inhibitory) molecule (e.g., receptor or ligand) on cells involved in innate immunity, e.g., NK cells, and wherein the immuno-oncology agent enhances innate immunity. Such immuno-oncology agents are often referred to as immune checkpoint regulators, e.g., immune checkpoint inhibitor or immune checkpoint stimulator.

In certain embodiments, an immuno-oncology agent targets a stimulatory or inhibitory molecule that is a member of the immunoglobulin super family (IgSF). For example, an immuno-oncology agent may be an agent that targets (or binds specifically to) a member of the B7 family of membrane-bound ligands, which includes B7-1, B7-2, B7-H1 (PD-L1), B7-DC (PD-L2), B7-H2 (ICOS-L), B7-H3, B7-H4, B7-H5, and B7-H6, or a co-stimulatory or co-inhibitory receptor binding specifically to a B7 family member. An immuno-oncology agent may be an agent that targets a member of the TNF family of membrane bound ligands or a co-stimulatory or co-inhibitory receptor binding specifically thereto, e.g., a TNF receptor family member. Exemplary TNF and TNFR family members that may be targeted by immuno-oncology agents include CD40 and CD40L, OX-40, OX-40L, GITR, GITRL, CD70, CD27L, CD30, CD30L, 4-1BBL, CD137 (4-1BB), TRAIL/Apo2-L, TRAILR1/DR4, TRAILR2/DR5, TRAILR3, TRAILR4, OPG, RANK, RANKL, TWEAKR/Fn14, TWEAK, BAFFR, EDAR, XEDAR, TACI, APRIL, BCMA, LTBR, LIGHT, DcR3, HVEM, VEGI/TL1A, TRAMP/DR3, EDAR, EDA1, XEDAR, EDA2, TNFR1, Lymphotoxin $\alpha$/TNF$\beta$, TNFR2, TNF$\alpha$, LT$\beta$R, Lymphotoxin $\alpha$ 1$\beta$2, FAS, FASL, RELT, DR6, TROY and NGFR. An immuno-oncology agent that may be used in combination with PSGL-1 antagonist agent for treating cancer may be an agent, e.g., an antibody, targeting an IgSF member, such as a B7 family member, a B7 receptor family member, a TNF family member or a TNFR family member, such as those described above.

In one aspect, PSGL-1 antagonist is administered with one or more of (i) an antagonist of a protein that inhibits T cell activation (e.g., immune checkpoint inhibitor) such as CTLA-4, PD-1, PD-L1, PD-L2, LAG-3, TIM3, Galectin 9, CEACAM-1, BTLA, CD69, Galectin-1, TIGIT, CD113, GPR56, VISTA, B7-H3, B7-H4, 2B4, CD48, GARP, PD1H, LAIR1, TIM-1, TIM-4, and PSGL-1 and (ii) an agonist of a protein that stimulates T cell activation such as B7-1, B7-2, CD28, 4-1BB (CD137), 4-1BBL, ICOS, ICOS-L, OX40, OX40L, GITR, GITRL, CD70, CD27, CD40, CD40L, DR3 and CD28H.

In one aspect, an immuno-oncology agent is an agent that inhibits (i.e., an antagonist of) a cytokine that inhibits T cell activation (e.g., IL-6, IL-10, TGF-ß, VEGF, and other immunosuppressive cytokines) or is an agonist of a cytokine, such as IL-2, IL-7, IL-12, IL-15, IL-21 and IFN$\alpha$ (e.g., the cytokine itself) that stimulates T cell activation, and stimulates an immune response.

Other agents that can be combined with PSGL-1 antagonist for stimulating the immune system, e.g., for the treatment of cancer and infectious diseases, include antagonists of inhibitory receptors on NK cells or agonists of activating receptors on NK cells. For example, Anti-PSGL-1 antagonist can be combined with an antagonist of KIR.

Yet other agents for combination therapies include agents that inhibit or deplete macrophages or monocytes, including but not limited to CSF-1R antagonists such as CSF-1R antagonist antibodies including RG7155 (WO11/70024, WO11/107553, WO11/131407, WO13/87699, WO13/119716, WO13/132044) or FPA008 (WO11/140249; WO13169264; WO14/036357).

Immuno-oncology agents also include agents that inhibit TGF-ß signaling.

Additional agents that may be combined with PSGL-1 antagonist include agents that enhance tumor antigen presentation, e.g., dendritic cell vaccines, GM-CSF secreting cellular vaccines, CpG oligonucleotides, and imiquimod, or therapies that enhance the immunogenicity of tumor cells (e.g., anthracyclines).

Yet other therapies that may be combined with PSGL-1 antagonist include therapies that deplete or block Treg cells, e.g., an agent that specifically binds to CD25.

Another therapy that may be combined with PSGL-1 antagonist is a therapy that inhibits a metabolic enzyme such as indoleamine dioxigenase (IDO), dioxigenase, arginase, or nitric oxide synthetase.

Another class of agents that may be used includes agents that inhibit the formation of adenosine or inhibit the adenosine A2A receptor.

Other therapies that may be combined with PSGL-1 antagonist for treating cancer include therapies that reverse/prevent T cell anergy or exhaustion and therapies that trigger an innate immune activation and/or inflammation at a tumor site.

PSGL-1 antagonist may be combined with more than one immuno-oncology agent, and may be, e.g., combined with a combinatorial approach that targets multiple elements of the immune pathway, such as one or more of the following: a therapy that enhances tumor antigen presentation (e.g., dendritic cell vaccine, GM-CSF secreting cellular vaccines, CpG oligonucleotides, imiquimod); a therapy that inhibits negative immune regulation e.g., by inhibiting CTLA-4 and/or PD1/PD-L1/PD-L2 pathway and/or depleting or blocking Treg or other immune suppressing cells; a therapy that stimulates positive immune regulation, e.g., with agonists that stimulate the CD-137, OX-40 and/or GITR pathway and/or stimulate T cell effector function; a therapy that increases systemically the frequency of anti-tumor T cells; a therapy that depletes or inhibits Tregs, such as Tregs in the tumor, e.g., using an antagonist of CD25 (e.g., daclizumab) or by ex vivo anti-CD25 bead depletion; a therapy that impacts the function of suppressor myeloid cells in the tumor; a therapy that enhances immunogenicity of tumor cells (e.g., anthracyclines); adoptive T cell or NK cell transfer including genetically modified cells, e.g., cells modified by chimeric antigen receptors (CAR-T therapy); a therapy that inhibits a metabolic enzyme such as indoleamine dioxigenase (IDO), dioxigenase, arginase or nitric oxide synthetase; a therapy that reverses/prevents T cell anergy or exhaustion; a therapy that triggers an innate immune activation and/or inflammation at a tumor site; administration of immune stimulatory cytokines or blocking of immuno repressive cytokines.

For example, PSGL-1 antagonist can be used with one or more agonistic agents that ligate positive costimulatory receptors; one or more antagonists (blocking agents) that attenuate signaling through inhibitory receptors, such as antagonists that overcome distinct immune suppressive pathways within the tumor microenvironment (e.g., block PD-L1/PD-1/PD-L2 interactions); one or more agents that increase systemically the frequency of anti-tumor immune cells, such as T cells, deplete or inhibit Tregs (e.g., by inhibiting CD25); one or more agents that inhibit metabolic enzymes such as IDO; one or more agents that reverse/prevent T cell anergy or exhaustion; and one or more agents that trigger innate immune activation and/or inflammation at tumor sites.

In one embodiment, a subject having a disease that may benefit from stimulation of the immune system, e.g., cancer or an infectious disease, is treated by administration to the subject of PSGL-1 antagonist and an immuno-oncology agent, wherein the the immuno-oncology agent is a CTLA-4 antagonist, such as an antagonistic CTLA-4 antibody. Suitable CTLA-4 antibodies include, for example, YERVOY (ipilimumab) or tremelimumab.

In one embodiment, a subject having a disease that may benefit from stimulation of the immune system, e.g., cancer or an infectious disease, is treated by administration to the subject of PSGL-1 antagonist and an immuno-oncology agent, wherein the immuno-oncology agent is a PD-1 antagonist, such as an antagonistic PD-1 antibody. Suitable PD-1 antibodies include, for example, OPDIVO (nivolumab), KEYTRUDA (pembrolizumab), or MEDI-0680 (AMP-514; WO2012/145493). The immuno-oncology agent may also include pidilizumab (CT-011), though its specificity for PD-1 binding has been questioned. Another approach to target the PD-1 receptor is the recombinant protein composed of the extracellular domain of PD-L2 (B7-DC) fused to the Fc portion of IgG1, called AMP-224.

In one embodiment, a subject having a disease that may benefit from stimulation of the immune system, e.g., cancer or an infectious disease, is treated by administration to the subject of PSGL-1 antagonist and an immuno-oncology agent, wherein the immuno-oncology agent is a PD-L1 antagonist, such as an antagonistic PD-L1 antibody. Suitable PD-L1 antibodies include, for example, MPDL3280A (RG7446; WO2010/077634), durvalumab (MEDI4736), BMS-936559 (WO2007/005874), MSB0010718C (WO2013/79174) or rHigM12B7.

In one embodiment, a subject having a disease that may benefit from stimulation of the immune system, e.g., cancer or an infectious disease, is treated by administration to the subject of PSGL-1 antagonist and an immuno-oncology agent, wherein the immuno-oncology agent is a LAG-3 antagonist, such as an antagonistic LAG-3 antibody. Suitable LAG3 antibodies include, for example, BMS-986016 (WO10/19570, WO14/08218), or IMP-731 or IMP-321 (WO08/132601, WO09/44273).

In one embodiment, a subject having a disease that may benefit from stimulation of the immune system, e.g., cancer or an infectious disease, is treated by administration to the subject of PSGL-1 antagonist and an immuno-oncology agent, wherein the immuno-oncology agent is a CD137 (4-1BB) agonist, such as an agonistic CD137 antibody. Suitable CD137 antibodies include, for example, urelumab or PF-05082566 (WO12/32433).

In one embodiment, a subject having a disease that may benefit from stimulation of the immune system, e.g., cancer or an infectious disease, is treated by administration to the subject of PSGL-1 antagonist and an immuno-oncology agent, wherein the immuno-oncology agent is a GITR agonist, such as an agonistic GITR antibody. Suitable GITR antibodies include, for example, TRX-518 (WO06/105021, WO09/009116), MK-4166 (WO11/028683) or a GITR antibody disclosed in WO2015/031667.

In one embodiment, a subject having a disease that may benefit from stimulation of the immune system, e.g., cancer or an infectious disease, is treated by administration to the subject of PSGL-1 antagonist and an immuno-oncology agent, wherein the immuno-oncology agent is an OX40 agonist, such as an agonistic OX40 antibody. Suitable OX40 antibodies include, for example, MEDI-6383, MEDI-6469 or MOXR0916 (RG7888; WO06/029879).

In one embodiment, a subject having a disease that may benefit from stimulation of the immune system, e.g., cancer or an infectious disease, is treated by administration to the subject of PSGL-1 antagonist and an immuno-oncology agent, wherein the immuno-oncology agent is a CD40 agonist, such as an agonistic CD40 antibody. In certain embodiments, the immuno-oncology agent is a CD40 antagonist, such as an antagonistic CD40 antibody. Suitable CD40 antibodies include, for example, lucatumumab (HCD122), dacetuzumab (SGN-40), CP-870,893 or Chi Lob 7/4.

In one embodiment, a subject having a disease that may benefit from stimulation of the immune system, e.g., cancer or an infectious disease, is treated by administration to the subject of PSGL-1 antagonist and an immuno-oncology agent, wherein the immuno-oncology agent is a CD27 agonist, such as an agonistic CD27 antibody. Suitable CD27 antibodies include, for example, varlilumab (CDX-1127).

In one embodiment, a subject having a disease that may benefit from stimulation of the immune system, e.g., cancer or an infectious disease, is treated by administration to the subject of PSGL-1 antagonist and an immuno-oncology agent, wherein the immuno-oncology agent is MGA271 (to B7H3) (WO11/109400).

In one embodiment, a subject having a disease that may benefit from stimulation of the immune system, e.g., cancer or an infectious disease, is treated by administration to the subject of PSGL-1 antagonist and an immuno-oncology agent, wherein the immuno-oncology agent is a KIR antagonist, such as lirilumab.

In one embodiment, a subject having a disease that may benefit from stimulation of the immune system, e.g., cancer or an infectious disease, is treated by administration to the subject of PSGL-1 antagonist and an immuno-oncology agent, wherein the immuno-oncology agent is an IDO antagonist. Suitable IDO antagonists include, for example, INCB-024360 (WO2006/122150, WO07/75598, WO08/36653, WO08/36642), indoximod, NLG-919 (WO09/73620, WO09/1156652, WO11/56652, WO12/142237) or F001287.

In one embodiment, a subject having a disease that may benefit from stimulation of the immune system, e.g., cancer or an infectious disease, is treated by administration to the subject of PSGL-1 antagonist and an immuno-oncology agent, wherein the immuno-oncology agent is a Toll-like receptor agonist, e.g., a TLR2/4 agonist (e.g., *Bacillus* Calmette-Guerin); a TLR7 agonist (e.g., Hiltonol or Imiquimod); a TLR7/8 agonist (e.g., Resiquimod); or a TLR9 agonist (e.g., CpG7909).

In one embodiment, a subject having a disease that may benefit from stimulation of the immune system, e.g., cancer or an infectious disease, is treated by administration to the subject of PSGL-1 antagonist and an immuno-oncology agent, wherein, the immuno-oncology agent is a TGF-inhibitor, e.g., GC1008, LY2157299, TEW7197 or IMC-TR1.

Exemplary PSGL-1 Antagonists

In some embodiments, a PSGL-1 antagonist is selected from a PSGL-1 antibody and a VISTA antibody. In some embodiments, a PSGL-1 antagonist is a PSGL-1 antibody. In some embodiments, it is a VISTA antibody. A PSGL-1 antagonist for treating cancer may also be a non-antibody protein, such as PSGL-1 or VISTA or a portion thereof (e.g., the ECD) that inhibits the interaction between PSGL-1 and VISTA, optionally further comprising a fusion partner and in the form of a fusion molecule. The antagonist, in other embodiments, may also be a small molecule or small peptide.

PSGL-1 Antibodies and VISTA Antibodies

In some embodiments, antibodies that block binding of PSGL-1 to VISTA, e.g., at acidic pH, e.g., pH<7.0, ≤6.8, ≤6.5 or ≤6.3 or at pH 5.5 to 6.5, 6.0-6.5, 6.5-7.0 or 6.0-7.0, e.g., pH 6.0, are provided. In some embodiments, antibodies that inhibit PSGL-1-mediated signaling are provided. In some such embodiments, the antibody is PSGL-1 antibody. In some embodiments, PSGL-1 antibody binds to PSGL-1 extracellular domain (ECD). In some embodiments, PSGL-1 antibody inhibits binding of PSGL-1 to VISTA. In some embodiments, PSGL-1 antibody inhibits VISTA-mediated signaling. In some embodiments, PSGL-1 antibody inhibits PSGL-1-mediated signaling.

In some embodiments, PSGL-1 antibody has a dissociation constant (Kd) of ≤1 μM, ≤100 nM, ≤10 nM, ≤1 nM, ≤0.1 nM, ≤0.01 nM, or ≤0.001 nM (e.g. $10^{-8}$M or less, e.g. from $10^{-8}$ M to $10^{-13}$ M, e.g., from $10^{-9}$M to $10^{-13}$ M) for PSGL-1, e.g., for humPSGL-1. In certain embodiments, PSGL-1 antibody has a dissociation constant (Kd) of ≤1 μM, ≤100 nM, ≤10 nM, ≤1 nM, ≤0.1 nM, ≤0.01 nM, or ≤0.001 nM (e.g. $10^{-8}$M or less, e.g. from $10^{-8}$ M to $10^{-13}$ M, e.g., from $10^{-9}$M to $10^{-13}$ M) for PSGL-1, e.g., for humPSGL-1, at acidic pH, e.g., pH<7.0, ≤6.8, ≤6.5 or ≤6.3 or at pH 5.5 to 6.5, 6.0-6.5, 6.5-7.0 or 6.0-7.0, e.g., pH 6.0.

In some embodiments, a PSGL-1 antibody having any the characteristics provided herein inhibits at least 25%, 50%, 75%, 80%, 90% or 100% of the binding of VISTA to PSGL-1.

In some embodiments, an antibody binds to PSGL-1 from multiple species. For example, in some embodiments, an antibody binds to human PSGL-1, and also binds to PSGL-1 from at least one mammal selected from mouse, rat, dog, guinea pig, and cynomolgus monkey.

In some embodiments, the antibody is a VISTA antibody. In some embodiments, a VISTA antibody binds to VISTA extracellular domain (ECD). In some embodiments, a VISTA antibody inhibits binding of VISTA to PSGL-1. In some embodiments, a VISTA antibody inhibits VISTA-mediated signaling. In some embodiments, a VISTA antibody inhibits PSGL-1-mediated signaling. In some embodiments, a VISTA antibody has a dissociation constant (Kd) of ≤1 μM, ≤100 nM, ≤10 nM, ≤1 nM, ≤0.1 nM, ≤0.01 nM, or ≤0.001 nM (e.g. $10^{-8}$ M or less, e.g. from $10^{-8}$ M to $10^{-13}$ M, e.g., from $10^{-9}$ M to $10^{-13}$ M) VISTA, e.g., for human VISTA. In some embodiments, a VISTA antibody has a dissociation constant (Kd) of ≤1 μM, ≤100 nM, ≤10 nM, ≤1 nM, ≤0.1 nM, ≤0.01 nM, or ≤0.001 nM (e.g. $10^{-8}$ M or less, e.g. from $10^{-8}$ M to $10^{-13}$ M, e.g., from $10^{-9}$ M to $10^{-13}$ M) for VISTA, e.g., for human VISTA, at acidic pH, e.g., pH<7.0, ≤6.8, ≤6.5 or ≤6.3 or at pH 5.5 to 6.5, 6.0-6.5, 6.5-7.0 or 6.0-7.0, e.g., pH 6.0.

In some embodiments, a VISTA antibody having any the characteristics provided herein inhibits at least 25%, 50%, 75%, 80%, 90% or 100% of the binding of VISTA to PSGL-1.

In some embodiments, an antibody binds to VISTA from multiple species. For example, in some embodiments, an antibody binds to human VISTA, and also binds to VISTA from at least one mammal selected from mouse, rat, dog, guinea pig, and cynomolgus monkey.

In some embodiments, multispecific antibodies are provided. In some embodiments, bispecific antibodies are provided. Nonlimiting exemplary bispecific antibodies include antibodies comprising a first arm comprising a heavy chain/light chain combination that binds a first antigen and a second arm comprising a heavy chain/light chain combination that binds a second antigen. A further nonlimiting exemplary multispecific antibody is a dual variable domain antibody. In some embodiments, a bispecific antibody comprises a first arm that inhibits binding of PSGL-1 to VISTA and a second arm that stimulates T cells, e.g., by binding CD3. In some embodiments, the first arm binds PSGL-1.

Humanized Antibodies

In some embodiments, PSGL-1 or a VISTA antibody is a humanized antibody. Humanized antibodies are useful as therapeutic molecules because humanized antibodies reduce or eliminate the human immune response to non-human antibodies (such as the human anti-mouse antibody (HAMA) response), which can result in an immune response to an antibody therapeutic, and decreased effectiveness of the therapeutic.

An antibody may be humanized by any method. Nonlimiting exemplary methods of humanization include methods described, e.g., in U.S. Pat. Nos. 5,530,101; 5,585,089; 5,693,761; 5,693,762; 6,180,370; Jones et al., *Nature* 321: 522-525 (1986); Riechmann et al., *Nature* 332: 323-27 (1988); Verhoeyen et al., *Science* 239: 1534-36 (1988); and U.S. Publication No. US 2009/0136500.

As noted above, a humanized antibody is an antibody in which at least one amino acid in a framework region of a non-human variable region has been replaced with the amino acid from the corresponding location in a human framework region. In some embodiments, at least two, at least three, at least four, at least five, at least six, at least seven, at least eight, at least nine, at least 10, at least 11, at least 12, at least 15, or at least 20 amino acids in the framework regions of a non-human variable region are replaced with an amino acid from one or more corresponding locations in one or more human framework regions.

In some embodiments, some of the corresponding human amino acids used for substitution are from the framework regions of different human immunoglobulin genes. That is, in some such embodiments, one or more of the non-human amino acids may be replaced with corresponding amino acids from a human framework region of a first human antibody or encoded by a first human immunoglobulin gene, one or more of the non-human amino acids may be replaced with corresponding amino acids from a human framework region of a second human antibody or encoded by a second human immunoglobulin gene, one or more of the non-human amino acids may be replaced with corresponding amino acids from a human framework region of a third human antibody or encoded by a third human immunoglobulin gene, etc. Further, in some embodiments, all of the corresponding human amino acids being used for substitution in a single framework region, for example, FR2, need not be from the same human framework. In some embodiments, however, all of the corresponding human amino acids being used for substitution are from the same human antibody or encoded by the same human immunoglobulin gene.

In some embodiments, an antibody is humanized by replacing one or more entire framework regions with corresponding human framework regions. In some embodiments, a human framework region is selected that has the highest level of homology to the non-human framework region being replaced. In some embodiments, such a humanized antibody is a CDR-grafted antibody.

In some embodiments, following CDR-grafting, one or more framework amino acids are changed back to the corresponding amino acid in a mouse framework region. Such "back mutations" are made, in some embodiments, to retain one or more mouse framework amino acids that appear to contribute to the structure of one or more of the CDRs and/or that may be involved in antigen contacts and/or appear to be involved in the overall structural integrity of the antibody. In some embodiments, ten or fewer, nine or fewer, eight or fewer, seven or fewer, six or fewer, five or fewer, four or fewer, three or fewer, two or fewer, one, or zero back mutations are made to the framework regions of an antibody following CDR grafting.

In some embodiments, a humanized antibody also comprises a human heavy chain constant region and/or a human light chain constant region.

Chimeric Antibodies

In some embodiments, PSGL-1 antibody or a VISTA antibody is a chimeric antibody. In some embodiments, PSGL-1 antibody or a VISTA antibody comprises at least one non-human variable region and at least one human constant region. In some such embodiments, all of the variable regions of PSGL-1 antibody or a VISTA antibody are non-human variable regions, and all of the constant regions of the PSGL-1 antibody or VISTA antibody are human constant regions. In some embodiments, one or more variable regions of a chimeric antibody are mouse variable regions. The human constant region of a chimeric antibody need not be of the same isotype as the non-human constant region, if any, it replaces. Chimeric antibodies are discussed, e.g., in U.S. Pat. No. 4,816,567; and Morrison et al. *Proc. Natl. Acad. Sci. USA* 81: 6851-55 (1984).

Human Antibodies

In some embodiments, PSGL-1 antibody or a VISTA antibody is a human antibody. Human antibodies can be made by any suitable method. Nonlimiting exemplary methods include making human antibodies in transgenic mice that comprise human immunoglobulin loci. See, e.g., Jakobovits et al., *Proc. Natl. Acad. Sci. USA* 90: 2551-55 (1993); Jakobovits et al., *Nature* 362: 255-8 (1993); Lonberg et al., *Nature* 368: 856-9 (1994); and U.S. Pat. Nos. 5,545,807; 6,713,610; 6,673,986; 6,162,963; 5,545,807; 6,300,129; 6,255,458; 5,877,397; 5,874,299; and 5,545,806.

Nonlimiting exemplary methods also include making human antibodies using phage display libraries. See, e.g., Hoogenboom et al., *J. Mol. Biol.* 227: 381-8 (1992); Marks et al., *J. Mol. Biol.* 222: 581-97 (1991); and PCT Publication No. WO 99/10494.

Human Antibody Constant Regions

In some embodiments, a humanized, chimeric, or human antibody described herein comprises one or more human constant regions. In some embodiments, the human heavy chain constant region is of an isotype selected from IgA, IgG, and IgD. In some embodiments, the human light chain constant region is of an isotype selected from K and 2. In some embodiments, an antibody described herein comprises a human IgG constant region, for example, human IgG1, IgG2, IgG3, or IgG4. In some embodiments, an antibody or Fc fusion partner comprises a C237S mutation, for example, in an IgG1 constant region. See, e.g., SEQ ID NO: 17. In some embodiments, an antibody described herein comprises a human IgG2 heavy chain constant region. In some such embodiments, the IgG2 constant region comprises a P331S mutation, as described in U.S. Pat. No. 6,900,292. In some embodiments, an antibody described herein comprises a human IgG4 heavy chain constant region. In some such embodiments, an antibody described herein comprises an S241P mutation in the human IgG4 constant region. See, e.g., Angal et al. *Mol. Immunol.* 30(1): 105-108 (1993). In some embodiments, an antibody described herein comprises a human IgG4 constant region and a human κ light chain.

The choice of heavy chain constant region can determine whether or not an antibody will have effector function in vivo. Such effector function, in some embodiments, includes antibody-dependent cell-mediated cytotoxicity (ADCC) and/or complement-dependent cytotoxicity (CDC), and can result in killing of the cell to which the antibody is bound. Typically, antibodies comprising human IgG1 or IgG3 heavy chains have effector function.

In some embodiments, effector function is not desirable. For example, in some embodiments, effector function may not be desirable in treatments of inflammatory conditions and/or autoimmune disorders. In some such embodiments, a human IgG4 or IgG2 heavy chain constant region is selected or engineered. In some embodiments, an IgG4 constant region comprises an S241P mutation.

Exemplary Properties of Antibodies

Exemplary Properties of PSGL-1 Antibodies

In some embodiments, PSGL-1 antibody binds to PSGL-1, e.g., at acidic pH, e.g., pH<7.0, ≤6.8, ≤6.5 or ≤6.3 or at pH 5.5 to 6.5, 6.0-6.5, 6.5-7.0 or 6.0-7.0, e.g., pH 6.0, and inhibits PSGL-1-mediated signaling. In some embodiments, PSGL-1 antibody blocks binding of PSGL-1 to VISTA. In some embodiments, PSGL-1 antibody blocks binding of PSGL-1 to VISTA, e.g., by at least 25%, 50%, 75%, 80%, 90% or 100%. In some embodiments, PSGL-1 antibody binds to PSGL-1 with a binding affinity ($K_D$)) of less than 50 nM, less than 20 nM, less than 10 nM, or less than 1 nM. In some embodiments, the extent of binding of PSGL-1 antibody to an unrelated, non-PSGL-1 protein is less than about 10% of the binding of the antibody to PSGL-1 as measured, e.g., by a radioimmunoassay (RIA). In some embodiments, PSGL-1 antibody binds to an epitope of PSGL-1 that is conserved among PSGL-1 from different species. In some embodiments, PSGL-1 antibody binds to the same epitope as a human or humanized PSGL-1 antibody that binds humPSGL-1.

Exemplary Properties of VISTA Antibodies

In some embodiments, a VISTA antibody binds to VISTA, e.g., at acidic pH, e.g., pH<7.0, ≤6.8, ≤6.5 or ≤6.3 or at pH 5.5 to 6.5, 6.0-6.5, 6.5-7.0 or 6.0-7.0, e.g., pH 6.0, and inhibits PSGL-1-mediated signaling. In some embodiments, a VISTA antibody blocks binding of PSGL-1 to VISTA. In some embodiments, a VISTA antibody blocks binding of PSGL-1 to VISTA, e.g., by at least 25%, 50%, 75%, 80%, 90% or 100%. In some embodiments, a VISTA antibody binds to VISTA with a binding affinity ($K_D$)) of less than 50 nM, less than 20 nM, less than 10 nM, or less than 1 nM. In some embodiments, the extent of binding of a VISTA antibody to an unrelated, non-VISTA protein is less than about 10% of the binding of the antibody to VISTA as measured, e.g., by a radioimmunoassay (RIA). In some embodiments, a VISTA antibody binds to an epitope of VISTA that is conserved among VISTA from different species. In some embodiments, a VISTA antibody binds to the same epitope as a human or humanized VISTA antibody that binds human VISTA.

Antibody Conjugates

In some embodiments, PSGL-1 or a VISTA antibody is conjugated to a label. As used herein, a label is a moiety that facilitates detection of the antibody and/or facilitates detection of a molecule to which the antibody binds. Nonlimiting exemplary labels include, but are not limited to, radioisotopes, fluorescent groups, enzymatic groups, chemiluminescent groups, biotin, epitope tags, metal-binding tags, etc. One skilled in the art can select a suitable label according to the intended application.

In some embodiments, a label is conjugated to an antibody using chemical methods in vitro. Nonlimiting exemplary chemical methods of conjugation are known in the art, and include services, methods and/or reagents commercially available from, e.g., Thermo Scientific Life Science Research Produces (formerly Pierce; Rockford, IL), Prozyme (Hayward, CA), SACRI Antibody Services (Calgary, Canada), AbD Serotec (Raleigh, NC), etc. In some embodiments, when a label is a polypeptide, the label can be expressed from the same expression vector with at least one antibody chain to produce a polypeptide comprising the label fused to an antibody chain.

PSGL-1 and VISTA ECDs, ECD Fusion Molecules, and Small Peptides

In some embodiments, the PSGL-1 antagonist is a PSGL-1 polypeptide, such as a full-length PSGL-1, or a fragment of PSGL-1 that inhibits binding of PSGL-1 to VISTA. In some embodiments, the PSGL-1 antagonist is a PSGL-1 extracellular domain (ECD). In some embodiments, the PSGL-1 antagonist is a full-length PSGL-1 ECD. In some embodiments, the PSGL-1 ECD is a PSGL-1 ECD fragment, for example, comprising at least 80%, at least 85%, at least 90%, or at least 95% of the full length PSGL-1 ECD amino acid sequence from which it is derived. In some embodiments the PSGL-1 ECD is a PSGL-1 ECD variant, for example, comprising at least 80%, at least 85%, at least 90%, at least 92%, at least 95%, at least 97%, at least 98%, or at least 99% sequence identity with the full length PSGL-1 ECD from which it is derived. In other embodiments, the PSGL-1 ECD is from a non-human PSGL-1 ECD and may be either full length, a fragment, or a variant.

In some embodiments, the PSGL-1 or PSGL-1 fragment is combined with at least one fusion partner. Thus, in some such embodiments the PSGL-1 antagonist may comprise a full length PSGL-1 ECD and at least one fusion partner to form a PSGL-1 ECD fusion molecule. In some embodiments, the PSGL-1 ECD portion of the fusion molecule comprises a PSGL-1 ECD fragment, for example, comprising at least 80%, at least 85%, at least 90%, or at least 95% of the full length PSGL-1 ECD amino acid sequence from which it is derived. In some embodiments, the PSGL-1 ECD portion of the fusion molecule is a PSGL-1 ECD variant, for example, comprising at least 80%, at least 85%, at least 90%, at least 92%, at least 95%, at least 97%, at least 98%, or at least 99% sequence identity with the full length PSGL-1 ECD from which it is derived. In other embodiments, the PSGL-1 ECD component is from a non-human PSGL-1 ECD and may be full length, a fragment, or a variant. In any of the fusion molecule embodiments above, the fusion partner may comprise an immunoglobulin Fc molecule, for example, a human Fc molecule, or in some embodiments an Fc having a sequence chosen from SEQ ID NOs: 11-13. In other embodiments, the fusion partner may be a different molecule such as albumin or polyethylene glycol (PEG). In some embodiments, more than one fusion partner may be attached to the PSGL-1 ECD. In some embodiments, the fusion partner (or partners) is attached at the C-terminal of the ECD, while other attachments are also possible such as on an amino acid side-chain or at the N-terminus. The attachment of a fusion partner to a PSGL-1 ECD may be direct (i.e. by a covalent bond) or indirect through a linker. A linker may comprise, for example, at least one intervening amino acid or some other chemical moiety serving to link the fusion partner to the ECD either covalently or noncovalently.

In any of the above embodiments, the PSGL-1 polypeptide may either include a signal sequence or be in a mature form, i.e., not including a signal sequence. The signal sequence may be from a native PSGL-1 molecule or it may be a signal sequence from a different protein, for example one chosen to enhance expression of the PSGL-1 polypeptide in cell culture.

In some embodiments a PSGL-1 ECD may comprise the sequence of amino acids 1-241 of SEQ ID NO: 1 or 1-241 of SEQ ID NO: 14 (human isoforms 1 and 2, respectively, including signal sequence). In other embodiments, a PSGL-1 ECD may comprise the sequence of amino acids 23-241 of SEQ ID NO: 1 or 23-241 of SEQ ID NO: 14 or amino acids 1-219 of SEQ ID NO: 2 or amino acids 1-219 of SEQ ID NO: 15 or the amino acid sequence of SEQ ID NO: 3 or of SEQ ID NO: 4 or of SEQ ID NO: 16 or of SEQ ID NO: 17 (human isoforms 1 and 2, mature forms without signal sequence), or SEQ ID NO: 18 (another exemplary ECD sequence). In some embodiments, the PSGL-1 ECD may consist of one of the above amino acid sequences. In any of the above cases, a PSGL-1 ECD may be part of a fusion molecule such that the above amino acid sequence may be joined to a fusion partner either directly or via a linker, such as an Fc, albumin, or PEG. For example, in some embodiments in which the antagonist is a PSGL-1 ECD fusion molecule, the fusion molecule may comprise one of the above sequences plus at least one of SEQ ID NOs: 11-13 (immunoglobulin Fc sequences) or an Fc from human IgG1. A PSGL-1 ECD Fc fusion molecule may be formed by a direct attachment of the PSGL-1 ECD amino acid sequence to the Fc amino acid sequence or via a linker (either an intervening amino acid or amino acid sequence or another chemical moiety). SEQ ID NO: 19, for example, provides a linker used in a PSGL-1 Fc molecule used in the examples below. Additional PSGL-1 ECD Fc fusion molecules are described in T. Pouyani et al., *Cell* 83: 333-343 (1995).

In some embodiments, the PSGL-1 antagonist is a VISTA polypeptide, such as a full-length VISTA or a fragment of VISTA that inhibits the interaction between VISTA and PSGL-1. For example, in some embodiments, the PSGL-1 antagonist is a full-length VISTA polypeptide. In some embodiments, the PSGL-1 antagonist is a VISTA extracellular domain (ECD). In some embodiments, the PSGL-1 antagonist is a full-length human VISTA ECD. In some embodiments, the VISTA ECD may be a VISTA ECD fragment, for example, comprising at least 80%, at least 85%, at least 90%, or at least 95% of the full length VISTA ECD amino acid sequence from which it is derived. In some embodiments the VISTA ECD is a VISTA ECD variant, for example, comprising at least 80%, at least 85%, at least 90%, at least 92%, at least 95%, at least 97%, at least 98%, or at least 99% sequence identity with the full length VISTA ECD from which it is derived. In other embodiments, the VISTA ECD is from a non-human VISTA ECD and may be either full length, a fragment, or a variant.

In some embodiments, the VISTA or VISTA fragment is combined with at least one fusion partner. Thus, in some such embodiments the PSGL-1 antagonist may comprise a full length VISTA ECD and at least one fusion partner to form a VISTA ECD fusion molecule. In some embodiments, the VISTA ECD portion of the fusion molecule comprises a VISTA ECD fragment, for example, comprising at least 80%, at least 85%, at least 90%, or at least 95% of the full length VISTA ECD amino acid sequence from which it is derived. In some embodiments, the VISTA ECD portion of the fusion molecule is a VISTA ECD variant, for example, comprising at least 80%, at least 85%, at least 90%, at least 92%, at least 95%, at least 97%, at least 98%, or at least 99% sequence identity with the full length VISTA ECD from which it is derived. In other embodiments, the VISTA ECD component is from a non-human VISTA ECD and may be full length, a fragment, or a variant. In any of the fusion molecule embodiments above, the fusion partner may comprise an immunoglobulin Fc molecule, for example a human Fc molecule, in some embodiments having a sequence chosen from SEQ ID NOs: 11-13. In other embodiments, the fusion partner may be a different molecule such as albumin or polyethylene glycol (PEG). In some embodiments, more than one fusion partner may be attached to the VISTA ECD. In some embodiments, the fusion partner (or partners) is attached at the C-terminal of the ECD, while other attachments are also possible such as on an amino acid side-chain or at the N-terminus. The attachment of a fusion partner to a VISTA ECD may be direct (i.e. by a covalent bond) or indirect through a linker. A linker may comprise, for example, at least one intervening amino acid or some other chemical moiety serving to link the fusion partner to the ECD either covalently or noncovalently.

In any of the above embodiments, the VISTA polypeptide may either include a signal sequence or be in a mature form, i.e., not including a signal sequence. The signal sequence may be from a native VISTA molecule or it may be a signal sequence from a different protein, for example one chosen to enhance expression of the VISTA polypeptide in cell culture.

In some embodiments a VISTA ECD may comprise the sequence of amino acids 1-202 of SEQ ID NO: 10. In some embodiments, the VISTA ECD may consist of the above amino acid sequence. In either of the above cases, a VISTA ECD may be part of a fusion molecule such that the above amino acid sequence may be joined to a fusion partner either directly or via a linker, such as an Fc, albumin, or PEG. For example, in some embodiments in which the antagonist is a VISTA ECD fusion molecule, the fusion molecule may comprise the sequence of amino acids 1-202 of SEQ ID NO: 10 plus at least one of SEQ ID NOs: 11-13 (immunoglobulin Fc sequences), or the entire fusion molecule may comprise or consist of the amino acid sequence of SEQ ID NO: 9 (an exemplary VISTA ECD Fc fusion protein). A VISTA ECD Fc fusion molecule may be formed by a direct attachment of the VISTA ECD amino acid sequence to the Fc amino acid sequence or via a linker (either an intervening amino acid or amino acid sequence or another chemical moiety).

In some embodiments, the PSGL-1 antagonist may be a small molecule or a peptide, e.g., a small peptide. In some embodiments, the PSGL-1 antagonist may be a small peptide comprising an amino acid sequence of a PSGL-1 ECD fragment. In some embodiments, the PSGL-1 antagonist may be a small peptide comprising an amino acid sequence of a VISTA ECD fragment. In some embodiments, the PSGL-1 antagonist is a small peptide having, e.g., from 3 to 20, e.g., 3 to 15 or 3 to 10 amino acids, which peptide may be linear or circular, with a sequence comprising a PSGL-1 fragment, a PSGL-1 ECD fragment, a VISTA fragment, or a VISTA ECD fragment, or a variant of a PSGL-1 fragment, a PSGL-1 ECD fragment, a VISTA fragment, or a VISTA ECD fragment. Such a variant of a PSGL-1 or VISTA fragment may have, for example, at least 95%, at least 97%, at least 99% sequence identity to the native fragment sequence from which it is derived Signal Peptides In order for some secreted proteins to express and secrete in large quantities, a signal peptide from a heterologous protein may be desirable. Employing heterologous signal peptides may be advantageous in that a resulting mature polypeptide may remain unaltered as the signal peptide is removed in the ER during the secretion process. The addition of a heterologous signal peptide may be required to express and secrete some proteins.

Nonlimiting exemplary signal peptide sequences are described, e.g., in the online Signal Peptide Database maintained by the Department of Biochemistry, National University of Singapore. See Choo et al., *BMC Bioinformatics*, 6: 249 (2005); and PCT Publication No. WO 2006/081430.

Co-Translational and Post-Translational Modifications

In some embodiments, a polypeptide such as PSGL-1 or a VISTA antibody or a PSGL-1 or VISTA ECD is differentially modified during or after translation, for example by glycosylation, sialylation, acetylation, phosphorylation, amidation, derivatization by known protecting/blocking groups, proteolytic cleavage, or linkage to an antibody molecule or other cellular ligand. Any of numerous chemical modifications may be carried out by known techniques, including, but not limited to, specific chemical cleavage by cyanogen bromide, trypsin, chymotrypsin, papain, V8 protease; $NABH_4$: acetylation; formylation; oxidation; reduction; and/or metabolic synthesis in the presence of tunicamycin.

Additional post-translational modifications encompassed by the invention include, for example, N-linked or O-linked carbohydrate chains; processing of N-terminal or C-terminal ends; attachment of chemical moieties to the amino acid backbone; chemical modifications of N-linked or O-linked carbohydrate chains; and addition or deletion of an N-terminal methionine residue as a result of prokaryotic host cell expression.

Nucleic Acid Molecules Encoding PSGL-1 Antagonists

Nucleic acid molecules are provided, wherein the nucleic acid molecules comprise polynucleotides that encode one or more chains of an antibody described herein, such as PSGL-1 or a VISTA antibody. In some embodiments, a nucleic acid molecule comprises a polynucleotide that encodes a heavy chain or a light chain of an antibody described herein. In some embodiments, a nucleic acid molecule comprises both a polynucleotide that encodes a heavy chain and a polynucleotide that encodes a light chain, of an antibody described herein. In some embodiments, a first nucleic acid molecule comprises a first polynucleotide that encodes a heavy chain and a second nucleic acid molecule comprises a second polynucleotide that encodes a light chain.

In some such embodiments, the heavy chain and the light chain are expressed from one nucleic acid molecule, or from two separate nucleic acid molecules, as two separate polypeptides. In some embodiments, such as when an antibody is an scFv, a single polynucleotide encodes a single polypeptide comprising both a heavy chain and a light chain linked together.

In some embodiments, a polynucleotide encoding a heavy chain or light chain of an antibody described herein comprises a nucleotide sequence that encodes a leader sequence, which, when translated, is located at the N-terminus of the heavy chain or light chain. As discussed above, the leader sequence may be the native heavy or light chain leader sequence, or may be another heterologous leader sequence.

Nucleic acids encoding other PSGL-1 antagonists are also provided, such as fragments or variants of PSGL-1 including PSGL-1 ECD molecules or PSGL-1 ECD fusion molecules and including fragments or variants of VISTA including VISTA ECD molecules or VISTA ECD fusion molecules. Nucleic acid molecules may be constructed using recombinant DNA techniques conventional in the art. In some embodiments, a nucleic acid molecule is an expression vector that is suitable for expression in a selected host cell.

Polypeptide Expression and Production

Vectors

Vectors comprising polynucleotides that encode heavy chains and/or light chains of the antibodies described herein are provided. Such vectors include, but are not limited to, DNA vectors, phage vectors, viral vectors, retroviral vectors, etc. In some embodiments, a vector comprises a first polynucleotide sequence encoding a heavy chain and a second polynucleotide sequence encoding a light chain. In some embodiments, the heavy chain and light chain are expressed from the vector as two separate polypeptides. In some embodiments, the heavy chain and light chain are expressed as part of a single polypeptide, such as, for example, when the antibody is an scFv.

In some embodiments, a first vector comprises a polynucleotide that encodes a heavy chain and a second vector comprises a polynucleotide that encodes a light chain. In some embodiments, the first vector and second vector are transfected into host cells in similar amounts (such as similar molar amounts or similar mass amounts). In some embodiments, a mole- or mass-ratio of between 5:1 and 1:5 of the first vector and the second vector is transfected into host cells. In some embodiments, a mass ratio of between 1:1 and 1:5 for the vector encoding the heavy chain and the vector encoding the light chain is used. In some embodiments, a mass ratio of 1:2 for the vector encoding the heavy chain and the vector encoding the light chain is used.

In some embodiments, a vector is selected that is optimized for expression of polypeptides in CHO or CHO-derived cells, or in NSO cells. Exemplary such vectors are described, e.g., in Running Deer et al., *Biotechnol. Prog.* 20:880-889 (2004).

In some embodiments, a vector is chosen for in vivo expression of PSGL-1 antagonist in animals, including humans. In some such embodiments, expression of the polypeptide or polypeptides is under the control of a promoter or promoters that function in a tissue-specific manner. For example, liver-specific promoters are described, e.g., in PCT Publication No. WO 2006/076288.

Host Cells

In various embodiments, heavy chains and/or light chains of the antibodies described herein may be expressed in prokaryotic cells, such as bacterial cells; or in eukaryotic cells, such as fungal cells (such as yeast), plant cells, insect cells, and mammalian cells. Such expression may be carried out, for example, according to procedures known in the art. Exemplary eukaryotic cells that may be used to express polypeptides include, but are not limited to, COS cells, including COS 7 cells; 293 cells, including 293-6E cells; CHO cells, including CHO-S and DG44 cells; PER.C6R cells (Crucell); and NSO cells. In some embodiments, heavy chains and/or light chains of the antibodies described herein may be expressed in yeast. See, e.g., U.S. Publication No. US 2006/0270045 A1. In some embodiments, a particular eukaryotic host cell is selected based on its ability to make desired post-translational modifications to the heavy chains and/or light chains of PSGL-1 or a VISTA antibody. For example, in some embodiments, CHO cells produce polypeptides that have a higher level of sialylation than the same polypeptide produced in 293 cells.

Introduction of one or more nucleic acids into a desired host cell may be accomplished by any method, including but not limited to, calcium phosphate transfection, DEAE-dextran mediated transfection, cationic lipid-mediated transfection, electroporation, transduction, infection, etc. Nonlimiting exemplary methods are described, e.g., in Sambrook et al., *Molecular Cloning, A Laboratory Manual,* 3rd ed. Cold Spring Harbor Laboratory Press (2001). Nucleic acids may be transiently or stably transfected in the desired host cells, according to any suitable method.

In some embodiments, one or more polypeptides may be produced in vivo in an animal that has been engineered or transfected with one or more nucleic acid molecules encoding the polypeptides, according to any suitable method.

Purification of Polypeptides

The antibodies described herein may be purified by any suitable method. Such methods include, but are not limited to, the use of affinity matrices or hydrophobic interaction chromatography. Suitable affinity ligands include the antigen and/or epitope to which the antibody binds, and ligands that bind antibody constant regions. For example, a Protein A, Protein G, Protein A/G, or an antibody affinity column may be used to bind the constant region and to purify an antibody.

In some embodiments, hydrophobic interactive chromatography, for example, a butyl or phenyl column, is also used for purifying some polypeptides. Many methods of purifying polypeptides are known in the art.

Cell-Free Production of Polypeptides

In some embodiments, an antibody described herein is produced in a cell-free system. Nonlimiting exemplary cell-free systems are described, e.g., in Sitaraman et al., *Methods Mol. Biol.* 498: 229-44 (2009); Spirin, *Trends Biotechnol.* 22: 538-45 (2004); Endo et al., *Biotechnol. Adv.* 21: 695-713 (2003).

Methods of Identifying PSGL-1 Antagonists

In some embodiments, methods of identifying PSGL-1 antagonists are provided. In some embodiments, a method comprises contacting a candidate molecule (i.e., a molecule being tested for antagonist activity) with VISTA, a VISTA ECD, or a VISTA ECD fusion molecule (collectively referred to as a "VISTA molecule"), e.g., at acidic pH, e.g., pH<7.0, ≤6.8, ≤6.5 or ≤6.3 or at pH 5.5 to 6.5, 6.0-6.5, 6.5-7.0 or 6.0-7.0, e.g., pH 6.0. In some embodiments, a method further comprises contacting the candidate molecule/VISTA molecule mixture with PSGL-1, PSGL-1 ECD, or PSGL-1 ECD fusion molecule (collectively referred to as an "PSGL-1 molecule"). In some embodiments, a method comprises contacting the candidate molecule with the PSGL-1 molecule, and then contacting the candidate molecule/PSGL-1 molecule mixture with a VISTA molecule, e.g., at acidic pH, e.g., pH<7.0, ≤6.8, ≤6.5 or ≤6.3 or at pH 5.5 to 6.5, 6.0-6.5, 6.5-7.0 or 6.0-7.0, e.g., pH 6.0. In some embodiments, a method comprises contacting a candidate molecule with a VISTA molecule and PSGL-1 molecule approximately simultaneously. In some embodiments, a method comprises forming a first composition comprising a VISTA molecule and PSGL-1 molecule, e.g., at acidic pH, e.g., pH<7.0, ≤6.8, ≤6.5 or ≤6.3 or at pH 5.5 to 6.5, 6.0-6.5, 6.5-7.0 or 6.0-7.0, e.g., pH 6.0, and then contacting the candidate molecule with the first composition. One skilled in the art will recognize that the order in which the components are contacted with one another may be varied according to the assay design. In some embodiments, contacting the VISTA molecule, PSGL-1 molecule, and candidate molecule occurs at an acidic pH, or a pH that is lower than pH 8.0, lower than pH 7.0, lower than pH 6.5 or lower than pH 6.0 or at pH 5.5 to 6.5, 6.0-6.5, 6.5-7.0 or 6.0-7.0, e.g., pH 6.0. The pH of the composition may be pH 5.0 to pH 8.0, pH 5.5 to pH 7.0, pH 6.0 to pH 8, or pH 6.5 to pH 8.

In some embodiments, the VISTA molecule is a full length VISTA, for example, VISTA expressed on the surface of a cell. In some embodiments, the VISTA molecule is a soluble VISTA, such as a VISTA ECD or VISTA ECD fusion molecule. In some embodiments, the PSGL-1 molecule is a full length PSGL-1, for example, PSGL-1 expressed on the surface of a cell. In some embodiments, the PSGL-1 molecule is a soluble PSGL-1, such as PSGL-1 ECD or PSGL-1 ECD fusion molecule.

In some embodiments, after the candidate molecule has been contacted with the VISTA molecule and/or the PSGL-1 molecule, an assay or assays are carried out to detect PSGL-1 molecule binding to the VISTA molecule. Nonlimiting exemplary assays for detecting PSGL-1 molecule binding to a VISTA molecule include ELISA assays, surface plasmon resonance assays (e.g., Biacore®), flow cytometry-based assays (for example, when one or more components are bound to beads, or are expressed on the surface of cells), amplified luminescent proximity homogeneous assay (ALPHA), etc. Many methods of detecting protein-protein binding are known in the art, and one skilled in the art can select a suitable assay method. Further, various reagents may be used for detection as needed, including antibodies (with or without labels), secondary antibodies (with or without labels), labeled assay components (including, but not limited to, labeled PSGL-1 molecule and/or labeled VISTA molecule), etc.

In some embodiments, methods of identifying PSGL-1 antagonists comprise comparing the extent of VISTA molecule/PSGL-1 molecule binding in the presence and absence of the candidate molecule, e.g., at acidic pH, e.g., pH<7.0, ≤6.8, ≤6.5 or ≤6.3 or at pH 5.5 to 6.5, 6.0-6.5, 6.5-7.0 or 6.0-7.0, e.g., pH 6.0. In some embodiments, when VISTA molecule/PSGL-1 molecule binding is reduced in the presence of the candidate molecule relative to the binding in the absence of the candidate molecule, the candidate molecule is PSGL-1 antagonist. In some embodiments, binding between the VISTA molecule and the PSGL-1 molecule is reduced by at least 20%, at least 30%, at least 40%, at least 50%, at least 60%, at least 70%, at least 80%, or at least 90% in the presence of the candidate molecule. In some such embodiments, the candidate molecule is PSGL-1 antagonist.

Exemplary classes of candidate molecules include, but are not limited to, antibodies, peptides, small molecules, and aptamers. In some embodiments, a candidate molecule is an antibody that is known to bind to VISTA (i.e., a VISTA antibody). In some embodiments, a candidate molecule is an antibody that is known to bind to PSGL-1 (i.e., PSGL-1 antibody).

In some embodiments, methods of determining whether a VISTA antibody is a PSGL-1 antagonist are provided. In such embodiments, the VISTA antibody is tested in the assays described above as the candidate molecule. In some embodiments, methods of determining whether a VISTA antibody blocks binding of PSGL-1 to VISTA, e.g., at acidic pH, e.g., pH<7.0, ≤6.8, ≤6.5 or ≤6.3 or at pH 5.5 to 6.5, 6.0-6.5, 6.5-7.0 or 6.0-7.0, e.g., pH 6.0, are provided. Such methods comprise, in some embodiments, contacting a VISTA antibody with a VISTA molecule and PSGL-1 molecule, and detecting binding of the VISTA molecule to the PSGL-1 molecule in the presence of the antibody, e.g., as described above and herein.

Articles of Manufacture

In some embodiments, an article of manufacture or a kit containing materials useful for the detection of a biomarker (e.g., PSGL-1 or VISTA) or for the treatment, prevention and/or diagnosis of the disorders described above is provided. The article of manufacture comprises a container and a label or package insert on or associated with the container. Suitable containers include, for example, bottles, vials, syringes, etc. The containers may be formed from a variety of materials such as glass or plastic. In some embodiments, the container holds a composition that is by itself or combined with another composition effective for treating, preventing and/or diagnosing the condition and may have a sterile access port (for example the container may be an intravenous solution bag or a vial having a stopper pierceable by a hypodermic injection needle). The label or package insert indicates that the composition is used for treating the condition of choice. In some embodiments, the article of manufacture may comprise (a) a first container with a composition contained therein, wherein the composition comprises PSGL-1 antagonist of the invention; and (b) a second container with a composition contained therein, wherein the composition comprises an additional therapeutic agent. The article of manufacture may further comprise a package insert indicating that the compositions can be used to treat a particular condition. Alternatively, or additionally, the article of manufacture may further comprise a second (or third) container comprising a pharmaceutically-acceptable buffer, such as bacteriostatic water for injection (BWFI), phosphate-buffered saline, Ringer's solution and dextrose solution. It may further include other materials desirable from a commercial and user standpoint, including other buffers, diluents, filters, needles, and syringes.

In some embodiments, the molecules of the present invention can be packaged alone or in combination with other therapeutic compounds as a kit. In one embodiment, the therapeutic compound is an anti-cancer agent. In another embodiment, the therapeutic compound is an immunosuppressive agent. The kit can include optional components that aid in the administration of the unit dose to patients, such as vials for reconstituting powder forms, syringes for injection, customized IV delivery systems, inhalers, etc. Additionally, the unit dose kit can contain instructions for preparation and administration of the compositions. The kit may be manufactured as a single use unit dose for one patient, multiple uses for a particular patient (at a constant dose or in which the individual compounds may vary in potency as therapy progresses); or the kit may contain multiple doses suitable for administration to multiple patients ("bulk packaging"). The kit components may be assembled in cartons, blister packs, bottles, tubes, and the like.

EXAMPLES

The examples discussed below are intended to be purely exemplary of the invention and should not be considered to limit the invention in any way. The examples are not intended to represent that the experiments below are all or the only experiments performed. Efforts have been made to ensure accuracy with respect to numbers used (for example, amounts, temperature, etc.) but some experimental errors and deviations should be accounted for. Unless indicated otherwise, parts are parts by weight, molecular weight is average molecular weight, temperature is in degrees Centigrade, and pressure is at or near atmospheric.

Example 1: The VISTA ECD is Histidine Rich and VISTA Dextramers Bind Leukocytes Selectively at Acidic pH The frequency of histidine residues within the extracellular domains of immunoglobulin receptor superfamily (IgSF) members was analyzed and VISTA was found to be exceptionally histidine-rich relative to that of other receptors or ligands.

PBMC CD4+ T cells were isolated from blood by RosetteSep® (Stem Cell Technologies) and stimulated for 3-4 days with a 1:1 ratio of anti-CD3/CD28 Dynabeads® (ThermoFisher) and recombinant human IL-2. After stimulation, the CD4+ T cells were washed and then incubated with fluorescently-conjugated human VISTA dextramers (a streptavidin dextramer loaded with an optimal molar ratio of monobiotinylated recombinant human VISTA molecules) at a pH ranging between 6.97 and 5.99. Binding was detected by flow cytometry.

The results, which are shown in FIG. 1, indicate that VISTA binds T cells selectively at acidic pH, rather than at neutral pH.

Example 2: Identification of PSGL-1 as a VISTA Counter-Receptor at Acidic pH The LRC-TriCEPS™ technology was used to identify VISTA receptor on T cells (Frei et al. (2013) *Nat. Protoc.* 8:1321; Frei and Jeon (2012) *Nat. Biotechnol.* 30:997 and Omasits et al. (2014) *Bioinformatics* 15:884). Human VISTA-Fc was coupled to TriCEPS and incubated on primary human T cells at pH6.0. Anti-CD3 was also coupled to the TriCEPS reagent and served as a positive control. Several proteins were identified in the screen, some of which appeared to bind only to the Fc portion of VISTA-Fc. Human PSGL-1 was identified as a protein binding to human VISTA. The screening experiment was repeated one more time in the same conditions, and PSGL-1 was identified again.

P-Selectin Glycoprotein Ligand 1 (PSGL-1, or SELPL) is a ligand for P-, E-, and L-selectin, is heavily glycosylated and tyrosine sulfated and expressed by most leukocytes, including T cells. PSGL-1 engagement of selectins is critical to leukocyte extravasation and trafficking.

Example 3: PSGL-1 Expression Correlates with VISTA Dextramer Binding

PBMC were isolated from blood by ficoll-paque gradient centrifugation, washed, and then incubated in Hank's Balanced Salt Solution (HBSS) at pH 7.2 with fluorescently-conjugated anti-PSGL-1 antibodies or at pH 6.0 with fluorescently-conjugated human VISTA dextramers (a streptavidin dextramer loaded with an optimal molar ratio of monobiotinylated recombinant human VISTA molecules). Binding was detected by flow cytometry.

Figure 2A:
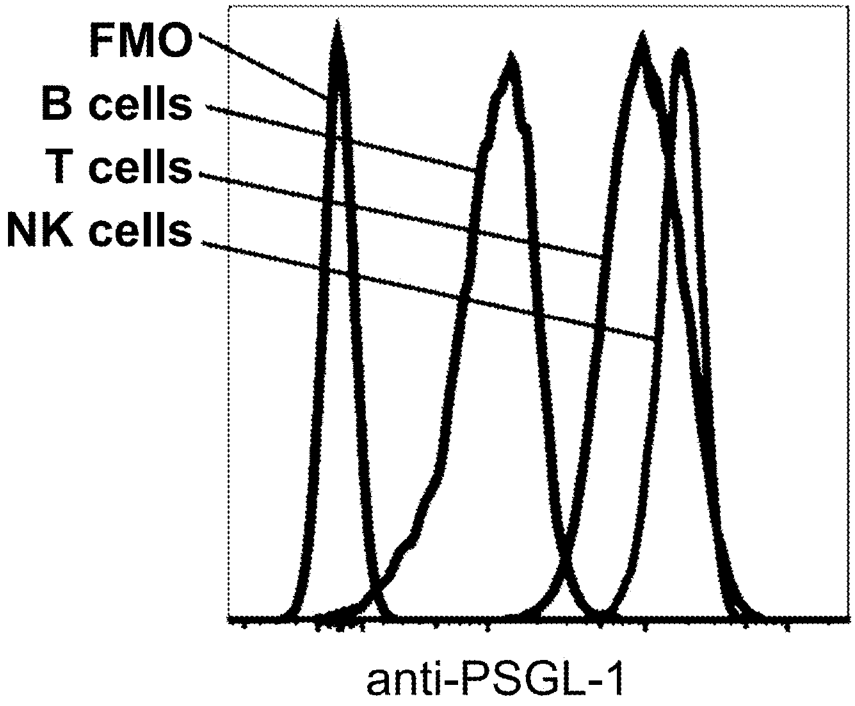
FIG. 2A shows binding of anti-PSGL-1 to B cells, T cells and NK cells, as described in Example 2.
Figure 2B:
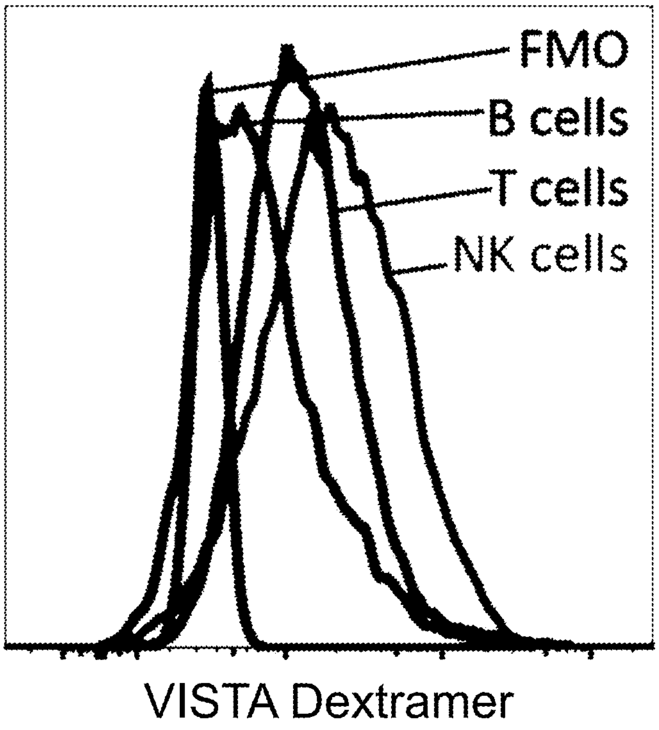
FIG. 2B shows binding of VISTA Dextramer to B cells, T cells and NK cells, as also described in Example 2.

The results, which are shown in FIG. 2A-B, indicate that PSGL-1 surface expression on the PBMC lymphocytes correlates with VISTA dextramer binding at acidic pH.

Figure 3:
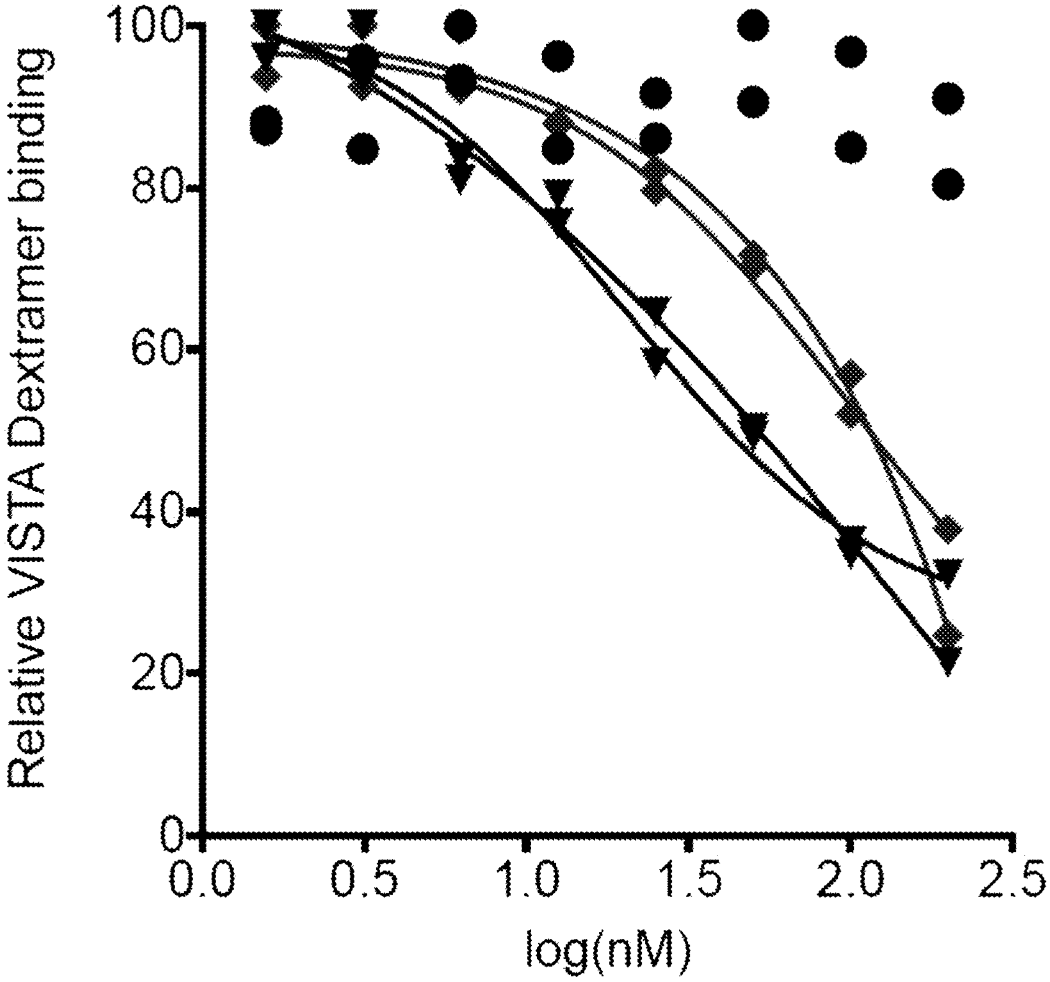
FIG. 3 shows the relative VISTA Dextramer binding to activated human CD4+ T cells in the presence of a control antibody (•), hPSGL-1-Fc (▼) or p-selectin (diamonds).

Example 4: Soluble PSGL-1 and P-Selectin Block VISTA Dextramer Binding to Activated CD4+ T Cells The ability of soluble PSGL-1 to disrupt VISTA dextramer binding to T cells was assessed by incubating activated T cells with fluorescently-conjugated VISTA dextramers (a streptavidin dextramer loaded with a sub-optimal molar ratio of monobiotinylated recombinant human VISTA molecules) in Hanks's Balanced Salt Solution at pH 6.0 and in the presence of titrated concentrations of a control (i.e., non-VISTA or PSGL-1 specific) antibody (dots), recombinant human PSGL-1-Fc fusion protein (triangles), or recombinant human P-selectin (R&D Systems, diamonds). The recombinant human PSGL-1 Fc fusion molecule was obtained from R&D Systems Catalog No. 3345-PS, and comprises the PSGL-1 ECD sequence shown in SEQ ID NO: 18, comprising positions 42-295 of a human PSGL-1 sequence of accession number AA50061 coupled at its C-terminal to an IEGRMD linker sequence (SEQ ID NO: 19) followed by amino acids P100 to K330 of human IgG1. After incubation, the binding of the VISTA dextramer to the T cells was measured by flow cytometry. IC50 values were calculated via nonlinear regression in Prism software (GraphPad). The results, which are shown in FIG. 3 and Table 1, indicate that PSGL-1 and P-selectin inhibit binding of VISTA to the activated CD4+ T cells in a dose dependent manner at acidic pH.

TABLE 1

| Agent | IC50 (nM) |
|---|---|
| Control antibody | — |
| PSGL-1-Fc | 20.54 |
| p-selectin | 100.8 |

Example 5: PSGL-1-Fc Binds to Cell Surface-Expressed VISTA at Acidic pH

Figure 4A:
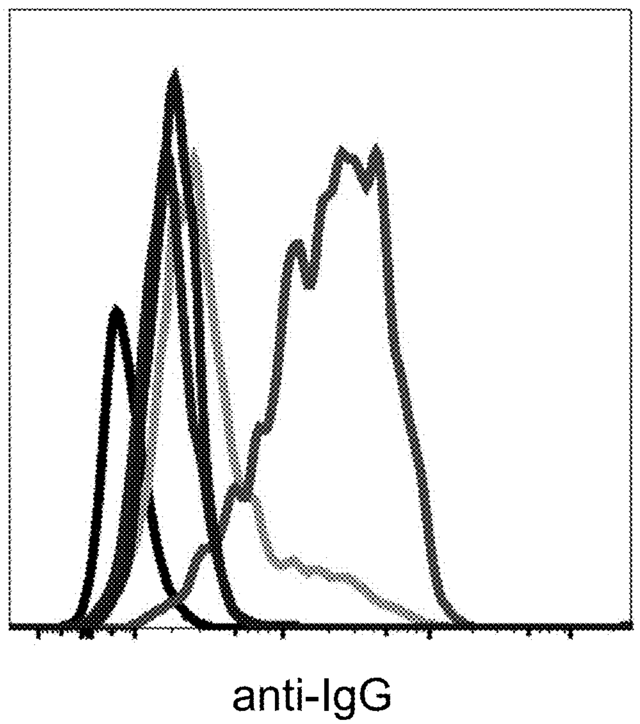
FIGS. 4A and 4B show that PSGL-1 binds to 293T-hVISTA cells at pH 6.0.
Figure 4B:
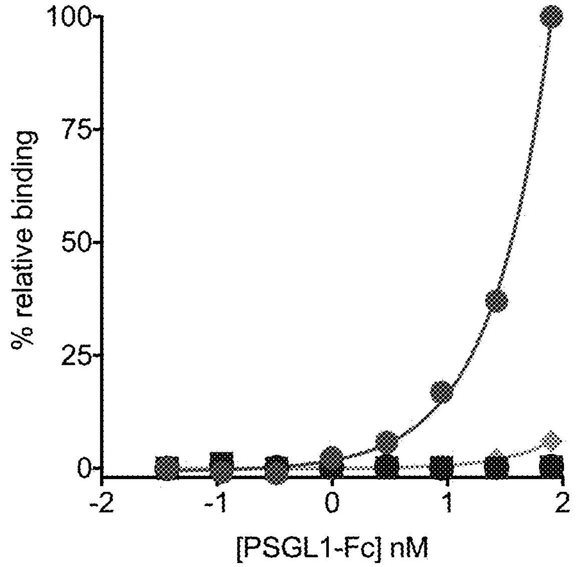

The binding of humPSGL-1-Fc to 293 T cells ectopically expressing human VISTA was tested. 293T cells expressing human VISTA and GFP (dots and squares) were cultured as well as 293T cells expressing neither VISTA nor GFP (diamonds and triangles). The cells were washed and then incubated with PSGL-1-Fc fusion protein (R&D Systems; Cat. No. 3345) in Hanks's Balanced Salt Solution at either pH 7.2 (triangles and squares) or pH 6.0 (diamonds and dots curves). After primary incubation, cells were washed and incubated with fluorescently-conjugated anti-hIgG secondary detection antibodies. After secondary incubation, cells were washed and binding was detected by flow cytometry. The results, which are shown in FIGS. 4A and B, indicate that humPSGL-1-Fc binds to 293 T cells expressing human VISTA (hVISTA), but not to 293 T cells that do not express human VISTA. In addition, the results indicate that the binding of PSGL-1-Fc is pH dependent, as it binds at pH 6.0 (circles/dots in FIG. 4B and right curve in FIG. 4A), but not significantly at pH 7.2 (squares in FIG. 4B and left curves in FIG. 4A).

Example 6: PBMC CD4 T Cell PSGL-1 CRISPR Ablates VISTA Dextramer Binding

Human CD4 T cells were isolated from whole blood and activated for 2 days with plated coated OKT3 & CD28.2. The T cells were then transfected with Cas9 ribonuclear proteins (RNPs) loaded with guide RNAs targeting either CD4, PSGL1, or a gRNA with no human sequence homology (non-targeting control). Transfections were done in triplicate. Following transfection, the cells were reactivated with CD3/CD28 coated Dynabeads® for 4 days. The cells were then stained with dextramer loaded with recombinant human avi-tagged VISTA to assess binding to VISTA. Percent of maximum VISTA binding was determined by dividing the average VISTA dextramer mean fluorescence intensity (MFI) of the knock-out population by the average VISTA dextramer MFI of the non-targeting control.

Figure 5:
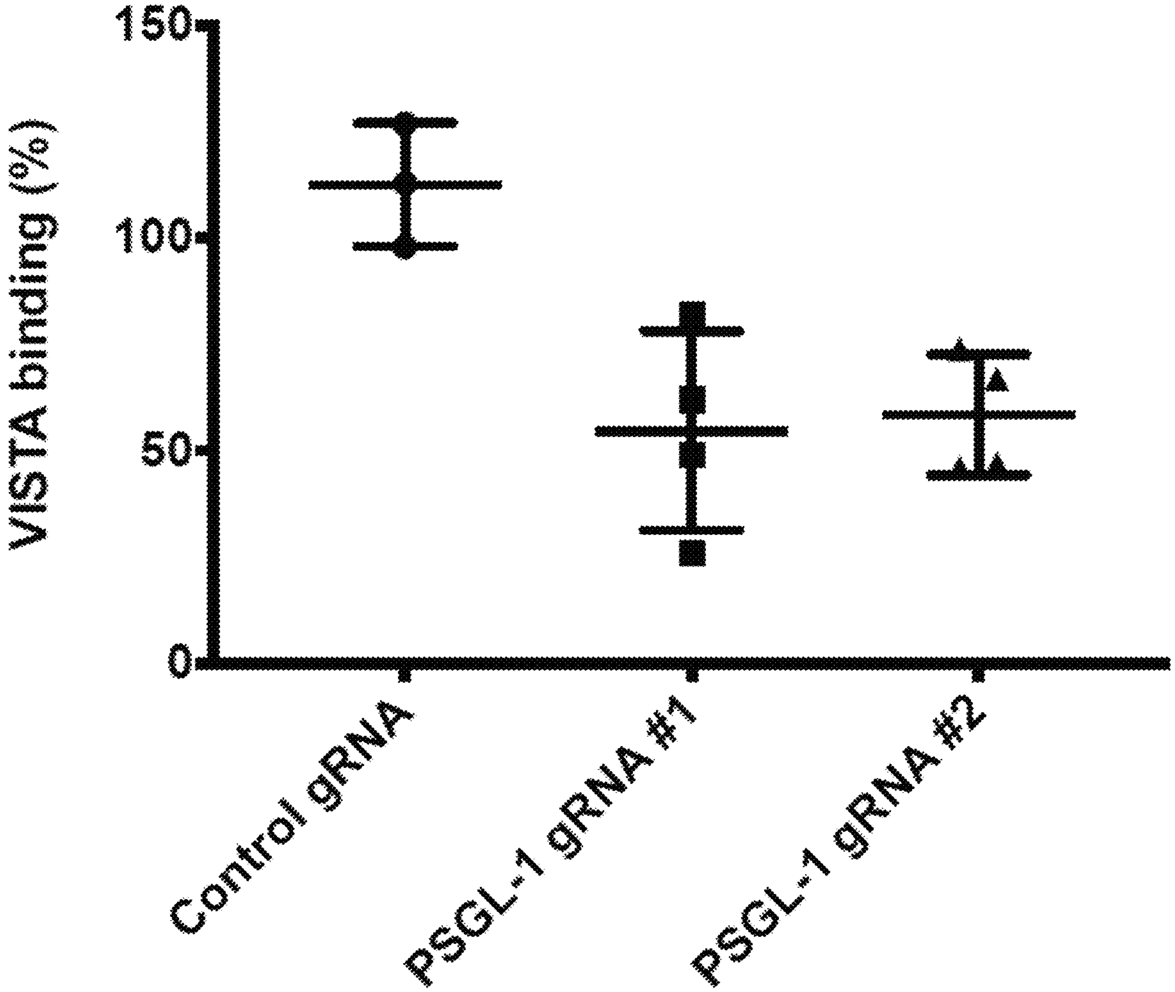
FIG. 5 shows the percentage of human VISTA binding to T cells ("control gRNA") and to PSGL-1 CRISPR knockout T cells ("PSGL-1 gRNA #1" and PSGL-1 gRNA #2", which are two clones obtained using two different guide RNAs).

The results are shown in FIG. 5, and indicate that VISTA binding to T cells was reduced by about half in T cells in which PSGL-1 was ablated. These results further suggest that PSGL-1 is a VISTA counter-receptor on T cells.

TABLE OF SEQUENCES

| SEQ ID NO | Description | Sequence |
|---|---|---|
| 1 | HumPSGL-1 isoform 1 precursor, with signal peptide NP_001193538 | MAVGASGLEG DKMAGAMPLQ LLLLLILLGP GNSLQLWDTW ADEAEKALGP LLARDRRQAT EYEYLDYDFL PETEPPEMLR NSTDTTPLTG PGTPESTTVE PAARRSTGLD AGGAVTELTT ELANMGNLST DSAAMEIQTT QPAATEAQTT QPVPTEAQTT PLAATEAQTT RLTATEAQTT PLAATEAQTT PPAATEAQTT QPTGLEAQTT APAAMEAQTT APAAMEAQTT PPAAMEAQTT QTTAMEAQTT APEATEAQTT QPTATEAQTT PLAAMEALST EPSATEALSM EPTTKRGLFI PFSVSSVTHK GIPMAASNLS VNYPVGAPDH ISVKQCLLAI LILALVATIF FVCTVVLAVR LSRKGHMYPV RNYSPTEMVC ISSLLPDGGE GPSATANGGL SKAKSPGLTP EPREDREGDD LTLHSFLP |
| 2 | Human PSGL-1, without signal peptide | LQLWDTW ADEAEKALGP LLARDRRQAT EYEYLDYDFL PETEPPEMLR NSTDTTPLTG PGTPESTTVE PAARRSTGLD AGGAVTELTT ELANMGNLST DSAAMEIQTT QPAATEAQTT QPVPTEAQTT PLAATEAQTT RLTATEAQTT PLAATEAQTT PPAATEAQTT QPTGLEAQTT APAAMEAQTT APAAMEAQTT PPAAMEAQTT QTTAMEAQTT APEATEAQTT QPTATEAQTT PLAAMEALST EPSATEALSM EPTTKRGLFI PFSVSSVTHK GIPMAASNLS VNYPVGAPDH ISVKQCLLAI LILALVATIF FVCTVVLAVR LSRKGHMYPV RNYSPTEMVC ISSLLPDGGE GPSATANGGL SKAKSPGLTP EPREDREGDD LTLHSFLP |
| 3 | Human PSGL-1 ECD, with signal peptide | MAVGASGLEG DKMAGAMPLQ LLLLLILLGP GNSLQLWDTW ADEAEKALGP LLARDRRQAT EYEYLDYDFL PETEPPEMLR NSTDTTPLTG PGTPESTTVE PAARRSTGLD AGGAVTELTT ELANMGNLST DSAAMEIQTT QPAATEAQTT QPVPTEAQTT PLAATEAQTT RLTATEAQTT PLAATEAQTT PPAATEAQTT QPTGLEAQTT APAAMEAQTT APAAMEAQTT PPAAMEAQTT QT |
| 4 | Human PSGL-1 ECD without signal peptide | LQLWDTW ADEAEKALGP LLARDRRQAT EYEYLDYDFL PETEPPEMLR NSTDTTPLTG PGTPESTTVE PAARRSTGLD AGGAVTELTT ELANMGNLST DSAAMEIQTT QPAATEAQTT QPVPTEAQTT PLAATEAQTT RLTATEAQTT PLAATEAQTT PPAATEAQTT QPTGLEAQTT APAAMEAQTT APAAMEAQTT PPAAMEAQTT QT |
| 5 | Human VISTA precursor, with signal peptide | MGVPTALEAG SWRWGSLLFA LFLAASLGPV AAFKVATPYS LYVCPEGQNV TLTCRLLGPV DKGHDVTFYK TWYRSSRGEV |

-continued

TABLE OF SEQUENCES

| SEQ ID NO | Description | Sequence |
|---|---|---|
| | (UniProtKB Ref. Q9H7M9, 19 Feb. 2014) | QTCSERRPIR NLTFQDLHLH HGGHQAANTS HDLAQRHGLE SASDHHGNFS ITMRNLTLLD SGLYCCLVVE IRHHHSEHRV HGAMELQVQT GKDAPSNCVV YPSSSQDSEN ITAAALATGA CIVGILCLPL ILLLVYKQRQ AASNRRAQEL VRMDSNIQGI ENPGFEASPP AQGIPEAKVR HPLSYVAQRQ PSESGRHLLS EPSTPLSPPG PGDVFFPSLD PVPDSPNFEV I |
| 6 | Human mature VISTA, without signal peptide | FKVATPYS LYVCPEGQNV TLTCRLLGPV DKGHDVTFYK TWYRSSRGEV QTCSERRPIR NLTFQDLHLH HGGHQAANTS HDLAQRHGLE SASDHHGNFS ITMRNLTLLD SGLYCCLVVE IRHHHSEHRV HGAMELQVQT GKDAPSNCVV YPSSSQDSEN ITAAALATGA CIVGILCLPL ILLLVYKQRQ AASNRRAQEL VRMDSNIQGI ENPGFEASPP AQGIPEAKVR HPLSYVAQRQ PSESGRHLLS EPSTPLSPPG PGDVFFPSLD PVPDSPNFEV I |
| 7 | Mouse VISTA precursor, with signal peptide (NCBI Ref NP_083008.1, 26 Feb. 2014) | MGVPAVPEAS SPRWGTLLLA IFLAASRGLV AAFKVTTPYS LYVCPEGQNA TLTCRILGPV SKGHDVTIYK TWYLSSRGEV QMCKEHRPIR NFTLQHLQHH GSHLKANASH DQPQKHGLEL ASDHHGNFSI TLRNVTPRDS GLYCCLVIEL KNHHPEQRFY GSMELQVQAG KGSGSTCMAS NEQDSDSITA AALATGACIV GILCLPLILL LVYKQRQVAS HRRAQELVRM DSSNTQGIEN PGFETTPPFQ GMPEAKTRPP LSYVAQRQPS ESGRYLLSDP STPLSPPGPG DVFFPSLDPV PDSPNSEAI |
| 8 | Mouse mature VISTA, without signal peptide | FKVTTPYS LYVCPEGQNA TLTCRILGPV SKGHDVTIYK TWYLSSRGEV QMCKEHRPIR NFTLQHLQHH GSHLKANASH DQPQKHGLEL ASDHHGNFSI TLRNVTPRDS GLYCCLVIEL KNHHPEQRFY GSMELQVQAG KGSGSTCMAS NEQDSDSITA AALATGACIV GILCLPLILL LVYKQRQVAS HRRAQELVRM DSSNTQGIEN PGFETTPPFQ GMPEAKTRPP LSYVAQRQPS ESGRYLLSDP STPLSPPGPG DVFFPSLDPV PDSPNSEAI |
| 9 | Human VISTA ECD-Fc, without signal peptide | FKVATPYSLY VCPEGQNVTL TCRLLGPVDK GHDVTFYKTW YRSSRGEVQT CSERRPIRNL TFQDLHLHHG GHQAANTSHD LAQRHGLESA SDHHGNFSIT MRNLTLLDSG LYCCLVVEIR HHHSEHRVHG AMELQVQTGK DAPSNCVVYP SSSQDSENIT AAAGTSGSSG SGSGGSGSGG GGRSVPRDSG CKPCICTVPE VSSVFIFPPK PKDVLTITLT PKVTCVVVDI SKDDPEVQFS WFVDDVEVHT AQTKPREEQI NSTFRSVSEL PIMHQDWLNG KEFKCRVNSA AFPAPIEKTI SKTKGRPKAP QVYTIPPPKE QMAKDKVSLT CMITNFFPED ITVEWQWNGQ PAENYKNTQP IMDTDGSYFV YSKLNVQKSN WEAGNTFTCS VLHEGLHNHH TEKSLSHSPG K |
| 10 | His-tagged human VISTA extracellular domain (ECD) | FKVATPYS LYVCPEGQNV TLTCRLLGPV DKGHDVTFYK TWYRSSRGEV QTCSERRPIR NLTFQDLHLH HGGHQAANTS HDLAQRHGLE SASDHHGNFS ITMRNLTLLD SGLYCCLVVE IRHHHSEHRV HGAMELQVQT GKDAPSNCVV YPSSSQDSEN ITAAALATGA CIVGILCLPL ILLLVYKQRQ AASNRRAQEL VRMDSNIQGI ENPGFEASPP AQGIPEAKVR HPLSYVAQRQ PSESGRHLLS EPSTPLSPPG PGDVFFPSLD PVPDSPNFEV IGHHHHHH |
| 11 | Fc C237S | EPKSSDKTHT CPPCPAPELL GGPSVFLFPP KPKDTLMISR TPEVTCVVVD VSHEDPEVKF NWYVDGVEVH NAKTKPREEQ YNSTYRVVSV LTVLHQDWLN GKEYKCKVSN KALPAPIEKT ISKAKGQPRE PQVYTLPPSR DELTKNQVSL TCLVKGFYPS DIAVEWESNG QPENNYKTTP PVLDSDGSFF LYSKLTVDKS RWQQGNVFSC SVMHEALHNH YTQKSLSLSP GK |
| 12 | Exemplary Fc #1 | ERKCCVECPP CPAPPVAGPS VFLFPPKPKD TLMISRTPEV TCVVVDVSHE DPEVQFNWYV DGVEVHNAKT KPREEQFNST FRVVSVLTVV HQDWLNGKEY KCKVSNKGLP APIEKTISKT KGQPREPQVY TLPPSREEMT KNQVSLTCLV KGFYPSDIAV EWESNGQPEN NYKTTPPMLD SDGSFFLYSK LTVDKSRWQQ GNVFSCSVMH EALHNHYTQK SLSLSPGK |
| 13 | Exemplary Fc #2 | ESKYGPPCPS CPAPEFLGGP SVFLFPPKPK DTLMISRTPE VTCVVVDVSQ EDPEVQFNWY VDGVEVHNAK TKPREEQFNS TYRVVSVLTV LHQDWLNGKE YKCKVSNKGL PSSIEKTISK AKGQPREPQV YTLPPSQEEM TKNQVSLTCL VKGFYPSDIA VEWESNGQPE NNYKTTPPVL DSDGSFFLYS RLTVDKSRWQ EGNVFSCSVM HEALHNHYTQ KSLSLSLGK |

-continued

TABLE OF SEQUENCES

| SEQ ID NO | Description | Sequence |
|---|---|---|
| 14 | Human PSGL-1 isoform 2 precursor, with signal peptide | MPLQLLLLLI LLGPGNSLQL WDTWADEAEK ALGPLLARDR RQATEYEYLD YDFLPETEPP EMLRNSTDTT PLTGPGTPES TTVEPAARRS TGLDAGGAVT ELTTELANMG NLSTDSAAME IQTTQPAATE AQTTQPVPTE AQTTPLAATE AQTTRLTATE AQTTPLAATE AQTTPPAATE AQTTQPTGLE AQTTAPAAME AQTTAPAAME AQTTPPAAME AQTTQTTAME AQTTAPEATE AQTTQPTATE AQTTPLAAME ALSTEPSATE ALSMEPTTKR GLFIPFSVSS VTHKGIPMAA SNLSVNYPVG APDHISVKQC LLAILILALV ATIFFVCTVV LAVRLSRKGH MYPVRNYSPT EMVCISSLLP DGGEGPSATA NGGLSKAKSP GLTPEPREDR EGDDLTLHSF LP |
| 15 | Human PSGL-1 isoform 2, without signal peptide | LQL WDTWADEAEK ALGPLLARDR RQATEYEYLD YDFLPETEPP EMLRNSTDTT PLTGPGTPES TTVEPAARRS TGLDAGGAVT ELTTELANMG NLSTDSAAME IQTTQPAATE AQTTQPVPTE AQTTPLAATE AQTTRLTATE AQTTPLAATE AQTTPPAATE AQTTQPTGLE AQTTAPAAME AQTTAPAAME AQTTPPAAME AQTTQTTAME AQTTAPEATE AQTTQPTATE AQTTPLAAME ALSTEPSATE ALSMEPTTKR GLFIPFSVSS VTHKGIPMAA SNLSVNYPVG APDHISVKQC LLAILILALV ATIFFVCTVV LAVRLSRKGH MYPVRNYSPT EMVCISSLLP DGGEGPSATA NGGLSKAKSP GLTPEPREDR EGDDLTLHSF LP |
| 16 | Human PSGL-1 isoform 2 ECD with signal peptide | MPLQLLLLLI LLGPGNSLQL WDTWADEAEK ALGPLLARDR RQATEYEYLD YDFLPETEPP EMLRNSTDTT PLTGPGTPES TTVEPAARRS TGLDAGGAVT ELTTELANMG NLSTDSAAME IQTTQPAATE AQTTQPVPTE AQTTPLAATE AQTTRLTATE AQTTPLAATE AQTTPPAATE AQTTQPTGLE AQTTAPAAME AQTTAPAAME AQTTPPAAME AQTTQT |
| 17 | Human PSGL-1 isoform 2 ECD, without signal peptide | LQL WDTWADEAEK ALGPLLARDR RQATEYEYLD YDFLPETEPP EMLRNSTDTT PLTGPGTPES TTVEPAARRS TGLDAGGAVT ELTTELANMG NLSTDSAAME IQTTQPAATE AQTTQPVPTE AQTTPLAATE AQTTRLTATE AQTTPLAATE AQTTPPAATE AQTTQPTGLE AQTTAPAAME AQTTAPAAME AQTTPPAAME AQTTQT |
| 18 | Human PSGL-1 ECD(N-terminal positions 42 to 295 of a full length Human PSGL-1 Accession No. AAC50061) | QATEYEYLD YDFLPETEPP EMLRNSTDTT PLTGPGTPES TTVEPAARRS TGLDAGGAVT ELTTELANMG NLSTDSAAME IQTTQPAATE AQTTPLAATE AQTTRLTATE AQTTPLAATE AQTTPPAATE AQTTQPTGLE AQTTAPAAME AQTTAPAAME AQTTPPAAME AQTTQTTAME AQTTAPEATE AQTTQPTATE AQTTPLAAME ALSTEPSATE ALSMEPTTKR GLFIPFSVSS VTHKGIPMAA SNLSV |
| 19 | Exemplary fusion protein linker sequence | IEGRMD |

SEQUENCE LISTING

```
Sequence total quantity: 19
SEQ ID NO: 1           moltype = AA  length = 428
FEATURE                Location/Qualifiers
source                 1..428
                       mol_type = protein
                       organism = Homo sapiens
SEQUENCE: 1
MAVGASGLEG DKMAGAMPLQ LLLLLILLGP GNSLQLWDTW ADEAEKALGP LLARDRRQAT  60
EYEYLDYDFL PETEPPEMLR NSTDTTPLTG PGTPESTTVE PAARRSTGLD AGGAVTELTT  120
ELANMGNLST DSAAMEIQTT QPAATEAQTT QPVPTEAQTT PLAATEAQTT RLTATEAQTT  180
PLAATEAQTT PPAATEAQTT QPTGLEAQTT APAAMEAQTT APAAMEAQTT PPAAMEAQTT  240
QTTAMEAQTT APEATEAQTT QPTATEAQTT PLAAMEALST EPSATEALSM EPTTKRGLFI  300
PFSVSSVTHK GIPMAASNLS VNYPVGAPDH ISVKQCLLAI LILALVATIF FVCTVVLAVR  360
LSRKGHMYPV RNYSPTEMVC ISSLLPDGGE GPSATANGGL SKAKSPGLTP EPREDREGDD  420
LTLHSFLP                                                           428

SEQ ID NO: 2           moltype = AA  length = 395
FEATURE                Location/Qualifiers
source                 1..395
                       mol_type = protein
```

```
                         organism = Homo sapiens
SEQUENCE: 2
LQLWDTWADE AEKALGPLLA RDRRQATEYE YLDYDFLPET EPPEMLRNST DTTPLTGPGT  60
PESTTVEPAA RRSTGLDAGG AVTELTTELA NMGNLSTDSA AMEIQTTQPA ATEAQTTQPV  120
PTEAQTTPLA ATEAQTTRLT ATEAQTTPLA ATEAQTTPPA ATEAQTTQPT GLEAQTTAPA  180
AMEAQTTAPA AMEAQTTPPA AMEAQTTQTT AMEAQTTAPE ATEAQTTQPT ATEAQTTPLA  240
AMEALSTEPS ATEALSMEPT TKRGLFIPFS VSSVTHKGIP MAASNLSVNY PVGAPDHISV  300
KQCLLAILIL ALVATIFFVC TVVLAVRLSR KGHMYPVRNY SPTEMVCISS LLPDGGEGPS  360
ATANGGLSKA KSPGLTPEPR EDREGDDLTL HSFLP                            395

SEQ ID NO: 3             moltype = AA  length = 242
FEATURE                  Location/Qualifiers
source                   1..242
                         mol_type = protein
                         organism = synthetic construct
SEQUENCE: 3
MAVGASGLEG DKMAGAMPLQ LLLLLILLGP GNSLQLWDTW ADEAEKALGP LLARDRRQAT  60
EYEYLDYDFL PETEPPEMLR NSTDTTPLTG PGTPESTTVE PAARRSTGLD AGGAVTELTT  120
ELANMGNLST DSAAMEIQTT QPAATEAQTT QPVPTEAQTT PLAATEAQTT RLTATEAQTT  180
PLAATEAQTT PPAATEAQTT QPTGLEAQTT APAAMEAQTT APAAMEAQTT PPAAMEAQTT  240
QT                                                                242

SEQ ID NO: 4             moltype = AA  length = 209
FEATURE                  Location/Qualifiers
source                   1..209
                         mol_type = protein
                         organism = synthetic construct
SEQUENCE: 4
LQLWDTWADE AEKALGPLLA RDRRQATEYE YLDYDFLPET EPPEMLRNST DTTPLTGPGT  60
PESTTVEPAA RRSTGLDAGG AVTELTTELA NMGNLSTDSA AMEIQTTQPA ATEAQTTQPV  120
PTEAQTTPLA ATEAQTTRLT ATEAQTTPPA ATEAQTTQPT GLEAQTTAPA            180
AMEAQTTAPA AMEAQTTPPA AMEAQTTQT                                   209

SEQ ID NO: 5             moltype = AA  length = 311
FEATURE                  Location/Qualifiers
source                   1..311
                         mol_type = protein
                         organism = Homo sapiens
SEQUENCE: 5
MGVPTALEAG SWRWGSLLFA LFLAASLGPV AAFKVATPYS LYVCPEGQNV TLTCRLLGPV  60
DKGHDVTFYK TWYRSSRGEV QTCSERRPIR NLTFQDLHLH HGGHQAANTS HDLAQRHGLE  120
SASDHHGNFS ITMRNLTLLD SGLYCCLVVE IRHHHSEHRV HGAMELQVQT GKDAPSNCVV  180
YPSSSQDSEN ITAAALATGA CIVGILCLPL ILLLVYKQRQ AASNRRAQEL VRMDSNIQGI  240
ENPGFEASPP AQGIPEAKVR HPLSYVAQRQ PSESGRHLLS EPSTPLSPPG PGDVFFPSLD  300
PVPDSPNFEV I                                                      311

SEQ ID NO: 6             moltype = AA  length = 279
FEATURE                  Location/Qualifiers
source                   1..279
                         mol_type = protein
                         organism = Homo sapiens
SEQUENCE: 6
FKVATPYSLY VCPEGQNVTL TCRLLGPVDK GHDVTFYKTW YRSSRGEVQT CSERRPIRNL  60
TFQDLHLHHG GHQAANTSHD LAQRHGLESA SDHHGNFSIT MRNLTLLDSG LYCCLVVEIR  120
HHHSEHRVHG AMELQVQTGK DAPSNCVVYP SSSQDSENIT AAALATGACI VGILCLPLIL  180
LLVYKQRQAA SNRRAQELVR MDSNIQGIEN PGFEASPPAQ GIPEAKVRHP LSYVAQRQPS  240
ESGRHLLSEP STPLSPPGPG DVFFPSLDPV PDSPNFEVI                        279

SEQ ID NO: 7             moltype = AA  length = 309
FEATURE                  Location/Qualifiers
source                   1..309
                         mol_type = protein
                         organism = Mus musculus
SEQUENCE: 7
MGVPAVPEAS SPRWGTLLLA IFLAASRGLV AAFKVTTPYS LYVCPEGQNA TLTCRILGPV  60
SKGHDVTIYK TWYLSSRGEV QMCKEHRPIR NFTLQHLQHH GSHLKANASH DQPQKHGLEL  120
ASDHHGNFSI TLRNVTPRDS GLYCCLVIEL KNHHPEQRFY GSMELQVQAG KGSGSTCMAS  180
NEQDSDSITA AALATGACIV GILCLPLILL LVYKQRQVAS HRRAQELVRM DSSNTQGIEN  240
PGFETTPPFQ GMPEAKTRPP LSYVAQRQPS ESGRYLLSDP STPLSPPGPG DVFFPSLDPV  300
PDSPNSEAI                                                         309

SEQ ID NO: 8             moltype = AA  length = 277
FEATURE                  Location/Qualifiers
source                   1..277
                         mol_type = protein
                         organism = Mus musculus
SEQUENCE: 8
FKVTTPYSLY VCPEGQNATL TCRILGPVSK GHDVTIYKTW YLSSRGEVQM CKEHRPIRNF  60
TLQHLQHHGS HLKANASHDQ PQKHGLELAS DHHGNFSITL RNVTPRDSGL YCCLVIELKN  120
```

-continued

```
HHPEQRFYGS MELQVQAGKG SGSTCMASNE QDSDSITAAA LATGACIVGI LCLPLILLLV  180
YKQRQVASHR RAQELVRMDS SNTQGIENPG FETTPPFQGM PEAKTRPPLS YVAQRQPSES  240
GRYLLSDPST PLSPPGPGDV FFPSLDPVPD SPNSEAI                          277

SEQ ID NO: 9           moltype = AA  length = 411
FEATURE                Location/Qualifiers
source                 1..411
                       mol_type = protein
                       organism = synthetic construct
SEQUENCE: 9
FKVATPYSLY VCPEGQNVTL TCRLLGPVDK GHDVTFYKTW YRSSRGEVQT CSERRPIRNL  60
TFQDLHLHHG GHQAANTSHD LAQRHGLESA SDHHGNFSIT MRNLTLLDSG LYCCLVVEIR  120
HHHSEHRVHG AMELQVQTGK DAPSNCVVYP SSSQDSENIT AAAGTSGSSG SGSGGSGSGG  180
GGRSVPRDSG CKPCICTVPE VSSVFIFPPK PKDVLTITLT PKVTCVVVDI SKDDPEVQFS  240
WFVDDVEVHT AQTKPREEQI NSTFRSVSEL PIMHQDWLNG KEFKCRVNSA AFPAPIEKTI  300
SKTKGRPKAP QVYTIPPPKE QMAKDKVSLT CMITNFFPED ITVEWQWNGQ PAENYKNTQP  360
IMDTDGSYFV YSKLNVQKSN WEAGNTFTCS VLHEGLHNHH TEKSLSHSPG K           411

SEQ ID NO: 10          moltype = AA  length = 286
FEATURE                Location/Qualifiers
source                 1..286
                       mol_type = protein
                       organism = synthetic construct
SEQUENCE: 10
FKVATPYSLY VCPEGQNVTL TCRLLGPVDK GHDVTFYKTW YRSSRGEVQT CSERRPIRNL  60
TFQDLHLHHG GHQAANTSHD LAQRHGLESA SDHHGNFSIT MRNLTLLDSG LYCCLVVEIR  120
HHHSEHRVHG AMELQVQTGK DAPSNCVVYP SSSQDSENIT AAALATGACI VGILCLPLIL  180
LLVYKQRQAA SNRRAQELVR MDSNIQGIEN PGFEASPPAQ GIPEAKVRHP LSYVAQRQPS  240
ESGRHLLSEP STPLSPPGPG DVFFPSLDPV PDSPNFEVIG HHHHHH                286

SEQ ID NO: 11          moltype = AA  length = 232
FEATURE                Location/Qualifiers
source                 1..232
                       mol_type = protein
                       organism = synthetic construct
SEQUENCE: 11
EPKSSDKTHT CPPCPAPELL GGPSVFLFPP KPKDTLMISR TPEVTCVVVD VSHEDPEVKF  60
NWYVDGVEVH NAKTKPREEQ YNSTYRVVSV LTVLHQDWLN GKEYKCKVSN KALPAPIEKT  120
ISKAKGQPRE PQVYTLPPSR DELTKNQVSL TCLVKGFYPS DIAVEWESNG QPENNYKTTP  180
PVLDSDGSFF LYSKLTVDKS RWQQGNVFSC SVMHEALHNH YTQKSLSLSP GK          232

SEQ ID NO: 12          moltype = AA  length = 228
FEATURE                Location/Qualifiers
source                 1..228
                       mol_type = protein
                       organism = synthetic construct
SEQUENCE: 12
ERKCCVECPP CPAPPVAGPS VFLFPPKPKD TLMISRTPEV TCVVVDVSHE DPEVQFNWYV  60
DGVEVHNAKT KPREEQFNST FRVVSVLTVV HQDWLNGKEY KCKVSNKGLP APIEKTISKT  120
KGQPREPQVY TLPPSREEMT KNQVSLTCLV KGFYPSDIAV EWESNGQPEN NYKTTPPMLD  180
SDGSFFLYSK LTVDKSRWQQ GNVFSCSVMH EALHNHYTQK SLSLSPGK              228

SEQ ID NO: 13          moltype = AA  length = 229
FEATURE                Location/Qualifiers
source                 1..229
                       mol_type = protein
                       organism = synthetic construct
SEQUENCE: 13
ESKYGPPCPS CPAPEFLGGP SVFLFPPKPK DTLMISRTPE VTCVVVDVSQ EDPEVQFNWY  60
VDGVEVHNAK TKPREEQFNS TYRVVSVLTV LHQDWLNGKE YKCKVSNKGL PSSIEKTISK  120
AKGQPREPQV YTLPPSQEEM TKNQVSLTCL VKGFYPSDIA VEWESNGQPE NNYKTTPPVL  180
DSDGSFFLYS RLTVDKSRWQ EGNVFSCSVM HEALHNHYTQ KSLSLSLGK             229

SEQ ID NO: 14          moltype = AA  length = 412
FEATURE                Location/Qualifiers
source                 1..412
                       mol_type = protein
                       organism = Homo sapiens
SEQUENCE: 14
MPLQLLLLLI LLGPGNSLQL WDTWADEAEK ALGPLLARDR RQATEYEYLD YDFLPETEPP  60
EMLRNSTDTT PLTGPGTPES TTVEPAARRS TGLDAGGAVT ELTTELANMG NLSTDSAAME  120
IQTTQPAATE AQTTQPVPTE AQTTPLAATE AQTTRLTATE AQTTPLAATE AQTTPPAATE  180
AQTTQPTGLE AQTTAPAAME AQTTAPAAME AQTTPPAAME AQTTQTTAME AQTTAPEATE  240
AQTTQPTATE AQTTPLAAME ALSTEPSATE ALSMEPTTKR GLFIPFSVSS VTHKGIPMAA  300
SNLSVNYPVG APDHISVKQC LLAILILALV ATIFFVCTVV LAVRLSRKGH MYPVRNYSPT  360
EMVCISSLLP DGGEGPSATA NGGLSKAKSP GLTPEPREDR EGDDLTLHSF LP          412

SEQ ID NO: 15          moltype = AA  length = 395
FEATURE                Location/Qualifiers
```

-continued

```
source                  1..395
                        mol_type = protein
                        organism = Homo sapiens
SEQUENCE: 15
LQLWDTWADE AEKALGPLLA RDRRQATEYE YLDYDFLPET EPPEMLRNST DTTPLTGPGT  60
PESTTVEPAA RRSTGLDAGG AVTELTTELA NMGNLSTDSA AMEIQTTQPA ATEAQTTQPV  120
PTEAQTTPLA ATEAQTTRLT ATEAQTTPLA ATEAQTTPPA ATEAQTTQPT GLEAQTTAPA  180
AMEAQTTAPA AMEAQTTPPA AMEAQTTQTT AMEAQTTAPE ATEAQTTQPT ATEAQTTPLA  240
AMEALSTEPS ATEALSMEPT TKRGLFIPFS VSSVTHKGIP MAASNLSVNY PVGAPDHISV  300
KQCLLAILIL ALVATIFFVC TVVLAVRLSR KGHMYPVRNY SPTEMVCISS LLPDGGEGPS  360
ATANGGLSKA KSPGLTPEPR EDREGDDLTL HSFLP                            395

SEQ ID NO: 16           moltype = AA  length = 226
FEATURE                 Location/Qualifiers
source                  1..226
                        mol_type = protein
                        organism = synthetic construct
SEQUENCE: 16
MPLQLLLLLI LLGPGNSLQL WDTWADEAEK ALGPLLARDR RQATEYEYLD YDFLPETEPP  60
EMLRNSTDTT PLTGPGTPES TTVEPAARRS TGLDAGGAVT ELTTELANMG NLSTDSAAME  120
IQTTQPAATE AQTTQPVPTE AQTTPLAATE AQTTRLTATE AQTTPLAATE AQTTPPAATE  180
AQTTQPTGLE AQTTAPAAME AQTTAPAAME AQTTPPAAME AQTTQT                226

SEQ ID NO: 17           moltype = AA  length = 209
FEATURE                 Location/Qualifiers
source                  1..209
                        mol_type = protein
                        organism = synthetic construct
SEQUENCE: 17
LQLWDTWADE AEKALGPLLA RDRRQATEYE YLDYDFLPET EPPEMLRNST DTTPLTGPGT  60
PESTTVEPAA RRSTGLDAGG AVTELTTELA NMGNLSTDSA AMEIQTTQPA ATEAQTTQPV  120
PTEAQTTPLA ATEAQTTRLT ATEAQTTPLA ATEAQTTPPA ATEAQTTQPT GLEAQTTAPA  180
AMEAQTTAPA AMEAQTTPPA AMEAQTTQT                                   209

SEQ ID NO: 18           moltype = AA  length = 254
FEATURE                 Location/Qualifiers
source                  1..254
                        mol_type = protein
                        organism = synthetic construct
SEQUENCE: 18
QATEYEYLDY DFLPETEPPE MLRNSTDTTP LTGPGTPEST TVEPAARRST GLDAGGAVTE  60
LTTELANMGN LSTDSAAMEI QTTQPAATEA QTTPLAATEA QTTRLTATEA QTTPLAATEA  120
QTTPPAATEA QTTQPTGLEA QTTAPAAMEA QTTAPAAMEA QTTPPAAMEA QTTQTTAMEA  180
QTTAPEATEA QTTQPTATEA QTTPLAAMEA LSTEPSATEA LSMEPTTKRG LFIPFSVSSV  240
THKGIPMAAS NLSV                                                   254

SEQ ID NO: 19           moltype = AA  length = 6
FEATURE                 Location/Qualifiers
source                  1..6
                        mol_type = protein
                        organism = synthetic construct
SEQUENCE: 19
IEGRMD                                                            6
```

The invention claimed is:

1. A method of treating cancer and/or of inhibiting binding of PSGL-1 to VISTA in a human subject, comprising administering to the subject an effective amount of at least one PSGL-1 antagonist, wherein the PSGL-1 antagonist binds to VISTA at a pH in the range of pH 5.5 to pH 6.5 or to PSGL-1 at a pH in the range of pH 5.5 to pH 6.5, and wherein the PSGL-1 antagonist is selected from a PSGL-1 antibody and a VISTA antibody.

2. The method of claim 1, wherein the method further comprises administering to the subject an effective amount of a therapeutic agent selected from chemotherapeutic agents, anti-angiogenesis agents, growth inhibitory agents, immune-oncology agents, and anti-neoplastic compositions.

3. The method of claim 1, wherein the antibody is selected from a chimeric antibody, a humanized antibody, a human antibody, and an antibody fragment selected from an Fv, a single-chain Fv (scFv), a Fab, a Fab', and a $(Fab')_2$.

4. The method of claim 1, wherein the PSGL-1 antagonist blocks binding of PSGL-1 to VISTA at a pH in the range of pH 5.5 to pH 6.5.

5. The method of claim 1, wherein the PSGL-1 antagonist binds to VISTA or PSGL-1 with a $K_D$ of 10 nM to 0.0001 nM.

* * * * *